(12) United States Patent
Naidu et al.

(10) Patent No.: US 8,791,108 B2
(45) Date of Patent: Jul. 29, 2014

(54) INHIBITORS OF HUMAN IMMUNODEFICIENCY VIRUS REPLICATION

(75) Inventors: B. Narasimhulu Naidu, Durham, CT (US); Manoj Patel, Berlin, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 104 days.

(21) Appl. No.: 13/570,738

(22) Filed: Aug. 9, 2012

(65) Prior Publication Data

US 2013/0203748 A1    Aug. 8, 2013

Related U.S. Application Data

(60) Provisional application No. 61/525,032, filed on Aug. 18, 2011.

(51) Int. Cl.
| | | |
|---|---|---|
| *A61K 31/535* | (2006.01) | |
| *A61K 31/519* | (2006.01) | |
| *C07D 487/00* | (2006.01) | |
| *C07D 413/00* | (2006.01) | |
| *C07D 498/02* | (2006.01) | |

(52) U.S. Cl.
USPC ............ 514/230.5; 514/259.3; 514/234.2; 544/281; 544/117; 544/105

(58) Field of Classification Search
USPC ......... 514/230.5, 259.3, 234.2; 544/281, 117, 544/105
See application file for complete search history.

(56) References Cited

U.S. PATENT DOCUMENTS

| | | |
|---|---|---|
| 2008/0221159 A1 | 9/2008 | Tsantrizos et al. |
| 2010/0292227 A1 | 11/2010 | Yoakim et al. |
| 2010/0305115 A1 | 12/2010 | Carson et al. |
| 2010/0311735 A1 | 12/2010 | Tsantrizos et al. |
| 2011/0028464 A1 | 2/2011 | Tsantrizos et al. |
| 2011/0044994 A1* | 2/2011 | Chan-Hui et al. ......... 424/148.1 |
| 2011/0118249 A1 | 5/2011 | Tsantrizos et al. |
| 2011/0207626 A1 | 8/2011 | Inazawa et al. |
| 2012/0129840 A1 | 5/2012 | Chalton et al. |
| 2012/0316161 A1 | 12/2012 | Carlens et al. |
| 2013/0203727 A1 | 8/2013 | Babaoglu et al. |
| 2013/0210801 A1 | 8/2013 | Babaoglu et al. |
| 2013/0210857 A1 | 8/2013 | Walker et al. |

FOREIGN PATENT DOCUMENTS

| | | |
|---|---|---|
| WO | WO2012/102985 | 8/2012 |
| WO | WO2012/140243 | 10/2012 |

OTHER PUBLICATIONS

U.S. Appl. No. 13/782,198, filed Mar. 1, 2013, Pendri et al.
U.S. Appl. No. 13/782,996, filed Mar. 1, 2003, Zheng et al.

* cited by examiner

*Primary Examiner* — Jeffrey H Murray
*Assistant Examiner* — Oluwafemi Masha
(74) *Attorney, Agent, or Firm* — James Epperson

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

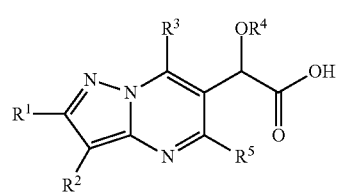

15 Claims, No Drawings

INHIBITORS OF HUMAN IMMUNODEFICIENCY VIRUS REPLICATION

CROSS REFERENCE TO RELATED APPLICATIONS

This patent application claims the benefit of U.S. provisional patent application No. 61/525,032 filed Aug. 18, 2011.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33 million people worldwide are infected with the virus (UNAIDS: Report on the Global HIV/AIDS Epidemic, December 1998). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: however, the effect is only temporary as the virus readily develops resistance to all known agents used as monotherapy. However, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641 and WO2011076765.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

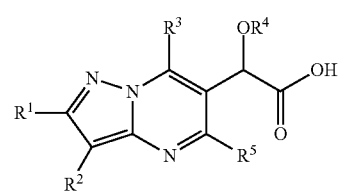

where:
$R^1$ is $CONR^6R^7$;
$R^2$ is hydrogen, halo, or alkyl;
$R^3$ is alkyl; alkenyl; cycloalkyl or cycloalkenyl substituted with 0-2 alkyl substituents; azetidinyl, pyrrolidinyl, piperidinyl, piperazinyl, morpholinyl, homopiperidinyl, homopiperazinyl, or homomorpholinyl substituted with 0-3 substituents selected from halo, alkyl, haloalkyl, hydroxy, alkoxy, haloalkoxy, carboxy, and carboxamido; or $Ar^2$;
$R^4$ is alkyl or haloalkyl;
$R^5$ is alkyl;
$R^6$ is alkyl, $(R^8)$alkyl, $Ar^1$, $(Ar^1)$alkyl, $(Ar^1)$alkenyl, $(Ar^1)$alkynyl, $(Ar^1)$cycloalkyl, alkylSO$_2$, $(Ar^1)$SO$_2$, or $(Ar^1)$alkylSO$_2$;
$R^7$ is hydrogen, alkyl, or alkoxy;
or where $NR^6R^7$ together form piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, $(Ar^3)$alkyl, and $Ar^3$;
$R^8$ is adamantyl, hydroxyadamantyl, hydroxycycloalkyl, tetrahydrofuranyl, tetrahydropyranyl, pyrrolidinonyl, alkoxy, alkylthio, phenoxy, or (phenyl)NH; or $R^8$ is piperidinyl, piperazinyl, morpholinyl, or tetrahydronapthalinyl, and is substituted with 0-1 substituents selected from alkyl, alkylCO, alkylCO$_2$, cycloalkylCO, cycloalkylCO$_2$, $(Ar^3)$alkyl, $Ar^3$, benzodioxolyl, piperidinyl morpholinyl, and (morpholinyl)ethyl;

$R^9$ is piperidinyl, piperazinyl, or morpholinyl;
$R^{10}$ is hydrogen or alkyl;
$R^{11}$ is hydrogen or alkyl;
or $NR^{10}R^{11}$ is piperidinyl, piperazinyl, or morpholinyl;
$Ar^1$ is phenyl, pyridinyl, pyrrolyl, furanyl, thienyl, pyrazolyl, isoxazolyl, isothiazolyl, imidazolyl, oxazolyl, thiazolyl, benzodioxolyl, or benzthiazolyl, and is substituted with 0-5 substituents selected from halo, hydroxy, alkoxy, cyano, alkyl, cycloalkyl, haloalkyl, haloalkoxy, phenoxy, $NR^{10}R^{11}$, $CONR^{10}R^{11}$, alkylSO$_2$, SO$_2$NR$^{10}$R$^{11}$, Ar$^3$SO$_2$, (Ar$^3$)alkylSO$_2$, R$^9$, and Ar$^4$;
$Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;
or $Ar^2$ is $Ar^a$ is phenyl substituted with 0-3 substituents selected from halo, alkyl, and alkoxy; and
$Ar^4$ is phenyl, pyridinyl, pyrimidinyl, pyrrolyl, pyrazolyl, imidazolyl, or triazolyl, and is substituted with 0-1 alkyl substituents;
or a pharmaceutically acceptable salt thereof.

Another aspect of the invention is a compound of formula I
where:
$R^1$ is $CONR^6R^7$;
$R^2$ is hydrogen, halo, or alkyl;
$R^3$ is alkyl, cycloalkyl, or $Ar^2$;
$R^4$ is alkyl or haloalkyl;
$R^5$ is alkyl;
$R^6$ is $(R^8)$alkyl, $Ar^1$, $(Ar^1)$alkyl, $(Ar^1)$alkenyl, $(Ar^1)$alkynyl, $(Ar^1)$cycloalkyl, alkylSO$_2$, $(Ar^1)$SO$_2$, or $(Ar^1)$alkylSO$_2$;
$R^7$ is hydrogen, alkyl, or alkoxy;
or where $NR^6R^7$ together form piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, (Ar$^3$)alkyl, and Ar$^3$;
$R^8$ is adamantyl, hydroxyadamantyl, hydroxycycloalkyl, tetrahydrofuranyl, tetrahydropyranyl, pyrrolidinonyl, alkoxy, alkylthio, phenoxy, or (phenyl)NH;
or $R^8$ is piperidinyl, piperazinyl, morpholinyl, or tetrahydronapthalinyl, and is substituted with 0-1 substituents selected from alkyl, alkylCO, alkylCO$_2$, cycloalkylCO, cycloalkylCO$_2$, (Ar$^3$)alkyl, Ar$^3$, benzodioxolyl, piperidinyl morpholinyl, and (morpholinyl)ethyl;
$R^9$ is piperidinyl, piperazinyl, or morpholinyl;
$R^{10}$ is hydrogen or alkyl;
$R^{11}$ is hydrogen or alkyl;
or $NR^{10}R^{11}$ is piperidinyl, piperazinyl, or morpholinyl;
$Ar^1$ is phenyl, pyridinyl, pyrrolyl, furanyl, thienyl, pyrazolyl, isoxazolyl, isothiazolyl, imidazolyl, oxazolyl, thiazolyl, benzodioxolyl, or benzthiazolyl, and is substituted with 0-5 substituents selected from halo, hydroxy, alkoxy, cyano, alkyl, cycloalkyl, haloalkyl, haloalkoxy, phenoxy, $NR^{10}R^{11}$, $CONR^{10}R^{11}$, alkylSO$_2$, SO$_2$NR$^{10}$R$^{11}$, Ar$^3$SO$_2$, (Ar$^3$)alkylSO$_2$, R$^9$, and Ar$^4$;
$Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;
or $Ar^2$ is $Ar^3$ is phenyl substituted with 0-3 substituents selected from halo, alkyl, and alkoxy; and
$Ar^4$ is phenyl, pyridinyl, pyrimidinyl, pyrrolyl, pyrazolyl, imidazolyl, or triazolyl, and is substituted with 0-1 alkyl substituents;

or a pharmaceutically acceptable salt thereof.

Another aspect of the invention is a compound of formula I where:
$R^1$ is $CONR^6R^7$;
$R^2$ is hydrogen;
$R^3$ is $Ar^2$;
$R^4$ is alkyl;
$R^5$ is alkyl;
$R^6$ is hydrogen, alkyl, alkenyl, alkynyl, (cycloalkyl)alkyl, cycloalkyl, cycloalkenyl, alkenylcycloalkyl, alkynylcycloalkyl, haloalkyl, haloalkenyl, haloalkynyl, $(R^8)$alkyl, $Ar^1$, $(Ar^1)$alkyl, $(Ar^1)$alkenyl, $(Ar^1)$alkynyl, $(Ar^1)$cycloalkyl, alkylSO$_2$, $(Ar^1)SO_2$, or $(Ar^1)$alkylSO$_2$;
$R^7$ is hydrogen, alkyl, or alkoxy;
$NR^6R^7$ together form azetdinyl, pyrrolidinyl, piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, $(Ar^3)$alkyl, and, $Ar^3$;
$R^8$ is adamantyl, hydroxyadamantyl, hydroxycycloalkyl, tetrahydrofuranyl, tetrahydropyranyl, pyrrolidinonyl alkoxy, alkylthio, phenoxy, or (phenyl)NH;
or $R^8$ is azetdinyl, pyrrolidinyl, piperidinyl, piperazinyl, morpholinyl, or tetrahydronapthalinyl, and is substituted with 0-1 substituents selected from alkyl, alkylCO, alkylCO$_2$, cycloalkylCO, cycloalkylCO$_2$, $(Ar^3)$alkyl, $Ar^3$, benzodioxolyl, piperidinyl morpholinyl, and (morpholinyl)ethyl;
$R^9$ is azetdinyl, pyrrolidinyl, piperidinyl, piperazinyl, or morpholinyl;
$R^{10}$ is hydrogen or alkyl;
$R^{11}$ is hydrogen or alkyl;
or $NR^{10}R^{11}$ is azetidinyl, pyrrolidinyl, piperidinyl, piperazinyl, or morpholinyl;
$Ar^1$ is phenyl, pyridinyl, furanyl, imidazolyl, thiazolyl, benzodioxolyl, or benzthiazolyl, and is substituted with 0-5 substituents selected from halo, hydroxy, alkoxy, cyano, alkyl, cycloalkyl, haloalkyl, haloalkoxy, phenoxy, $NR^{10}R^{11}$, $CONR^{10}R^{11}$, alkylSO$_2$, SO$_2$NR$^{10}$R$^{11}$, Ar$^3$SO$_2$, $(Ar^3)$alkylSO$_2$, $R^9$, and $Ar^4$;
$Ar^2$ is chromanyl substituted with 0-3 substituents selected from halo and alkyl;
$Ar^3$ is phenyl substituted with 0-3 substituents selected from halo, alkyl, and alkoxy; and
$Ar^4$ is phenyl, pyrimidinyl, pyrrolyl, or triazolyl, and is substituted with 0-1 alkyl substituents;
or a pharmaceutically acceptable salt thereof.

Another aspect of the invention is a compound of formula I where $R^6$ is $(Ar^1)$alkyl, or a pharmaceutically acceptable salt thereof.

Another aspect of the invention is a compound of formula I where $R^6$ is $(Ar^1)CH_2$, or a pharmaceutically acceptable salt thereof.

Another aspect of the invention is a compound of formula I where $Ar^1$ is phenyl or pyridinyl, and is substituted with 0-5 substituents selected from halo, hydroxy, alkoxy, cyano, alkyl, cycloalkyl, haloalkyl, haloalkoxy, phenoxy, $NR^{10}R^{11}$, $CONR^{10}R^{11}$, alkylSO$_2$, SO$_2$NR$^{10}$R$^{11}$, Ar$^3$SO$_2$, $(Ar^3)$alkylSO$_2$, $R^9$, and $Ar^4$, or a pharmaceutically acceptable salt thereof.

Another aspect of the invention is a compound of formula I where $(R^8)$alkyl, or a pharmaceutically acceptable salt thereof.

Another aspect of the invention is a compound of formula I where $NR^6R^7$ together form piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, $(Ar^3)$alkyl, and $Ar^3$, or a pharmaceutically acceptable salt thereof.

Another aspect of the invention is a compound of formula I where $Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido; or $Ar^2$ is

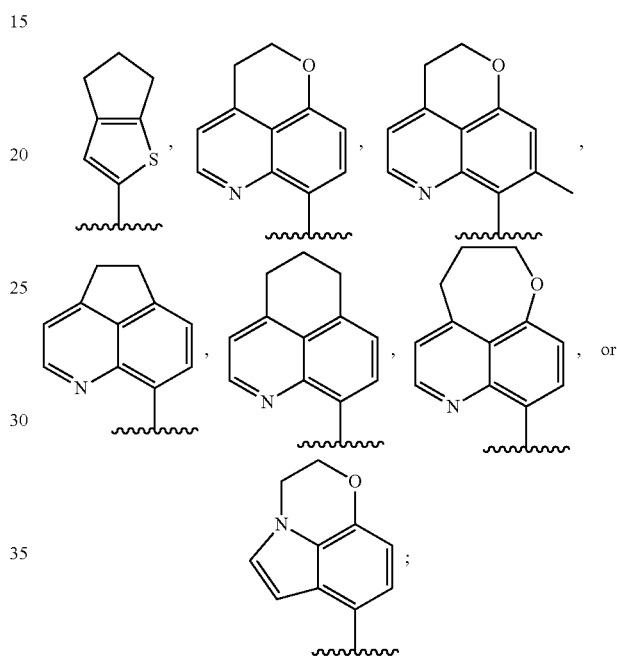

or a pharmaceutically acceptable salt thereof.

Another aspect of the invention is a compound of formula I where $Ar^2$ is chromanyl and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido, or a pharmaceutically acceptable salt thereof.

Another aspect of the invention is a compound of formula I where $Ar^2$ is chromanyl and is substituted with 0-3 substituents selected from halo and alkyl, or a pharmaceutically acceptable salt thereof.

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $Ar^1$, $Ar^2$, $Ar^3$, and $Ar^4$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Cycloalkenyl" means a monocyclic ring system composed of 4 to 7 carbons. "Halo" means fluoro, chloro, bromo, or iodo. "Haloalkyl" and "haloalkoxy"

include all halogenated isomers from monohalo to perhalo. "Aryl" includes carbocyclic and heterocyclic aromatic substituents. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1. Activity equal to A refers to a compound having an $EC_{50} \leq 100$ nM, while B and C denote compounds having an $EC_{50}$ between 100 nM and 1 uM (B) or >1 uM (C).

TABLE 1

| Example | Activity | $EC_{50}$ μM |
|---|---|---|
| 1 | A | 0.053 |
| 2 | C | |
| 3 | A | 0.032 |
| 4 | A | |
| 5 | A | |
| 6 | A | |
| 7 | A | |
| 8 | A | |
| 9 | B | |
| 10 | B | |
| 11 | B | |
| 12 | C | |
| 13 | C | 40.0 |
| 14 | C | |
| 15 | A | |
| 16 | A | |
| 17 | A | |
| 18 | B | 0.547 |
| 19 | A | |
| 20 | A | |
| 21 | A | |
| 22 | A | |
| 23 | A | |
| 24 | A | |
| 25 | A | |
| 26 | A | |
| 27 | A | |
| 28 | B | |
| 29 | A | |
| 30 | B | 3.20 |
| 31 | A | |
| 32 | A | |
| 33 | A | |
| 34 | A | |
| 35 | A | |
| 36 | B | 0.255 |
| 37 | C | 20.0 |
| 38 | B | 0.167 |
| 39 | A | |
| 40 | A | |
| 41 | B | |
| 42 | A | |
| 43 | B | |
| 44 | A | |
| 45 | A | |
| 46 | A | |
| 47 | B | 0.281 |
| 48 | A | |
| 49 | A | |
| 50 | A | |
| 51 | C | |
| 52 | A | |
| 53 | C | 3.19 |
| 54 | A | |

TABLE 1-continued

| Example | Activity | EC$_{50}$ μM |
|---|---|---|
| 55 | A | |
| 56 | A | |
| 57 | A | |
| 58 | C | |
| 59 | B | |
| 60 | A | |
| 61 | C | |
| 62 | A | 0.013 |
| 63 | A | |
| 64 | A | |
| 65 | A | |
| 66 | A | |
| 67 | A | 0.009 |
| 68 | A | |
| 69 | A | |
| 70 | A | |
| 71 | A | |
| 72 | B | 0.668 |
| 73 | A | |
| 74 | C | |
| 75 | C | |
| 76 | C | |
| 77 | B | |
| 78 | A | |
| 79 | A | |
| 80 | A | |
| 81 | A | |
| 82 | B | |
| 83 | C | |
| 84 | A | |
| 85 | A | 0.016 |
| 86 | A | |
| 87 | A | |
| 88 | C | |
| 89 | C | |
| 90 | B | |
| 91 | C | |
| 92 | B | |
| 93 | A | |
| 94 | B | |
| 95 | C | |
| 96 | A | 0.077 |
| 97 | C | |
| 98 | A | |
| 99 | A | |
| 100 | B | |
| 101 | B | |
| 102 | A | |
| 103 | B | 0.073 |
| 104 | C | |
| 105 | A | |
| 106 | C | |
| 107 | C | |
| 108 | A | 0.013 |
| 109 | A | |
| 110 | A | |
| 111 | A | |
| 112 | A | |
| 113 | A | |
| 114 | A | |
| 115 | A | |
| 116 | A | |
| 117 | A | |
| 118 | A | |
| 119 | A | |
| 120 | A | |
| 121 | B | |
| 122 | A | |
| 123 | A | |
| 124 | B | |
| 125 | A | |
| 126 | A | |
| 127 | B | |
| 128 | A | |
| 129 | B | |
| 130 | A | |
| 131 | A | |
| 132 | B | |
| 133 | B | 0.185 |
| 134 | C | |
| 135 | B | |
| 136 | A | |
| 137 | C | |
| 138 | A | |
| 139 | A | |
| 140 | A | |
| 141 | B | 0.114 |
| 142 | A | |
| 143 | A | 0.028 |
| 144 | B | 0.122 |
| 145 | A | |
| 146 | A | |
| 147 | A | |
| 148 | A | |
| 149 | C | |
| 150 | C | 1.2 |
| 151 | A | |
| 152 | A | 0.030 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions well known in the art. Intermediates I-3 can be prepared by procedure well known in the art or as set forth in the examples below using compound I-1 and compound I-2. Intermediates I-3 are conveniently transforde to intermediates I-5 via intermediates I-4 using conditions well-known to those skilled in the art. Intermediates I-5 are oxidized to intermediates I-6 by reactions well-known in the art, including but not limited to Davis oxidation. Intermediates I-6 are oxidized to intermediates I-7 by a well-known conditions, including but not limited to Dess-Martin oxidation. Intermediates I-7 are reduced to chiral intermediates I-8 using well-known conditions in the presence of catalytic chiral ligands. Intermediates I-8 are converted to the intermediates I-9 by well-known conditions, including but not limited to tertiary-butyl acetate and perchloric acid. Intermediates I-9 are conveniently transformed to intermediates I-10 using conditions well-known in the art, including but not limited to the Suzuki coupling between intermediates I-9 and R$_4$—B(OR)$_2$. The boronate or boronic acid coupling reagents, well-known in the art, are commercially available or are prepared by reactions well-known to those skilled in the art (PCT Appln. WO20090662285). The intermediates I-10 are regioselectively converted to intermediates I-11 by methods well-known in the art. Intermediates I-11 are conveniently converted to intermediates I-12 by conditions well-known to those skilled in the art, including but not limited to HATU and appropriate amine (R$_5$R$_6$NH) or converting carboxylic acid to acid chloride and coupling with appropriate amine (R$_5$R$_6$NH). Amines (R$_5$R$_6$NH) are commercially available or are prepared by reactions well-known in the art (PCT Appln. WO2005118593). Intermediates I-12 are transformed to intermediates I-13 using conditions well-known to those skilled in the art.

Scheme I.

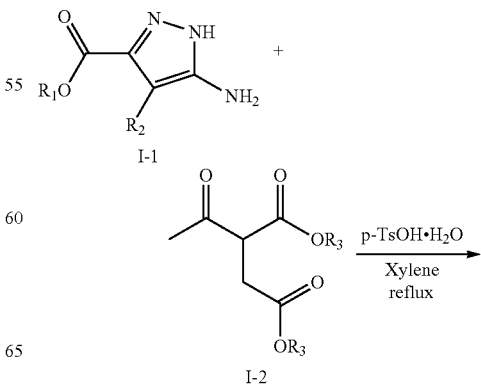

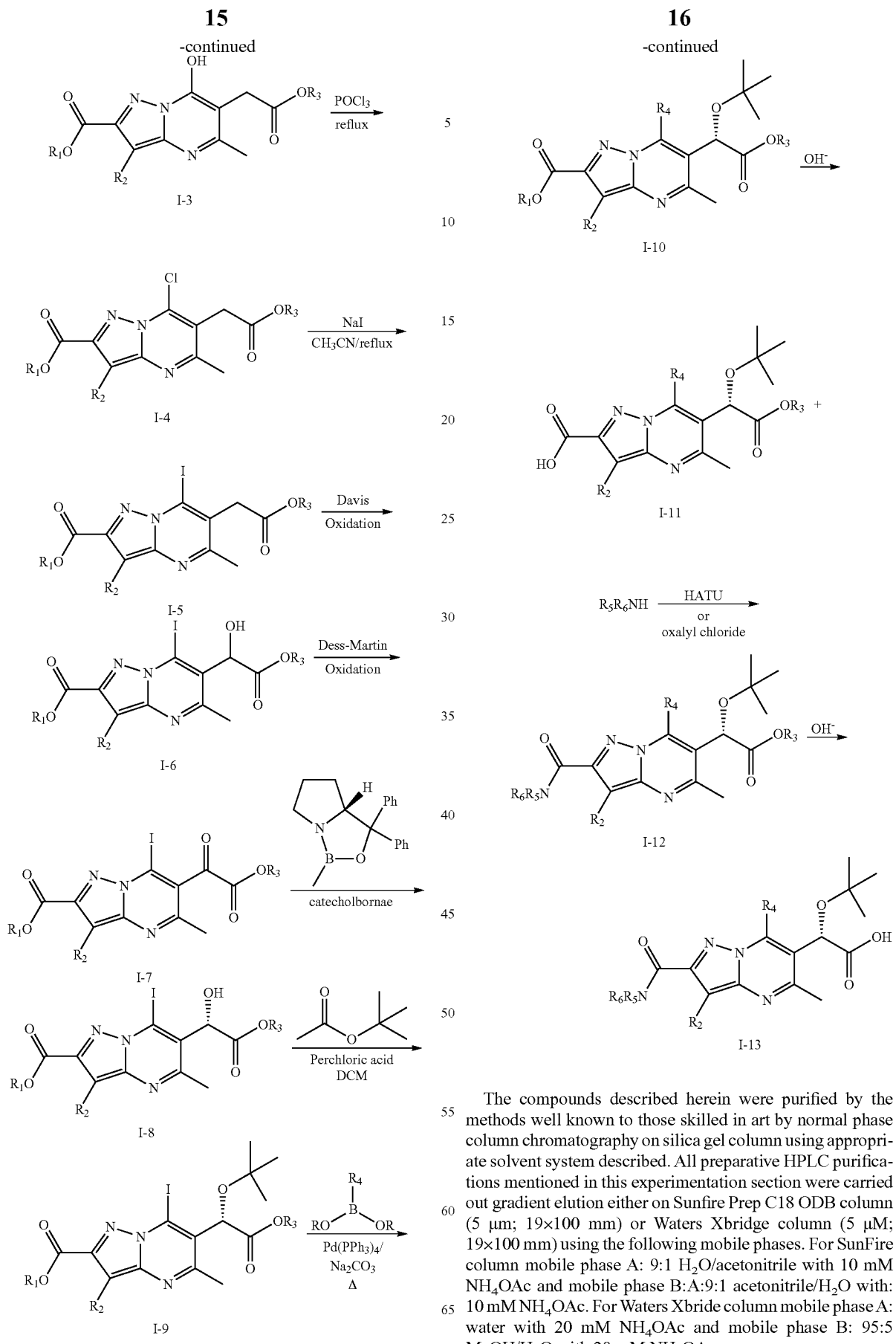

The compounds described herein were purified by the methods well known to those skilled in art by normal phase column chromatography on silica gel column using appropriate solvent system described. All preparative HPLC purifications mentioned in this experimentation section were carried out gradient elution either on Sunfire Prep C18 ODB column (5 μm; 19×100 mm) or Waters Xbridge column (5 μM; 19×100 mm) using the following mobile phases. For SunFire column mobile phase A: 9:1 $H_2O$/acetonitrile with 10 mM $NH_4OAc$ and mobile phase B:A:9:1 acetonitrile/$H_2O$ with: 10 mM $NH_4OAc$. For Waters Xbride column mobile phase A: water with 20 mM $NH_4OAc$ and mobile phase B: 95:5 MeOH/$H_2O$ with 20 mM $NH_4OAc$.

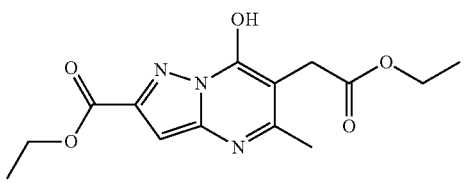 [SMILES: CCOC(=O)Cc1c(C)nc2cc(C(=O)OCC)nn2c1O]

Ethyl 6-(2-ethoxy-2-oxoethyl)-7-hydroxy-5-methylpyrazolo[1,5-a]pyrimidine-2-carboxylate A suspension of ethyl 5-amino-1H-pyrazole-3-carboxylate (35.5 g, 229 mmol, prepared according to WO 2008015271), diethyl 2-acetylsuccinate (51.2 mL, 275 mmol) and Ts-OH.H$_2$O (0.218 g, 1.144 mmol) in o-xylene (500 mL) was refluxed using Dean-Stork condensor for 5 h. (Note: The suspension turned clear homogeneous solution and then in about 15 min yellow solid started crashing out of the reaction). Then, the reaction mixture was cooled, diluted with hexanes (250 mL), filtered, washed with hexanes and dried to afford ethyl 6-(2-ethoxy-2-oxoethyl)-7-hydroxy-5-methylpyrazolo[1,5-a]pyrimidine-2-carboxylate (53 g, 75% yield) as light yellow solid. $^1$H NMR (500 MHz, DMSO-d$_6$) δ: 12.61 (br. s., 1H), 6.49 (s, 1H), 4.34 (q, J=7.1 Hz, 2H), 4.09 (q, J=7.1 Hz, 2H), 3.57 (s, 2H), 2.34 (s, 3H), 1.33 (t, J=7.2 Hz, 3H), 1.19 (t, J=7.0 Hz, 3H). LCMS (M+H)=308.04.

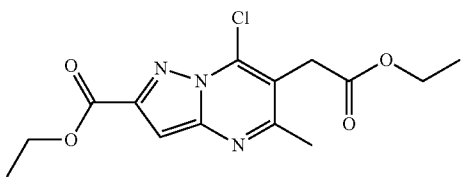

Ethyl 7-chloro-6-(2-ethoxy-2-oxoethyl)-5-methylpyrazolo[1,5-a]pyrimidine-2-carboxylate A mixture of ethyl 6-(2-ethoxy-2-oxoethyl)-7-hydroxy-5-methylpyrazolo[1,5-a]pyrimidine-2-carboxylate (25 g, 81 mmol), and N,N-dimethylaniline (20.62 mL, 163 mmol) in POCl$_3$ (100 mL) was heated at 120° C. for 3 h. Then, cooled, concentrated to half the volume and then poured into ice water and stirred for 20 min. Precipitates formed were filtered and solids were dissolved in ethyl acetate (1 L) and washed with water. Filterate was then extracted with ethyl acetate and combined organic layers were washed with brine (200 mL), dried (Na$_2$SO$_4$), filtered and concentrated. The crude was then triturated with EtOAc/hexane to afford ethyl 7-chloro-6-(2-ethoxy-2-oxoethyl)-5-methylpyrazolo[1,5-a]pyrimidine-2-carboxylate (22 g, 67.5 mmol, 83% yield) as light yellow solid. $^1$H NMR (500 MHz, CDCl$_3$) δ: 7.21 (s, 1H), 4.52 (q, J=7.2 Hz, 2H), 4.24 (q, J=7.2 Hz, 2H), 3.94 (s, 2H), 2.66 (s, 3H), 1.48 (t, J=7.0 Hz, 3H), 1.30 (t, J=7.2 Hz, 3H). LCMS (M+H)=326.2.

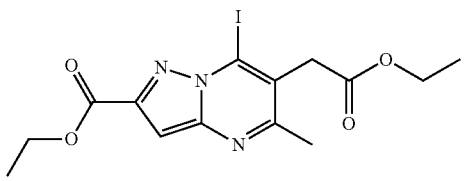 [SMILES: CCOC(=O)Cc1c(C)nc2cc(C(=O)OCC)nn2c1I]

Ethyl 6-(2-ethoxy-2-oxoethyl)-7-iodo-5-methylpyrazolo[1,5-a]pyrimidine-2-carboxylate Ethyl 7-chloro-6-(2-ethoxy-2-oxoethyl)-5-methylpyrazolo[1,5-a]pyrimidine-2-carboxylate (5 g, 15.35 mmol) and sodium iodide (9.20 g, 61.4 mmol) were suspended in acetonitrile (80 mL) and the resulting mixture was heated at 80° C. for 2 h. At this point LCMS indicated completion of reaction and appearance of the desired product. After cooling to rt, the reaction mixture was diluted with ethyl acetate and washed with water and aqueous Na$_2$S$_2$O$_3$, dried (Na$_2$SO$_4$), filtered and concentrated. Then crude product was triturated with ethyl acetate/hexane to afford ethyl 6-(2-ethoxy-2-oxoethyl)-7-iodo-5-methylpyrazolo[1,5-a]pyrimidine-2-carboxylate (5.7 g, 13.66 mmol, 89% yield) as off white solid. $^1$H NMR (500 MHz, CDCl$_3$) δ: 7.32 (s, 1H), 4.51 (d, J=7.0 Hz, 2H), 4.25 (d, J=7.0 Hz, 2H), 4.02 (s, 2H), 2.68 (s, 3H), 1.48 (t, J=7.2 Hz, 3H), 1.31 (t, J=7.2 Hz, 3H). LCMS (M+H)=418.2.

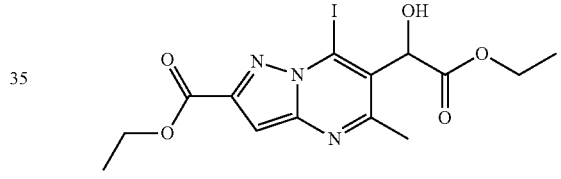

Ethyl 6-(2-ethoxy-1-hydroxy-2-oxoethyl)-7-iodo-5-methylpyrazolo[1,5-a]pyrimidine-2-carboxylate To a stirred solution of 0.9M KHMDS/THF (39.1 mL, 35.2 mmol) in THF (100 mL) at −78° C. was added a THF (50 mL) solution of ethyl 6-(2-ethoxy-2-oxoethyl)-7-iodo-5-methylpyrazolo[1,5-a]pyrimidine-2-carboxylate (11.3 g, 27.1 mmol) over 5 min. After 30 min, a THF (50 mL) solution of 3-phenyl-2-(phenylsulfonyl)-1,2-oxaziridine (9.20 g, 35.2 mmol) was added to the red reaction mixture and stirred for additional 30 min at −78° C. Then, the resulting orange reaction mixture was quenched with sat. NH$_4$Cl (50 mL), diluted with EtOAc (200 mL), washed with water (100 mL), brine (100 mL), dried (Na$_2$SO$_4$), filtered and concentrated to give solid. This solid was triturated with small amount of ethyl acetate and solids were filtered, washed with hexanes and dried under high vac to afford ethyl 6-(2-ethoxy-1-hydroxy-2-oxoethyl)-7-iodo-5-methylpyrazolo[1,5-a]pyrimidine-2-carboxylate (7.3 g, 16.85 mmol, 62.2% yield) as light yellow solid. $^1$H NMR (500 MHz, CDCl$_3$) δ: 7.33 (s, 1H), 5.75 (d, J=2.1 Hz, 1H), 4.52 (qd, J=7.1, 1.2 Hz, 2H), 4.37-4.30 (m, 2H), 3.57 (d, J=2.4 Hz, 1H), 2.63 (s, 3H), 1.48 (t, J=7.2 Hz, 3H), 1.27 (t, J=7.0 Hz, 3H). LCMS (M+H)=434.1.

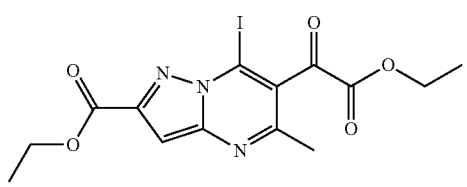 [SMILES: CCOC(=O)C(=O)c1c(C)nc2cc(C(=O)OCC)nn2c1I]

Ethyl 6-(2-ethoxy-2-oxoacetyl)-7-iodo-5-methylpyrazolo[1,5-a]pyrimidine-2-carboxylate To a mixture of ethyl 6-(2-ethoxy-1-hydroxy-2-oxoethyl)-7-iodo-5-methylpyrazolo[1,5-a]pyrimidine-2-carboxylate (3.7 g, 6.41 mmol) in CH$_2$Cl$_2$ (80 mL) was added Dess-Martin Periodinane (2.72 g, 6.41 mmol) and the resulting mixture was stirred at rt for 1 hr. Then diluted with ethyl acetate (500 mL) and washed with sat. NaHCO$_3$ solution (100 mL), dried (Na$_2$SO$_4$), filtered, concentrated and the residue was purified by silica gel chromatography (5-70% EtOAc/hexane) to afford desired ethyl 6-(2-ethoxy-2-oxoacetyl)-7-iodo-5-methylpyrazolo[1,5-a]pyrimidine-2-carboxylate (2.5 g, 5.80 mmol, 91% yield) as off-white solid. $^1$H NMR (400 MHz, CDCl$_3$) δ: 7.36 (s, 1H), 4.50 (dq, J=14.5, 7.1 Hz, 4H), 2.56 (s, 3H), 1.46 (t, J=7.2 Hz, 3H), 1.48 (t, J=7.2 Hz, 3H). LCMS (M+H)=431.87.

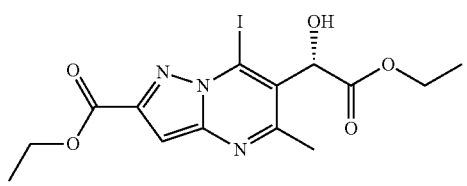 [SMILES: CCOC(=O)c1cc2nc(C)c([C@H](O)C(=O)OCC)c(I)n2n1]

(S)-Ethyl 6-(2-ethoxy-1-hydroxy-2-oxoethyl)-7-iodo-5-methylpyrazolo[1,5-a]pyrimidine-2-carboxylate To a stirred yellow solution of ethyl 6-(2-ethoxy-2-oxoacetyl)-7-iodo-5-methylpyrazolo[1,5-a]pyrimidine-2-carboxylate (6.4 g, 14.84 mmol) in anhydrous toluene (300 mL) was added 1.1M (R)-1-methyl-3,3-diphenylhexahydropyrrolo[1,2-c][1,3,2]oxazaborole/toluene (5.40 mL, 5.94 mmol). The mixture was cooled to −35° C. and a solution of 50% catechoborane/toluene (5.09 mL, 20.78 mmol) was added over 10 min. After 30 min, the reaction mixture was slowly warmed to −15° C. and stirred for additional 2 h, then diluted with EtOAc (600 mL) and sat. Na$_2$CO$_3$ (100 mL). The mixture was stirred vigorously for 30 min, and the organic phase washed with sat Na$_2$CO$_3$ (2×100 mL), dried (Na$_2$SO$_4$), filtered, concentrated and the residue was purified by silica gel chromatography (5-100% EtOAc/hexane) to afford desired (S)-ethyl 6-(2-ethoxy-1-hydroxy-2-oxoethyl)-7-iodo-5-methylpyrazolo[1,5-a]pyrimidine-2-carboxylate (5.3 g, 12.23 mmol, 82% yield) as off-white solid. $^1$H NMR (500 MHz, CDCl$_3$) δ: 7.33 (s, 1H), 5.75 (d, J=2.4 Hz, 1H), 4.52 (qd, J=7.1, 1.1 Hz, 2H), 4.38-4.29 (m, 2H), 3.59 (d, J=2.4 Hz, 1H), 2.63 (s, 3H), 1.48 (t, J=7.2 Hz, 3H), 1.27 (t, J=7.2 Hz, 3H). LCMS (M+H)=434.2.

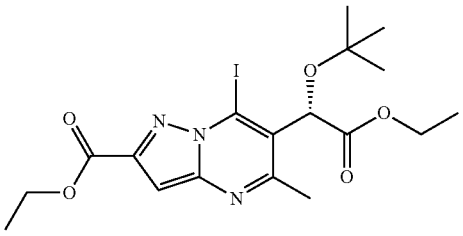 [SMILES: CCOC(=O)c1cc2nc(C)c([C@H](OC(C)(C)C)C(=O)OCC)c(I)n2n1]

(S)-Ethyl 6-(1-(tert-butoxy)-2-ethoxy-2-oxoethyl)-7-iodo-5-methylpyrazolo[1,5-a]pyrimidine-2-carboxylate To a stirred solution of (S)-ethyl 6-(2-ethoxy-1-hydroxy-2-oxoethyl)-7-iodo-5-methylpyrazolo[1,5-a]pyrimidine-2-carboxylate (5.3 g, 12.23 mmol) in CH$_2$Cl$_2$ (150 mL) and t-butyl acetate (105 mL) was added perchloric acid (3.15 mL, 36.7 mmol) at rt and sealed the reaction flask. After 3 h, the reaction mixture was diluted with CH$_2$Cl$_2$ (100 mL), carefully quenched with sat. NaHCO$_3$ (50 mL), organic layer separated and washed with brine (100 mL), dried (Na$_2$SO$_4$), filtered and concentrated to give yellow liquid. This was purified by flash column chromatography on silica gel column using (10-50% EtOAc/Hex as eluant) to afford the desired (S)-ethyl 6-(1-(tert-butoxy)-2-ethoxy-2-oxoethyl)-7-iodo-5-methylpyrazolo[1,5-a]pyrimidine-2-carboxylate (4.5 g, 8.28 mmol, 67.7% yield) as viscous oil. 700 mg of starting material was also recovered. $^1$H NMR (500 MHz, CDCl$_3$) δ: 7.31 (s, 1H), 5.56 (s, 1H), 4.51 (q, J=7.1 Hz, 2H), 4.26-4.16 (m, 2H), 2.71 (s, 3H), 1.48 (t, J=7.2 Hz, 3H), 1.30 (s, 9H), 1.23 (t, J=7.0 Hz, 3H). LCMS (M+H)=490.0.

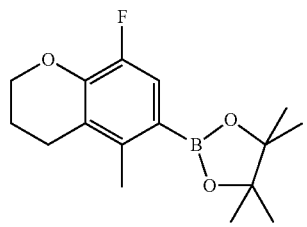 [SMILES: Cc1c(B2OC(C)(C)C(C)(C)O2)cc(F)c2c1CCCO2]

2-(8-fluoro-5-methylchroman-6-yl)-4,4,5,5-tetramethyl-1,3,2 dioxaborolane

The title compound was prepared from the known procedure as described in the reference WO 2009/062285.

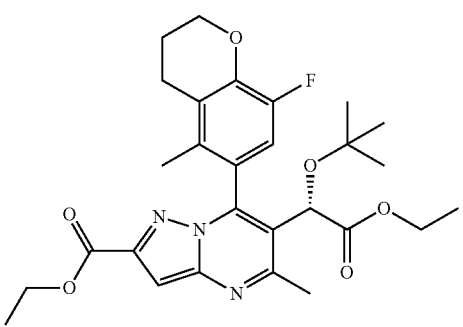 [SMILES: CCOC(=O)c1cc2nc(C)c([C@H](OC(C)(C)C)C(=O)OCC)c(-c3cc(F)c4c(c3C)CCCO4)n2n1]

6-((S)-1-(tert-Butoxy)-2-ethoxy-2-oxoethyl)-7-(8-fluoro-5-methylchroman-6-yl)-5-methylpyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (4.5 g, 9.20 mmol), 2-(8-fluoro-5-methylchroman-6-yl)-4,4,5,5-tetramethyl-1,3,2-dioxaborolane (3.22 g, 11.04 mmol) and 2N $Na_2CO_3$ (9.20 mL, 18.39 mmol) in DMF (100 mL) was degassed for 30 min. Tetrakis(triphenylphosphine)palladium(0) (0.744 g, 0.644 mmol) was then added and the degassing was continued for another 15 min. The mixture was then heated at 100° C. for 16 h. At this point LCMS indicated completion of reaction and appearance of desired product. After cooling to rt, water was added (50 mL) and the mixture was extracted with ether (2×200 mL), washed with brine (100 mL), dried ($Na_2SO_4$), filtered and concentrated. The crude was then purified by silica gel chromatography (5-60% EtOAc/hexane) to afford ethyl 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylate (4 g, 7.58 mmol, 82% yield) as mixture of atrope isomers (approx 10% of minor atrope isomer was present). $^1$H NMR (500 MHz, $CDCl_3$) δ: 7.10 (s, 1H), 6.87 (d, J=10.7 Hz, 1H), 5.00 (s, 1H), 4.41 (qd, J=7.1, 3.1 Hz, 2H), 4.35 (dd, J=5.2, 4.0 Hz, 2H), 4.14 (q, J=7.2 Hz, 2H), 2.80 (s, 3H), 2.79-2.73 (m, 2H), 2.23-2.15 (m, 2H), 1.82 (s, 3H), 1.41 (t, J=7.2 Hz, 3H), 1.22-1.19 (m, 4H), 1.18 (s, 9H). LCMS (M+H)=528.4.

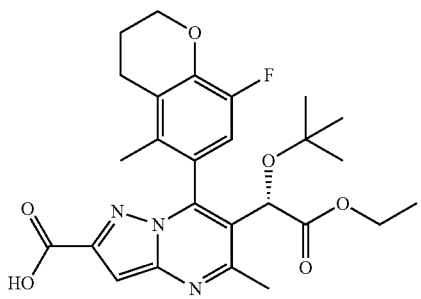 [SMILES: CCOC(=O)[C@@H](OC(C)(C)C)c1c(C)nc2cc(C(=O)O)nn2c1-c1cc(F)c2c(c1C)CCCO2]

6-((S)-1-(tert-Butoxy)-2-ethoxy-2-oxoethyl)-7-(8-fluoro-5-methylchroman-6-yl)-5-methylpyrazolo[1,5-a]pyrimidine-2-carboxylic acid To a solution of ethyl 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylate (4 g, 6.07 mmol) in THF (40 mL) was added 1N NaOH (6.07 mL, 6.07 mmol) and the resulting mixture was stirred at rt for 16 h. At this point LCMS indicated about 70% conversion, so additional NaOH (2.5 mL, 2.5 mmol) was added and the mixture was stirred for another 2 h. At this point LCMS indicated progression of reaction (approx 90% coversion) along with small amount of di-acid. Water (20 mL) was then added and the mixture was acidified with 1N HCl (10 mL) and extracted with ether (2×100 mL), washed with brine (50 mL), dried ($Na_2SO_4$), filtered and concentrated to afford 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (2.7 g, 5.41 mmol, 89% yield) as off-white solid. $^1$H NMR (500 MHz, $CDCl_3$) δ: 7.21 (s, 1H), 6.85 (d, J=10.7 Hz, 1H), 5.00 (s, 1H), 4.36 (t, J=4.4 Hz, 2H), 4.19-4.12 (m, 2H), 2.81 (s, 3H), 2.80-2.74 (m, 2H), 2.20 (dd, J=6.3, 4.1 Hz, 2H), 1.83 (s, 3H), 1.24-1.20 (m, 3H), 1.18 (s, 9H). LCMS (M+H)=500.4.

Preparation of Examples

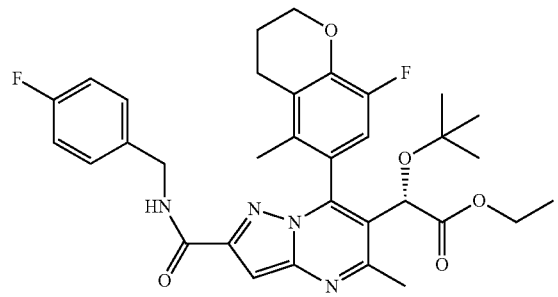 [SMILES: CCOC(=O)[C@@H](OC(C)(C)C)c1c(C)nc2cc(C(=O)NCc3ccc(F)cc3)nn2c1-c1cc(F)c2c(c1C)CCCO2]

Procedure A: (2S)-Ethyl 2-(tert-butoxy)-2-(7-(8-fluoro-5-methylchroman-6-yl)-2-((4-fluorobenzyl)carbamoyl)-5-methylpyrazolo[1,5-a]pyrimidin-6-yl)acetate To a mixture of 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (21 mg, 0.042 mmol) and (4-fluorophenyl)methanamine (10.52 mg, 0.084 mmol) in DMF (1 mL) was added DIEA (0.037 mL, 0.210 mmol), HATU (32.0 mg, 0.084 mmol) and DMAP (1.027 mg, 8.41 μmol) and the resulting mixture was stirred at rt for 16 h. At this point LCMS indicated completion of reaction. The reaction mixture was then filtered and purified by prep HPLC to afford (2S)-ethyl 2-(tert-butoxy)-2-(7-(8-fluoro-5-methylchroman-6-yl)-2-((4-fluorobenzyl)carbamoyl)-5-methylpyrazolo[1,5-a]pyrimidin-6-yl)acetate (12 mg, 0.020 mmol, 47.1% yield) as off-white solid. $^1$H NMR (500 MHz, $CDCl_3$) δ: 7.34-7.30 (m, 2H), 7.23 (t, J=6.4 Hz, 1H), 7.20 (s, 1H), 7.06-6.99 (m, 2H), 6.85 (d, J=10.7 Hz, 1H), 4.96 (s, 1H), 4.67-4.53 (m, 2H), 4.35 (t, J=5.3 Hz, 2H), 4.15 (q, J=7.0 Hz, 2H), 2.79 (s, 3H), 2.76 (t, J=6.6 Hz, 2H), 2.24-2.14 (m, 2H), 1.82 (s, 3H), 1.21 (t, J=7.2 Hz, 3H), 1.17 (s, 9H). LCMS (M+H)=607.4.

Example 1

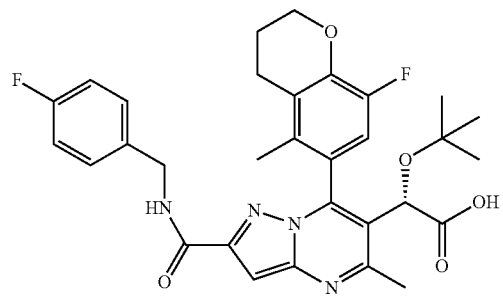 [SMILES: Cc1nc2cc(C(=O)NCc3ccc(F)cc3)nn2c(-c2cc(F)c3c(c2C)CCCO3)c1[C@H](OC(C)(C)C)C(=O)O]

A solution of (2S)-ethyl 2-(tert-butoxy)-2-(7-(8-fluoro-5-methylchroman-6-yl)-2-((4-fluorobenzyl)carbamoyl)-5-methylpyrazolo[1,5-a]pyrimidin-6-yl)acetate (12 mg, 0.020 mmol) and 1M NaOH (0.079 mL, 0.079 mmol) in MeOH (1 mL) was heated at 60° C. for 16 h. Then, the reaction mixture was cooled and purified by prep HPLC to afford (2S)-2-(tert-butoxy)-2-(7-(8-fluoro-5-methylchroman-6-yl)-2-((4-fluorobenzyl)carbamoyl)-5-methylpyrazolo[1,5-a]pyrimidin-6-yl)acetic acid (8 mg, 0.013 mmol, 66.4% yield) as white solid. $^1$H NMR (500 MHz, CHLOROFORM-d) δ: 7.31 (dd, J=8.5, 5.5 Hz, 2H), 7.26 (t, J=6.4 Hz, 1H), 7.21 (s, 1H), 7.05-6.99 (m, 2H), 6.87 (d, J=10.7 Hz, 1H), 5.02 (s, 1H), 4.60 (d, J=6.4 Hz, 2H), 4.35-4.32 (m, 2H), 2.77 (s, 3H), 2.76-2.71 (m, 2H), 2.20-2.14 (m, 2H), 1.85 (s, 3H), 1.19 (s, 9H). LCMS (M+H)= 579.4.

Example 2

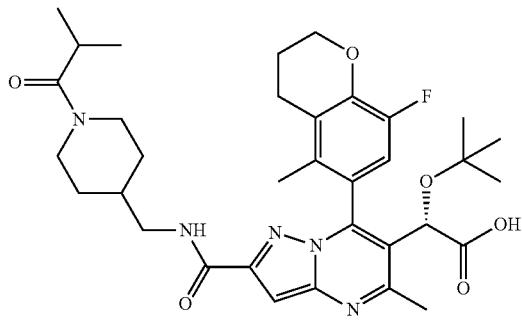 [SMILES: Cc1nc2cc(C(=O)NCC3CCN(C(=O)C(C)C)CC3)nn2c(-c2cc(F)c3c(c2C)CCCO3)c1[C@H](OC(C)(C)C)C(=O)O]

Procedure B: (2S)-2-(tert-Butoxy)-2-(7-(8-fluoro-5-methylchroman-6-yl)-2-(((1-isobutyrylpiperidin-4-yl)methyl)carbamoyl)-5-methylpyrazolo[1,5-a]pyrimidin-6-yl)acetic acid To a solution of 6-((S)-1-(tert-butoxy)-2-ethoxy-2-oxoethyl)-7-(8-fluoro-5-methylchroman-6-yl)-5-methylpyrazolo[1,5-a]pyrimidine-2-carboxylic acid (40 mg, 0.080 mmol) in CH$_2$Cl$_2$ (1 mL) was added OXALYL CHLORIDE (10.51 μl, 0.120 mmol) 1 drop of DMF was then added and the mixture was stirred at room temp for 2 h. The crude acid chloride was then added to a pre-stirred solution of 1-(4-(aminomethyl)piperidin-1-yl)-2-methylpropan-1-one (29.5 mg, 0.160 mmol) and TEA (0.067 mL, 0.480 mmol) in CH2Cl2 (1.000 mL) and the resulting solution was stirred at room temperature for 2 h. At this point LCMS indicates completion of reaction. Mixture was then concentrated and purified by prep HPLC to afford desired ester, which was treated with 1N NaOH (0.160 mL, 0.160 mmol) in MeOH (1.500 mL) at 60° C. for 3 h. Mixture was then cooled and purified by prep HPLC to afford (2S)-2-(tert-butoxy)-2-(7-(8-fluoro-5-methylchroman-6-yl)-2-(1-isobutyrylpiperidin-4-yl)methyl)carbamoyl)-5-methylpyrazolo[1,5-a]pyrimidin-6-yl)acetic acid (9 mg, 0.013 mmol, 16.74% yield) as white solid. $^1$H NMR (500 MHz, CDCl$_3$) δ: 7.17 (s, 1H), 7.06-6.97 (m, 1H), 6.90 (d, J=10.7 Hz, 1H), 5.05 (s, 1H), 4.65 (d, J=12.2 Hz, 1H), 4.42-4.32 (m, 2H), 3.95 (d, J=14.6 Hz, 1H), 3.49-3.39 (m, 1H), 3.29-3.18 (m, 1H), 3.01 (t, J=12.1 Hz, 2H), 2.87-2.80 (m, 3H), 2.54 (t, J=12.7 Hz, 1H), 2.26-2.16 (m, 2H), 1.88 (s, 3H), 1.82 (d, J=13.4 Hz, 1H), 1.73 (d, J=13.1 Hz, 1H), 1.21 (s, 9H), 1.15-1.08 (m, 6H). LCMS (M+H)=638.6.

The following compounds listed in Table 2 were prepared according to the procedures described above for Examples 1 and 2.

Example 3

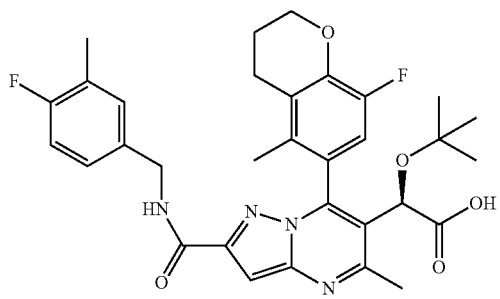 [SMILES: Cc1cc(CNC(=O)c2cc3nc(C)c([C@@H](OC(C)(C)C)C(=O)O)c(-c4cc(F)c5c(c4C)CCCO5)n3n2)ccc1F]

(2S)-2-(tert-Butoxy)-2-(2-((4-fluoro-3-methylbenzyl)carbamoyl)-7-(8-fluoro-5-methylchroman-6-yl)-5-methylpyrazolo[1,5-a]pyrimidin-6-yl)acetic acid. $^1$H NMR (500 MHz, CDCl$_3$) δ: 7.23 (t, J=6.6 Hz, 1H), 7.21 (s, 1H), 7.16 (d, J=7.3 Hz, 1H), 7.11 (d, J=4.9 Hz, 1H), 6.96 (t, J=9.0 Hz, 1H), 6.87 (d, J=10.7 Hz, 1H), 5.02 (s, 1H), 4.56 (d, J=6.4 Hz, 2H), 4.34 (t, J=4.3 Hz, 2H), 2.76 (s, 3H), 2.76-2.68 (m, 2H), 2.26 (s, 3H), 2.20-2.14 (m, 2H), 1.86 (s, 3H), 1.19 (s, 9H). LCMS (M+H)=593.4.

Example 4

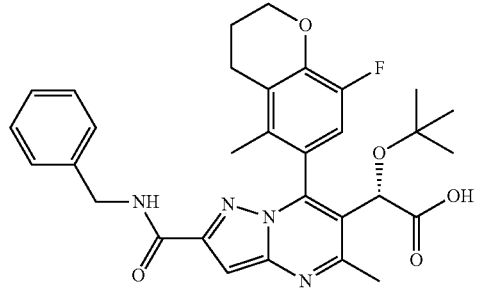 [SMILES: Cc1nc2cc(C(=O)NCc3ccccc3)nn2c(-c2cc(F)c3c(c2C)CCCO3)c1[C@H](OC(C)(C)C)C(=O)O]

(2S)-2-(2-(Benzylcarbamoyl)-7-(8-fluoro-5-methylchroman-6-yl)-5-methylpyrazolo[1,5-a]pyrimidin-6-yl)-2-(tert-butoxy)acetic acid. $^1$H NMR (500 MHz, CDCl$_3$) δ: 7.37-7.32 (m, 4H), 7.29-7.25 (m, 2H), 7.22 (s, 1H), 6.87 (d, J=10.7 Hz, 1H), 5.03 (s, 1H), 4.70-4.60 (m, 2H), 4.37-4.30 (m, 2H), 2.76 (s, 3H), 2.74 (t, J=6.6 Hz, 2H), 1.86 (s, 3H), 1.20 (s, 9H). LCMS (M+H)=561.14.

Example 5

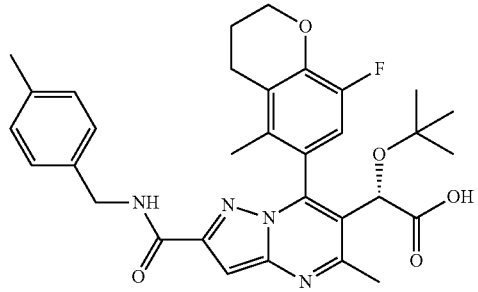 [SMILES: Cc1ccc(CNC(=O)c2cc3nc(C)c([C@H](OC(C)(C)C)C(=O)O)c(-c4cc(F)c5c(c4C)CCCO5)n3n2)cc1]

(2S)-2-(tert-butoxy)-2-(7-(8-fluoro-5-methylchroman-6-yl)-5-methyl-2-((4-methylbenzyl)carbamoyl)pyrazolo[1,5-a]pyrimidin-6-yl)acetic acid ¹H NMR (500 MHz, METHANOL-d₄) δ: 7.21-7.17 (m, J=7.9 Hz, 2H), 7.15-7.10 (m, 2H), 7.03 (s, 1H), 6.96 (d, J=11.0 Hz, 1H), 4.83 (s, 1H), 4.48 (s, 2H), 4.27 (t, J=5.2 Hz, 2H), 3.38 (s, 3H), 2.85 (s, 3H), 2.83-2.70 (m, 2H), 2.31 (s, 3H), 2.17-2.10 (m, 2H), 1.93 (s, 3H), 1.15 (s, 9H). LCMS (M+H)=575.21.

Example 6

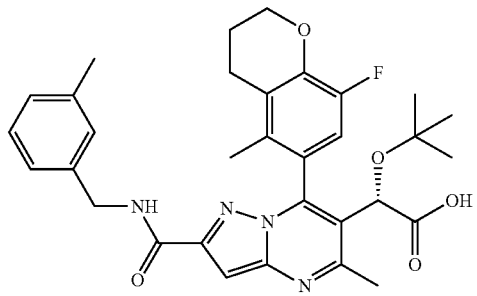 [SMILES: Cc1cccc(CNC(=O)c2cc3nc(C)c([C@H](OC(C)(C)C)C(=O)O)c(-c4cc(F)c5c(c4C)CCCO5)n3n2)c1]

(2S)-2-(tert-butoxy)-2-(7-(8-fluoro-5-methylchroman-6-yl)-5-methyl-2-β-methylbenzyl)carbamoyl)pyrazolo[1,5-a]pyrimidin-6-yl)acetic acid ¹H NMR (400 MHz, CDCl₃) δ: 7.26-7.18 (m, 3H), 7.17-7.08 (m, 3H), 6.87 (d, J=10.5 Hz, 1H), 5.32 (s, 1H), 4.61 (dd, J=9.3, 6.3 Hz, 2H), 4.37-4.28 (m, 2H), 2.75 (s, 3H), 2.74-2.70 (m, 2H), 2.35 (s, 3H), 2.21-2.13 (m, 2H), 1.88 (s, 3H), 1.21 (s, 9H). LCMS (M+H)=575.19.

Example 7

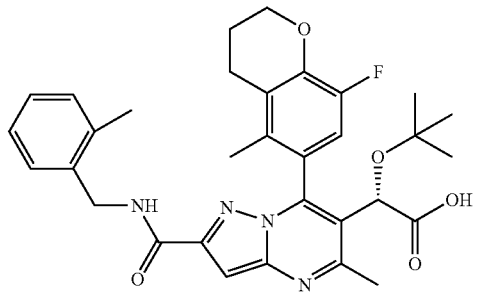 [SMILES: Cc1ccccc1CNC(=O)c1cc2nc(C)c([C@H](OC(C)(C)C)C(=O)O)c(-c3cc(F)c4c(c3C)CCCO4)n2n1]

(2S)-2-(tert-butoxy)-2-(7-(8-fluoro-5-methylchroman-6-yl)-5-methyl-2-((2-methylbenzyl)carbamoyl)pyrazolo[1,5-a]pyrimidin-6-yl)acetic acid ¹H NMR (500 MHz, METHANOL-d₄) δ: 7.23 (d, J=6.4 Hz, 1H), 7.18-7.11 (m, 3H), 7.04 (s, 1H), 6.97 (d, J=10.7 Hz, 1H), 4.83 (s, 1H), 4.54 (s, 2H), 4.27 (t, J=5.2 Hz, 2H), 2.86 (s, 3H), 2.83-2.68 (m, 2H), 2.33 (s, 3H), 2.18-2.06 (m, 2H), 1.93 (s, 3H), 1.15 (s, 9H). LCMS (M+H)=575.4.

Example 8

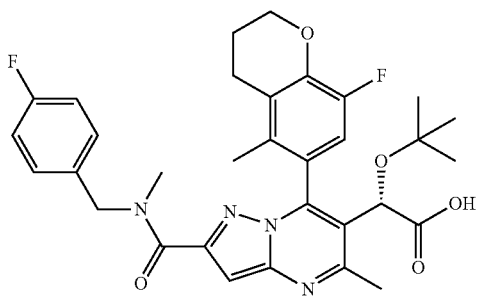 [SMILES: Cc1nc2cc(C(=O)N(C)Cc3ccc(F)cc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-((4-fluorobenzyl)(methyl)carbamoyl)-5-methylpyrazolo[1,5-a]pyrimidin-6-yl)acetic acid ¹H NMR (500 MHz, METHANOL-d₄) δ: 7.40-7.37 (m, 0.4H), 7.26 (dd, J=8.5, 5.5 Hz, 1.6H), 7.10-7.07 (m, 0.4H), 6.98-6.93 (m, 1.6H), 6.92 (s, 1H), 6.90-6.85 (m, 1H), 4.89 (s, 1H), 4.71 (s, 0.4H), 4.60 (s, 1.6H), 4.29-4.27 (m, 0.4H), 4.23-4.18 (m, 1.6H), 3.04 (s, 0.6H), 2.92 (s, 2.4H), 2.85 (s, 3H), 2.80-2.74 (m, 0.3H), 2.68-2.62 (m, 0.7H), 2.34-2.62 (m, 0.7H), 2.24-2.12 (m, 0.3H), 2.04-2.01 (m, 2H), 1.99 (s, 3H), 1.93 (s, 0.6H), 1.76 (s, 2.4H), 1.17 (s, 9H). LCMS (M+H)=593.4.

Example 9

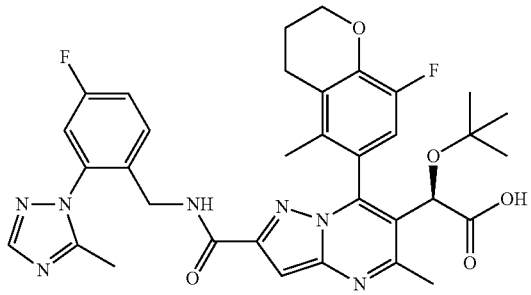 [SMILES: Cc1nc2cc(C(=O)NCc3ccc(F)cc3-n3ncnc3C)nn2c(-c2cc(F)c3c(c2C)CCCO3)c1[C@@H](OC(C)(C)C)C(=O)O]

(2S)-2-(tert-butoxy)-2-(2-((4-fluoro-2-(5-methyl-1H-1,2,4-triazol-1-yl)benzyl)carbamoyl)-7-(8-fluoro-5-methylchroman-6-yl)-5-methylpyrazolo[1,5-a]pyrimidin-6-yl)acetic acid ¹H NMR (500 MHz, DMSO-d₆) δ: 8.54 (t, J=6.1 Hz, 1H), 8.00 (s, 1H), 7.56-7.49 (m, 2H), 7.46-7.39 (m, 1H), 7.09 (d, J=11.3 Hz, 1H), 6.99 (s, 1H), 4.80 (s, 1H), 4.26 (t, J=5.0 Hz, 2H), 4.11 (d, J=6.1 Hz, 2H), 2.72 (t, J=7.0 Hz, 2H), 2.70 (s, 3H), 2.31 (s, 3H), 2.13-1.99 (m, 2H), 1.78 (s, 3H), 1.07 (s, 9H). LCMS (M+H)=660.4.

Example 10

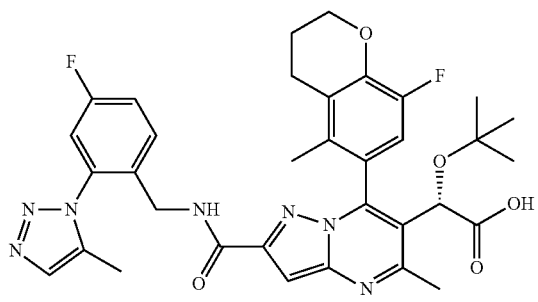 [SMILES: Cc1nc2cc(C(=O)NCc3ccc(F)cc3-n3nncc3C)nn2c(-c2cc(F)c3c(c2C)CCCO3)c1[C@H](OC(C)(C)C)C(=O)O]

(2S)-2-(tert-butoxy)-2-(2-((4-fluoro-2-(5-methyl-1H-1,2,3-triazol-1-yl)benzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.51 (t, J=6.0 Hz, 1H), 7.70 (d, J=0.9 Hz, 1H), 7.55 (dd, J=8.5, 6.1 Hz, 1H), 7.52-7.47 (m, 2H), 7.06 (d, J=11.0 Hz, 1H), 6.98 (s, 1H), 4.73 (br. s., 1H), 4.26 (t, J=5.2 Hz, 2H), 4.02 (d, J=5.8 Hz, 2H), 2.74-2.71 (m, 2H), 2.70 (s, 3H), 2.22-2.18 (m, 3H), 2.06 (d, J=5.2 Hz, 2H), 1.81-1.76 (m, 3H), 1.06 (s, 9H). LCMS (M+H)=660.4.

Example 11

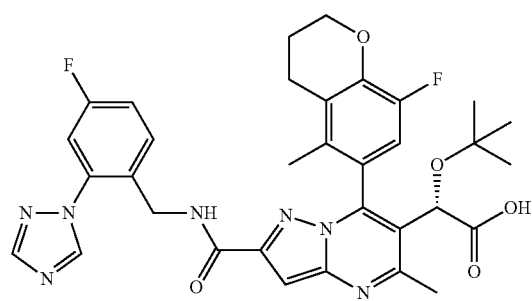 [SMILES: Cc1nc2cc(C(=O)NCc3ccc(F)cc3-n3cncn3)nn2c(-c2cc(F)c3c(c2C)CCCO3)c1[C@H](OC(C)(C)C)C(=O)O]

(2S)-2-(tert-butoxy)-2-(2-((4-fluoro-2-(1H-1,2,4-triazol-1-yl)benzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 9.01 (s, 1H), 8.62 (t, J=6.1 Hz, 1H), 8.19 (s, 1H), 7.55-7.49 (m, 2H), 7.40 (td, J=8.5, 2.4 Hz, 1H), 7.06 (d, J=11.3 Hz, 1H), 6.98 (s, 1H), 4.71 (br. s., 1H), 4.37-4.33 (m, 2H), 4.26 (t, J=5.2 Hz, 2H), 2.74-

2.71 (m, 2H), 2.70 (s, 3H), 2.11-1.99 (m, 2H), 1.79 (s, 3H), 1.06 (s, 9H). LCMS (M+H)=646.4.

Example 12

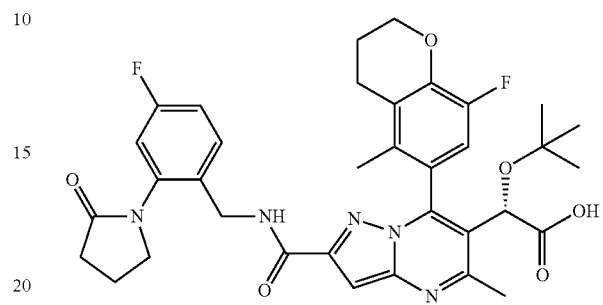

(2S)-2-(tert-butoxy)-2-(2-((4-fluoro-2-(2-oxopyrrolidin-1-yl)benzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.50 (t, J=6.1 Hz, 1H), 7.37 (dd, J=8.7, 6.6 Hz, 1H), 7.22 (dd, J=9.8, 2.7 Hz, 1H), 7.15 (td, J=8.5, 2.7 Hz, 1H), 7.05 (d, J=11.6 Hz, 1H), 7.00 (s, 1H), 4.77 (br. s., 1H), 4.29 (d, J=6.1 Hz, 2H), 4.25 (t, J=5.0 Hz, 2H), 3.73-3.69 (m, 2H), 2.74-2.71 (m, 2H), 2.70 (s, 3H), 2.41 (t, J=7.9 Hz, 2H), 2.09-2.03 (m, 4H), 1.78 (s, 3H), 1.07 (s, 9H). LCMS (M+H)=662.4.

Example 13

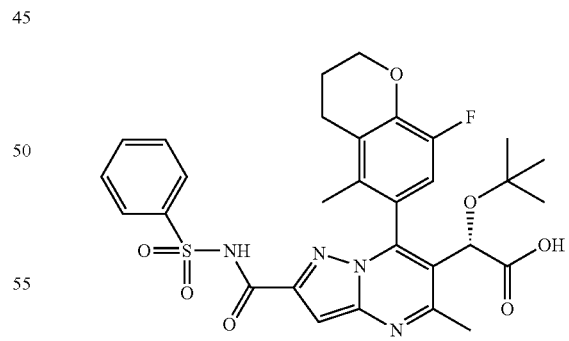

(2S)-2-(tert-butoxy)-2-(7-(8-fluoro-5-methylchroman-6-yl)-5-methyl-2-((phenylsulfonyl)carbamoyl)pyrazolo[1,5-a]pyrimidin-6-yl)acetic acid $^1$H NMR (500 MHz, DMSO-d$_6$) δ: 7.97 (s, 1H), 7.94 (d, J=7.6 Hz, 2H), 7.62 (br. s., 1H), 7.56 (br. s., 2H), 7.09 (br. s., 1H), 7.04 (d, J=11.0 Hz, 1H), 4.81 (s, 1H), 4.31-4.23 (m, 2H), 2.73-2.70 (m, 2H), 2.68 (s, 3H), 2.11-1.99 (m, 2H), 1.74 (s, 3H), 1.07 (s, 9H). LCMS (M+H)=611.3.

Example 14

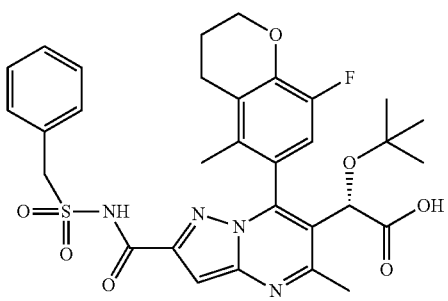 [SMILES: Cc1nc2cc(C(=O)NS(=O)(=O)Cc3ccccc3)nn2c(-c2cc(F)c3c(c2C)CCCO3)c1[C@H](OC(C)(C)C)C(=O)O]

(2S)-2-(2-((benzylsulfonyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-d$_6$) δ: 7.97 (s, 1H), 7.39-7.26 (m, 5H), 7.07 (s, 1H), 7.10 (s, 1H), 4.84 (s, 1H), 4.68 (br. s., 2H), 4.32-4.22 (m, 2H), 2.75-2.71 (m, 2H), 2.70 (s, 3H), 2.11-2.01 (m, 2H), 1.78 (s, 3H), 1.08 (S, 9H). LCMS (M+H)=625.4.

Example 15

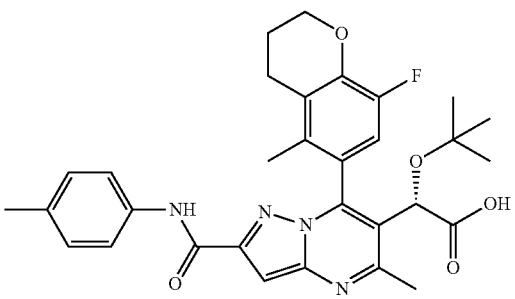 [SMILES: Cc1ccc(NC(=O)c2cc3nc(C)c([C@H](OC(C)(C)C)C(=O)O)c(-c4cc(F)c5c(c4C)CCCO5)n3n2)cc1]

(2S)-2-(tert-butoxy)-2-(7-(8-fluoro-5-methylchroman-6-yl)-5-methyl-2-(p-tolylcarbamoyl)pyrazolo[1,5-a]pyrimidin-6-yl)acetic acid $^1$H NMR (500 MHz, DMSO-d$_6$) δ: 9.94 (s, 1H), 7.63-7.57 (m, J=8.5 Hz, 2H), 7.20 (s, 1H), 7.18-7.13 (m, J=8.2 Hz, 2H), 7.09 (d, J=11.3 Hz, 1H), 4.81 (s, 1H), 4.30-4.25 (m, 2H), 2.75-2.73 (m, 2H), 2.72 (s, 3H), 2.28 (s, 3H), 2.12-2.02 (m, 2H), 1.81 (s, 3H), 1.08 (s, 9H). LCMS (M+H)=561.4.

Example 16

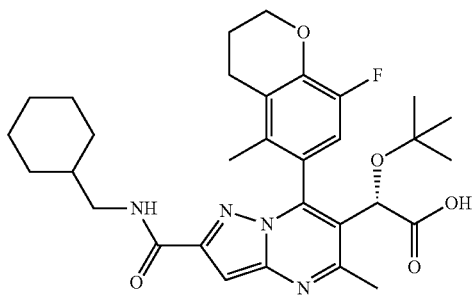

(2S)-2-(tert-butoxy)-2-(2-((cyclohexylmethyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.11 (t, J=6.1 Hz, 1H), 7.08 (d, J=11.0 Hz, 1H), 7.01 (s, 1H), 4.80 (s, 1H), 4.31-4.23 (m, 2H), 3.08 (t, J=6.7 Hz, 2H), 2.72 (t, J=6.6 Hz, 2H), 2.70 (s, 3H), 2.12-2.02 (m, 2H), 1.78 (s, 3H), 1.70-1.58 (m, 5H), 1.55-1.50 (m, 1H), 1.23-1.11 (m, 3H), 1.07 (s, 9H), 0.96-0.84 (m, 2H). LCMS (M+H)=567.4.

Example 17

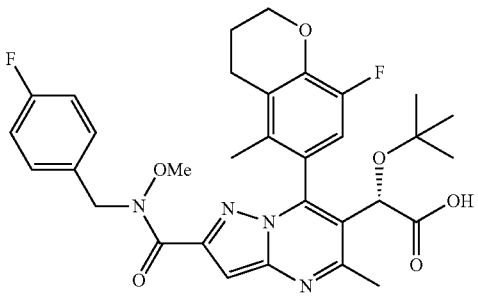 [SMILES: CON(Cc1ccc(F)cc1)C(=O)c1cc2nc(C)c([C@H](OC(C)(C)C)C(=O)O)c(-c3cc(F)c4c(c3C)CCCO4)n2n1]

(2S)-2-(tert-butoxy)-2-(7-(8-fluoro-5-methylchroman-6-yl)-2-((4-fluorobenzyl)(methoxy)carbamoyl)-5-methylpyrazolo[1,5-a]pyrimidin-6-yl)acetic acid $^1$H NMR (500 MHz, DMSO-d$_6$) δ: 7.28 (br. s., 2H), 7.07 (s, 2H), 7.10 (s, 1H), 6.98 (s, 1H), 4.98-4.83 (m, 2H), 4.76 (br. s., 1H), 4.29-4.12 (m, 2H), 3.55 (s, 3H), 2.72 (s, 3H), 2.70-2.63 (m, 2H), 2.03-1.88 (m, 2H), 1.73 (s, 3H), 1.11-1.06 (m, 9H). LCMS (M+H)=609.4.

Example 18

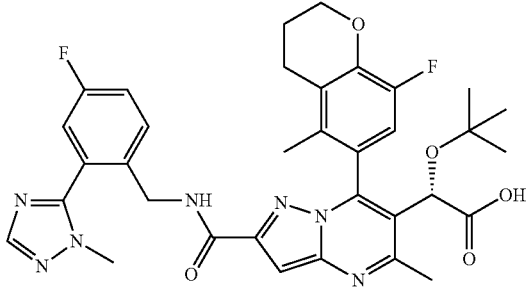 [SMILES: Cc1nc2cc(C(=O)NCc3ccc(F)cc3-c3ncnn3C)nn2c(-c2cc(F)c3c(c2C)CCCO3)c1[C@H](OC(C)(C)C)C(=O)O]

(2S)-2-(tert-butoxy)-2-(2-((4-fluoro-2-(1-methyl-1H-1,2,4-triazol-5-yl)benzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.68 (t, J=6.3 Hz, 1H), 7.92 (s, 1H), 7.56-7.47 (m, 2H), 7.39 (td, J=8.5, 2.7 Hz, 1H), 7.07 (d, J=11.3 Hz, 1H), 6.96 (s, 1H), 4.75 (br. s., 1H), 4.30 (d, J=7.3 Hz, 2H), 4.26 (t, J=5.2 Hz, 2H), 3.79 (s, 3H), 2.73-2.71 (m, 2H), 2.70 (s, 3H), 2.11-2.00 (m, 2H), 1.79 (s, 3H), 1.06 (s, 9H). LCMS (M+H)=660.4.

Example 19

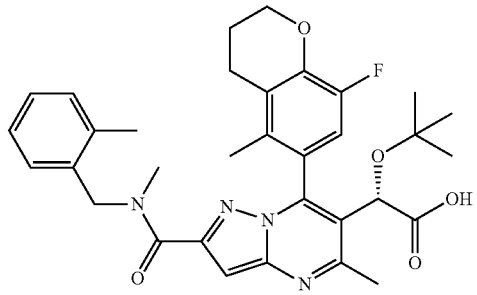 [SMILES: Cc1ccccc1CN(C)C(=O)c1cc2nc(C)c([C@H](OC(C)(C)C)C(=O)O)c(-c3cc(F)c4c(c3C)CCCO4)n2n1]

(2S)-2-(tert-butoxy)-2-(7-(8-fluoro-5-methylchroman-6-yl)-5-methyl-2-(methyl(2-methylbenzyl)carbamoyl)pyrazolo[1,5-a]pyrimidin-6-yl)acetic acid $^1$H NMR (500 MHz, DMSO-d$_6$) δ: 7.22-7.16 (m, 1.3H), 7.15-7.12 (m, 1.7H), 7.11-7.05 (m, 1H), 6.98 (s, 0.7H), 6.97 (d, J=5.2 Hz, 0.3H), 6.90 (s, 0.3H), 6.85 (s, 0.7H), 4.84 (d, J=18.3 Hz, 0.6H), 4.79 (d, J=4.6 Hz, 1H), 4.70-4.62 (m, 1.4H), 4.29-4.22 (m, 2H), 2.90 (s, 2H), 2.88 (s, 1H), 2.71 (s, 1H), 2.67 (s, 2H), 2.62-2.56 (m, 1H), 2.47-2.37 (m, 1H), 2.28 (s, 1H), 2.02 (s, 1H), 2.05-1.98 (m, 1H), 1.78 (s, 1H), 1.50 (s, 2H), 1.09 (s, 3H), 1.06 (s, 6H). LCMS (M+H)=589.5.

Example 20

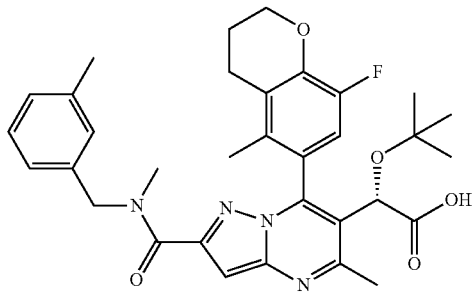 [SMILES: Cc1cccc(CN(C)C(=O)c2cc3nc(C)c([C@H](OC(C)(C)C)C(=O)O)c(-c4cc(F)c5c(c4C)CCCO5)n3n2)c1]

(2S)-2-(tert-butoxy)-2-(7-(8-fluoro-5-methylchroman-6-yl)-5-methyl-2-(methyl(3-methylbenzyl)carbamoyl)pyrazolo[1,5-a]pyrimidin-6-yl)acetic acid $^1$H NMR (500 MHz, DMSO-d$_6$) δ: 7.26-7.23 (m, 0.3H), 7.14-7.08 (m, 2.3H), 7.08-7.02 (m, 1H), 6.97 (s, 0.7H), 6.94 (d, J=7.3 Hz, 0.7H), 6.89 (s, 0.3H), 6.88 (s, 0.7H), 4.84 (s, 0.8H), 4.68 (d, J=15.3 Hz, 0.7H), 4.60 (d, J=2.4 Hz, 0.5H), 4.52 (d, J=15.3 Hz, 0.7H), 4.28-4.23 (m, 0.6H), 4.23-4.17 (m, 1.3H), 2.80 (s, 3H), 2.71 (s, 1H), 2.70 (s, 2H), 2.61-2.55 (m, 1H), 2.30 (s, 1H), 2.23 (s, 2H), 2.05 (br. s., 1H), 2.02-1.90 (m, 2H), 1.77 (s, 1H), 1.59 (s, 2H), 1.08 (s, 9H). LCMS (M+H)=589.4.

Example 21

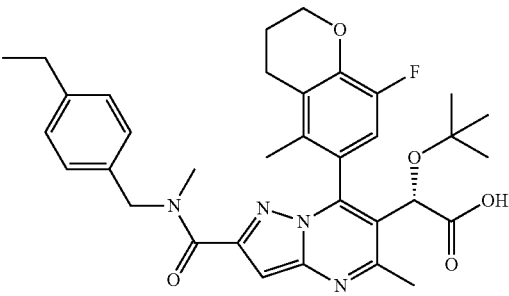 [SMILES: CCc1ccc(CN(C)C(=O)c2cc3nc(C)c([C@H](OC(C)(C)C)C(=O)O)c(-c4cc(F)c5c(c4C)CCCO5)n3n2)cc1]

(2S)-2-(tert-butoxy)-2-(2-((4-ethylbenzyl)(methyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 7.25-7.18 (m, 1H), 7.10-7.04 (m, 4H), 6.89-6.86 (m, 1H), 4.88-4.81 (m, 1H), 4.64-4.50 (m, 2H), 4.28-4.17 (m, 2H), 2.90 (s, 1H), 2.80 (s, 2H), 2.71 (s, 3H), 2.59 (q, J=7.4 Hz, 2H), 2.42-2.36 (m, 1H), 2.05-1.92 (m, 2H), 1.77 (s, 1H), 1.63 (s, 2H), 1.22-1.15 (m, 3H), 1.09 (s, 6H), 1.08 (s, 3H). LCMS (M+H)=603.4.

Example 22

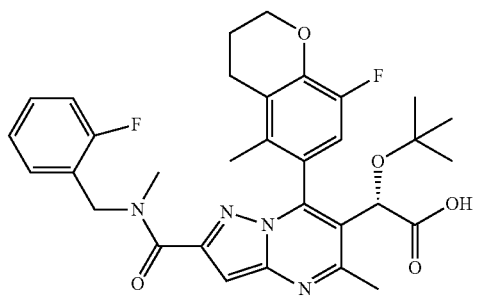 [SMILES: Cc1nc2cc(C(=O)N(C)Cc3ccccc3F)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-((2-fluorobenzyl)(methyl)carbamoyl)-5-methylpyrazolo[1,5-a]pyrimidin-6-yl)acetic acid $^1$H NMR (500 MHz, DMSO-d$_6$) δ: 7.40-7.29 (m, 1.4H), 7.26-7.19 (m, 0.6H), 7.18-7.12 (m, 1.4H), 7.11-7.07 (0.6H), 7.05-6.97 (m, 2H), 6.89 (s, 1H), 4.86-4.78 (m, 1.6H), 4.74 (s, 0.4H), 4.72-4.68 (m, 1H), 4.28-4.21 (m, 2H), 2.97 (s, 1H), 2.87 (s, 2H), 2.71 (s, 1H), 2.69 (s, 2H), 2.65-2.59 (m, 1H), 2.46-2.35 (m, 1H), 2.09-1.96 (m, 2H), 1.78 (s, 1H), 1.61 (s, 2H), 1.08 (s, 3H), 1.07 (s, 6H). LCMS (M+H)=593.5.

Example 23

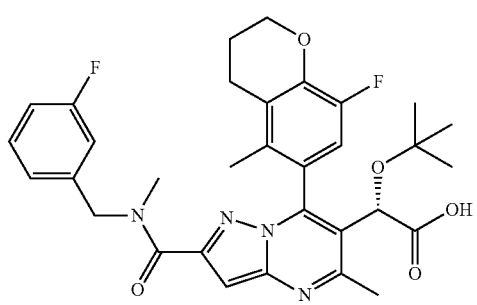 [SMILES: Cc1nc2cc(C(=O)N(C)Cc3cccc(F)c3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-β-fluorobenzyl)(methyl)carbamoyl)-5-methylpyrazolo[1,5-a]pyrimidin-6-yl)acetic acid $^1$H NMR (500 MHz, DMSO-d$_6$) δ: 7.44-7.39 (m, 0.25H), 7.31-7.25 (m, 0.75H), 7.19-7.07 (m, 1.8H), 7.05-6.96 (m, 2.2H), 6.92 (s, 0.25H), 6.91 (s, 0.75H), 4.85 (s, 0.25H), 4.82 (s, 0.75H), 4.72-4.61 (m, 2H), 4.28-4.16 (m, 2H), 2.95 (s, 0.75H), 2.82 (s, 2.25H), 2.71 (s, 1H), 2.70 (s, 2H), 2.62-2.56 (m, 1H), 2.34-2.28 (m, 1H), 2.11-1.92 (m, 2H), 1.78 (s, 1H), 1.60 (s, 2H), 1.09 (s, 2H), 1.08 (s, 7H). LCMS (M+H)=593.4.

Example 24

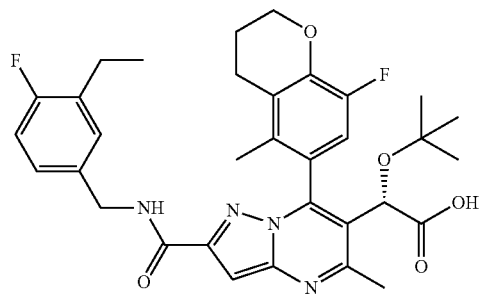 [SMILES: CCc1cc(CNC(=O)c2cc3nc(C)c([C@H](OC(C)(C)C)C(=O)O)c(-c4cc(F)c5c(c4C)CCCO5)n3n2)ccc1F]

(2S)-2-(tert-butoxy)-2-(2-((3-ethyl-4-fluorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.72 (t, J=6.3 Hz, 1H), 7.22 (dd, J=7.6, 2.1 Hz, 1H), 7.17-7.12 (m, 1H), 7.09 (d, J=4.0 Hz, 1H), 7.07 (d, J=1.8 Hz, 1H), 7.04 (s, 1H), 4.79 (s, 1H), 4.40 (d, J=6.4 Hz, 2H), 4.26 (t, J=5.0 Hz, 2H), 2.73-2.71 (m, 2H), 2.70 (s, 3H), 2.59 (q, J=7.5 Hz, 2H), 2.10-2.01 (m, 2H), 1.78 (s, 3H), 1.15 (t, J=7.6 Hz, 3H), 1.07 (s, 9H). LCMS (M+H)=607.4.

Example 25

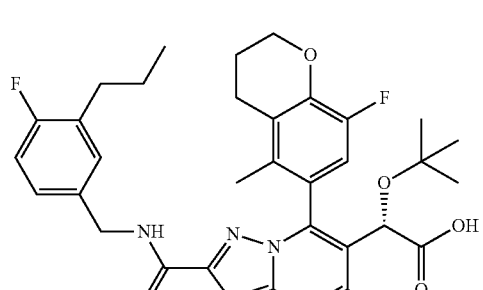

(2S)-2-(tert-butoxy)-2-(2-((4-fluoro-3-propylbenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.72 (t, J=6.3 Hz, 1H), 7.19 (dd, J=7.6, 2.1 Hz, 1H), 7.16-7.12 (m, 1H), 7.09 (d, J=4.6 Hz, 1H), 7.08-7.06 (m, 1H), 7.04 (s, 1H), 4.80 (s, 1H), 4.40 (d, J=6.1 Hz, 2H), 4.26 (t, J=5.2 Hz, 2H), 2.74-2.71 (m, 2H), 2.70

(s, 3H), 2.57-2.53 (m, 2H), 2.10-2.02 (m, 2H), 1.78 (s, 3H), 1.58-1.51 (m, 2H), 1.07 (s, 9H), 0.89 (t, J=7.5 Hz, 3H). LCMS (M+H)=621.4.

Example 26

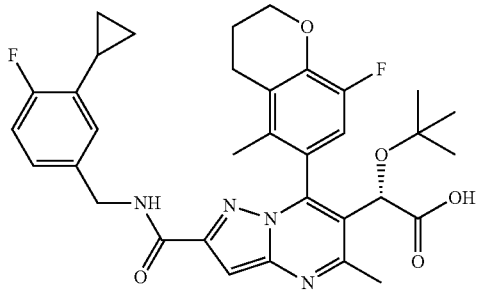 [SMILES: Cc1nc2cc(C(=O)NCc3ccc(F)c(C4CC4)c3)nn2c(-c2cc(F)c3c(c2C)CCCO3)c1[C@H](OC(C)(C)C)C(=O)O]

(2S)-2-(tert-butoxy)-2-(2-β-cyclopropyl-4-fluorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.67 (t, J=6.3 Hz, 1H), 7.12-7.04 (m, 3H), 7.02 (s, 1H), 6.92 (dd, J=7.6, 1.8 Hz, 1H), 4.74 (s, 1H), 4.36 (d, J=6.1 Hz, 2H), 4.25 (t, J=5.3 Hz, 2H), 2.74-2.71 (m, 2H), 2.70 (s, 3H), 2.09-1.97 (m, 3H), 1.79 (s, 3H), 1.06 (s, 9H), 0.99-0.93 (m, 2H), 0.68-0.63 (m, 2H). LCMS (M+H)=619.4.

Example 27

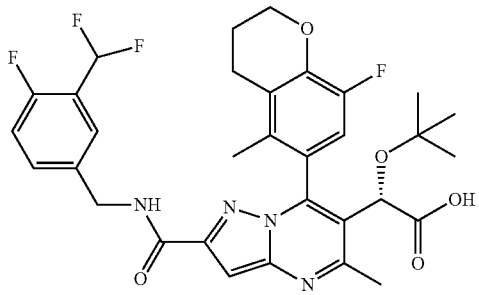 [SMILES: Cc1nc2cc(C(=O)NCc3ccc(F)c(C(F)F)c3)nn2c(-c2cc(F)c3c(c2C)CCCO3)c1[C@H](OC(C)(C)C)C(=O)O]

(2S)-2-(tert-butoxy)-2-(2-O-(difluoromethyl)-4-fluorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.82 (t, J=6.3 Hz, 1H), 7.58-7.50 (m, 2H), 7.36-7.30 (m, 1H), 7.12-7.07 (m, 1H), 7.04 (s, 1H), 4.79 (s, 1H), 4.46 (d, J=6.4 Hz, 2H), 4.26 (t, J=5.2 Hz, 2H), 2.74-2.71 (m, 2H), 2.70 (s, 3H), 2.11-2.01 (m, 2H), 1.78 (s, 3H), 1.07 (s, 9H). LCMS (M+H)=629.4.

Example 28

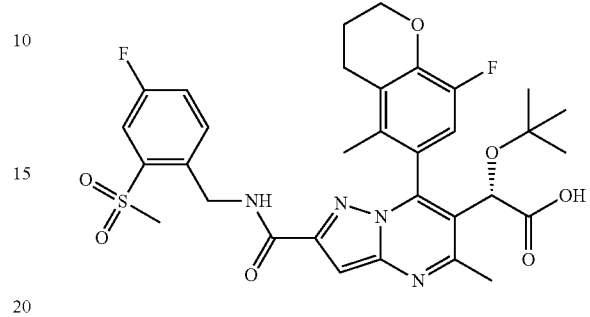

(2S)-2-(tert-butoxy)-2-(2-((4-fluoro-2-(methylsulfonyl)benzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.81 (t, J=6.3 Hz, 1H), 7.69 (dt, J=8.2, 1.3 Hz, 1H), 7.61-7.55 (m, 2H), 7.09 (d, J=11.3 Hz, 1H), 7.05 (s, 1H), 4.83 (s, 1H), 4.79 (dd, J=6.0, 3.5 Hz, 2H), 4.26 (t, J=5.2 Hz, 2H), 3.41 (s, 3H), 2.74-2.72 (m, 2H), 2.71 (s, 3H), 2.09-2.04 (m, 2H), 1.79 (s, 3H), 1.08 (s, 9H). LCMS (M+H)=657.4.

Example 29

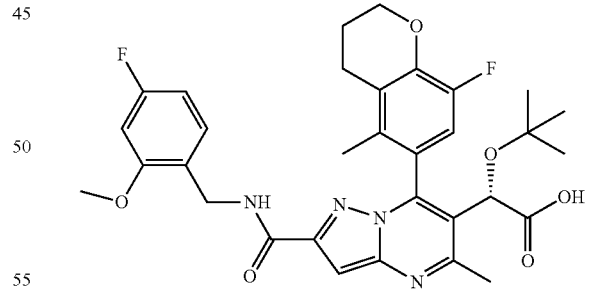

(2S)-2-(tert-butoxy)-2-(2-((4-fluoro-2-methoxybenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.46 (t, J=6.1 Hz, 1H), 7.17-7.08 (m, 2H), 7.05 (s, 1H), 6.92 (dd, J=11.3, 2.4 Hz, 1H), 6.72 (td, J=8.5, 2.6 Hz, 1H), 4.83 (s, 1H), 4.37 (d, J=6.4 Hz, 2H), 4.26 (t, J=5.2 Hz, 2H), 3.80 (s, 3H), 2.74-2.71 (m, 2H), 2.70 (s, 3H), 2.06 (dq, J=11.3, 5.7 Hz, 2H), 1.79 (s, 3H), 1.08 (s, 9H). LCMS (M+H)=609.4.

3H), 1.57-1.46 (m, 2H), 1.29 (dq, J=14.8, 7.4 Hz, 2H), 1.07 (s, 9H), 0.88 (t, J=7.3 Hz, 3H). LCMS (M+H)=617.5.

Example 30

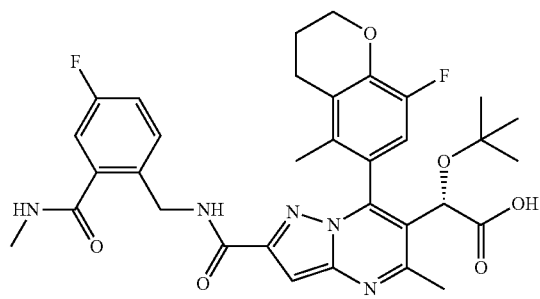 [SMILES: CNC(=O)c1cc(F)ccc1CNC(=O)c1cc2nc(C)c([C@H](OC(C)(C)C)C(=O)O)c(-c3cc(F)c4c(c3C)CCCO4)n2n1]

(2S)-2-(tert-butoxy)-2-(2-((4-fluoro-2-(methylcarbamoyl)benzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.56 (t, J=6.3 Hz, 1H), 8.51 (q, J=4.3 Hz, 1H), 7.40-7.33 (m, 1H), 7.29-7.23 (m, 2H), 7.07 (d, J=11.0 Hz, 1H), 7.00 (s, 1H), 4.83 (s, 1H), 4.55-4.44 (m, 2H), 4.30-4.22 (m, 2H), 2.76-2.73 (m, 2H), 2.71 (s, 3H), 2.12-2.02 (m, 2H), 1.78 (s, 3H), 1.08 (s, 9H). LCMS (M+H)=636.4.

Example 31

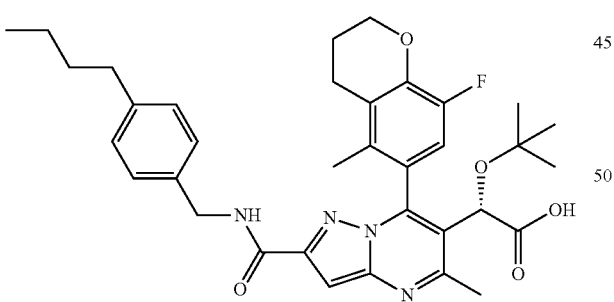

(2S)-2-(tert-butoxy)-2-(2-((4-butylbenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.69 (t, J=6.3 Hz, 1H), 7.21-7.17 (m, J=7.9 Hz, 2H), 7.14-7.11 (m, J=8.2 Hz, 2H), 7.08 (d, J=11.3 Hz, 1H), 7.04 (s, 1H), 4.79 (s, 1H), 4.40 (d, J=6.7 Hz, 2H), 4.26 (t, J=5.2 Hz, 2H), 2.74-2.71 (m, 2H), 2.70 (s, 3H), 2.57-2.53 (m, 2H), 2.05 (d, J=4.9 Hz, 2H), 1.78 (s,

Example 32

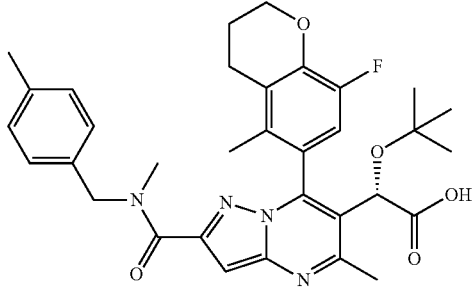 [SMILES: Cc1ccc(CN(C)C(=O)c2cc3nc(C)c([C@H](OC(C)(C)C)C(=O)O)c(-c4cc(F)c5c(c4C)CCCO5)n3n2)cc1]

(2S)-2-(tert-butoxy)-2-(7-(8-fluoro-5-methylchroman-6-yl)-5-methyl-2-(methyl(4-methylbenzyl)carbamoyl)pyrazolo[1,5-a]pyrimidin-6-yl)acetic acid $^1$H NMR (500 MHz, DMSO-d$_6$) δ: 7.23-7.15 (m, 1H), 7.08-7.00 (m, 4H), 6.88-6.85 (m, 1H), 4.84 (s, 1H), 4.63 (d, J=15.0 Hz, 1H), 4.49 (d, J=15.3 Hz, 1H), 4.29-4.17 (m, 2H), 2.89 (s, 1H), 2.79 (s, 2H), 2.71 (s, 3H), 2.68-2.55 (m, 1H), 2.43-2.31 (m, 1H), 2.30 (s, 3H), 2.09-1.90 (m, 2H), 1.77 (s, 1H), 1.61 (s, 2H), 1.09 (s, 6H), 1.08 (s, 3H). LCMS (M+H)=589.4.

Example 33

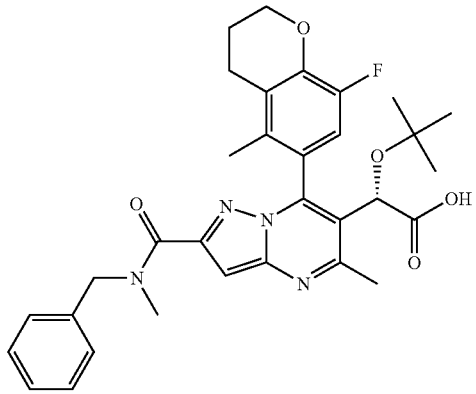 [SMILES: Cc1nc2cc(C(=O)N(C)Cc3ccccc3)nn2c(-c2cc(F)c3c(c2C)CCCO3)c1[C@H](OC(C)(C)C)C(=O)O]

(2S)-2-(2-(benzyl(methyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-d$_6$) δ: 7.97 (s, 1H), 7.39-7.03 (m, 6H), 6.89 (s, 0.33H), 6.89 (s, 0.67H), 4.85 (s, 1H), 4.68-4.56 (m, 2H), 4.28-4.21 (m, 2H), 2.92 (s, 1H), 2.91 (s, 2H), 2.73-2.69 (m, 5H), 2.09-1.92 (m, 2H), 1.77 (s, 1H), 1.61 (s, 2H), 1.08 (s, 9H). LCMS (M+H)=575.4.

Example 34

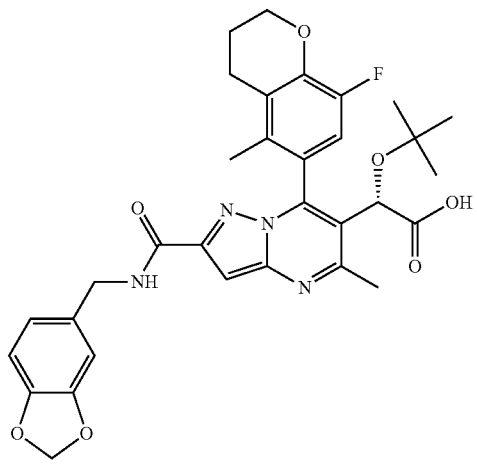 [SMILES: Cc1nc2cc(C(=O)NCc3ccc4c(c3)OCO4)nn2c(-c2cc(F)c3c(c2C)CCCO3)c1[C@H](OC(C)(C)C)C(=O)O]

(2S)-2-(2-((benzo[d][1,3]dioxol-5-ylmethyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-d$_6$) δ: 8.67 (t, J=6.3 Hz, 1H), 7.97 (s, 1H), 7.09 (d, J=11.3 Hz, 1H), 7.04 (s, 1H), 6.86 (d, J=1.5 Hz, 1H), 6.85 (s, 0.4H), 6.83 (s, 0.6H), 6.78 (d, J=1.8 Hz, 0.6H), 6.76 (d, J=1.8 Hz, 0.4H), 5.97 (s, 2H), 4.80 (s, 1H), 4.34 (d, J=6.4 Hz, 2H), 4.26 (t, J=5.3 Hz, 2H), 2.72 (t, J=6.4 Hz, 2H), 2.70 (s, 3H), 2.10-2.03 (m, 2H), 1.78 (s, 3H), 1.07 (s, 9H). LCMS (M+H)=605.4.

Example 35

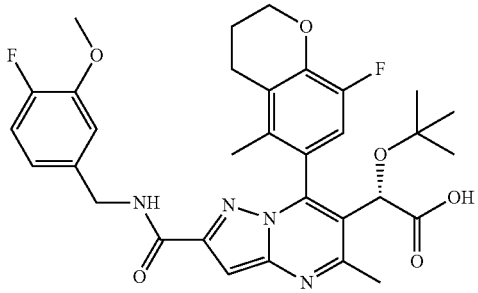 [SMILES: COc1cc(CNC(=O)c2cc3nc(C)c([C@H](OC(C)(C)C)C(=O)O)c(-c4cc(F)c5c(c4C)CCCO5)n3n2)ccc1F]

(2S)-2-(tert-butoxy)-2-(2-((4-fluoro-3-methoxybenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.68 (t, J=6.3 Hz, 1H), 7.16-7.09 (m, 2H), 7.04 (d, J=11.0 Hz, 1H), 7.00 (s, 1H), 6.84 (ddd, J=8.2, 4.3, 1.8 Hz, 1H), 4.63 (br. s., 1H), 4.41 (d, J=6.1 Hz, 2H), 4.25 (t, J=5.0 Hz, 2H), 3.80 (s, 3H), 2.74-2.71 (m, 2H), 2.71 (s, 3H), 2.10-2.01 (m, 2H), 1.81 (s, 3H), 1.05 (s, 9H). LCMS (M+H)=609.4.

Example 36

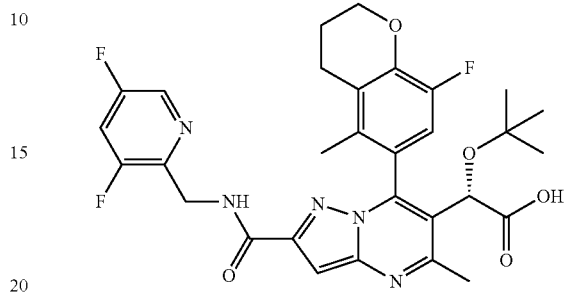

(2S)-2-(tert-butoxy)-2-(2-(((3,5-difluoropyridin-2-yl)methyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.65 (t, J=5.8 Hz, 1H), 8.43 (d, J=2.1 Hz, 1H), 7.93 (ddd, J=10.1, 9.0, 2.3 Hz, 1H), 7.10 (d, J=11.3 Hz, 1H), 7.04-7.01 (m, 1H), 4.82 (s, 1H), 4.67-4.52 (m, 2H), 4.26 (t, J=5.2 Hz, 2H), 2.74-2.71 (m, 2H), 2.70 (s, 3H), 2.09-2.05 (m, 2H), 1.79 (s, 3H), 1.08 (s, 9H). LCMS (M+H)=598.4.

Example 37

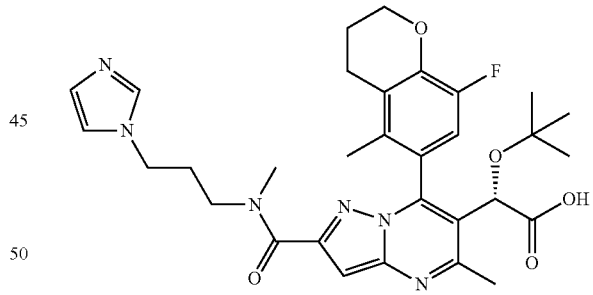

(2S)-2-(2-((3-(1H-imidazol-1-yl)propyl)(methyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-d$_6$) δ: 7.66 (s, 0.3H), 7.45 (s, 0.7H), 7.23 (s, 0.3H), 7.13 (d, J=11.0 Hz, 0.7H), 7.09 (d, J=11.0 Hz, 0.3H), 6.97 (s, 0.7H), 6.90 (s, 0.3H), 6.83 (s, 0.7H), 6.82 (s, 0.3H), 6.78 (s, 0.7H), 4.82 (s, 1H), 4.26 (t, J=5.3 Hz, 1H), 4.22 (t, J=7.5 Hz, 1H), 4.11 (t, J=7.3 Hz, 1H), 4.00 (t, J=7.2 Hz, 1H), 3.66-3.60 (m, 2H), 2.93 (s, 1H), 2.89 (s, 2H), 2.72 (s, 2H), 2.70 (br. s., 1H), 2.68-2.62 (m, 1H), 2.61-2.54 (m, 1H), 2.08-1.96 (m, 2H), 1.92-1.82 (m, 2H), 1.77 (s, 3H), 1.09 (s, 7H), 1.08 (s, 2H). LCMS (M+H)=593.5.

1.77 (s, 1.5H), 1.50 (s, 1.5H), 1.48 (s, 1.5H), 1.06 (s, 4.5H), 1.06 (s, 4.5H). LCMS (M+H)=575.3.

Example 38

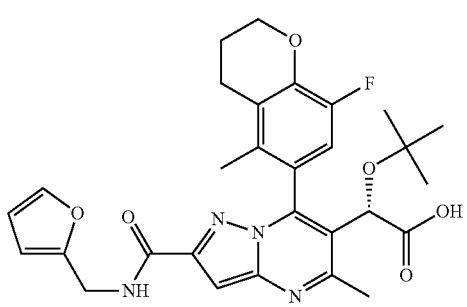 [SMILES: Cc1nc2cc(C(=O)NCc3ccco3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-((furan-2-ylmethyl)carbamoyl)-5-methylpyrazolo[1,5-a]pyrimidin-6-yl)acetic acid $^1$H NMR (500 MHz, DMSO-d$_6$) δ: 8.62 (t, J=6.1 Hz, 1H), 7.97 (s, 1H), 7.56 (dd, J=1.7, 0.8 Hz, 1H), 7.07 (d, J=11.3 Hz, 1H), 7.03 (s, 1H), 6.39 (dd, J=3.1, 1.8 Hz, 1H), 6.24 (dd, J=3.2, 0.8 Hz, 1H), 4.75 (s, 1H), 4.43 (t, J=6.1 Hz, 2H), 4.26 (t, J=5.5 Hz, 2H), 2.72 (t, J=6.6 Hz, 2H), 2.70 (s, 3H), 2.09-2.03 (m, 2H), 1.79 (s, 3H), 1.06 (s, 9H). LCMS (M+H)= 551.3.

Example 39

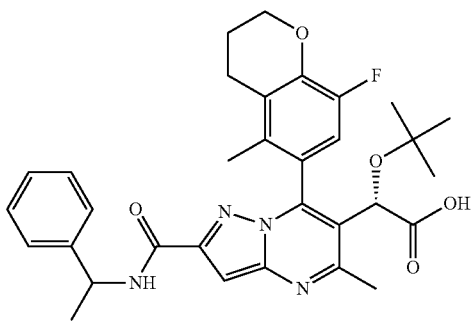 [SMILES: Cc1nc2cc(C(=O)NC(C)c3ccccc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(O-phenylethyl)carbamoyl)pyrazolo[1,5-a]pyrimidin-6-yl)acetic acid $^1$H NMR (500 MHz, DMSO-d$_6$) δ: 8.60 (d, J=8.2 Hz, 0.5H), 8.57 (d, J=8.2 Hz, 0.5H), 7.97 (s, 1H), 7.39-7.36 (m, 2H), 7.35-7.30 (m, 2H), 7.26-7.21 (m, 1H), 7.11 (s, 0.5H), 7.10 (s, 0.5H), 7.07 (d, J=3.7 Hz, 0.5H), 7.04 (d, J=4.3 Hz, 0.5H), 5.20-5.12 (m, 1H), 4.74 (br. s., 1H), 4.26 (t, J=5.0 Hz, 2H), 2.73-2.68 (m, 5H), 2.09-2.02 (m, 2H), 1.78 (s, 1.5H), Example 40

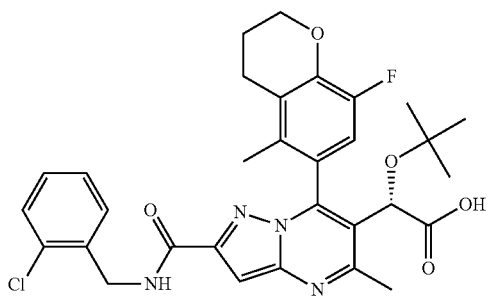 [SMILES: Cc1nc2cc(C(=O)NCc3ccccc3Cl)nn2c(-c2cc(F)c3c(c2C)CCCO3)c1[C@H](OC(C)(C)C)C(=O)O]

(2S)-2-(tert-butoxy)-2-(2-((2-chlorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.73 (t, J=6.1 Hz, 1H), 7.97 (s, 1H), 7.47-7.44 (m, 1H), 7.34-7.26 (m, 3H), 7.10 (d, J=11.3 Hz, 1H), 7.07 (s, 1H), 4.80 (s, 1H), 4.52 (d, J=6.1 Hz, 2H), 4.26 (t, J=5.2 Hz, 2H), 2.74-2.69 (m, 5H), 2.11-2.01 (m, 2H), 1.80 (s, 3H), 1.08 (s, 9H). LCMS (M+H)=595.3 and 597.3.

Example 41

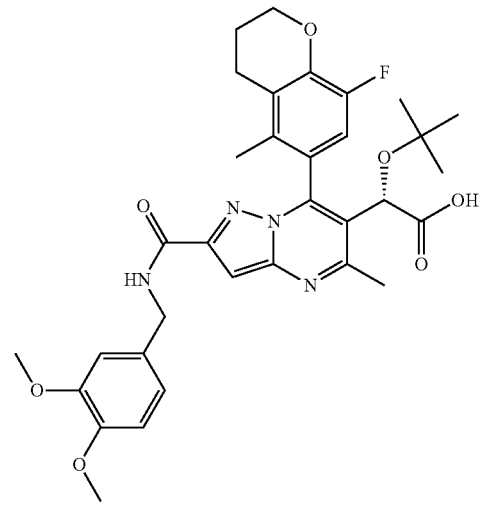 [SMILES: COc1ccc(CNC(=O)c2cc3nc(C)c([C@H](OC(C)(C)C)C(=O)O)c(-c4cc(F)c5c(c4C)CCCO5)n3n2)cc1OC]

(2S)-2-(tert-butoxy)-2-(2-((3,4-dimethoxybenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.62 (t, J=6.3 Hz, 1H), 7.97 (s, 1H), 7.08 (d, J=11.3 Hz, 1H), 7.03 (s, 1H), 6.92 (d, J=1.8 Hz, 1H), 6.90-6.87 (m, 1H), 6.82 (d, J=2.1 Hz, 0.6H), 6.80 (d, J=2.1 Hz, 0.4H), 4.77 (s, 1H), 4.37 (d, J=6.1 Hz, 2H), 4.26 (t, J=5.2 Hz, 2H), 3.72 (s, 3H), 3.71 (s, 3H), 2.74-2.68 (m, 5H), 2.09-2.01 (m, 2H), 1.78 (s, 3H), 1.07 (s, 9H). LCMS (M+H)=621.4.

Example 42

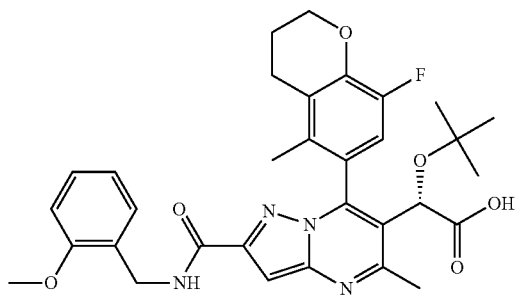 [SMILES: COc1ccccc1CNC(=O)c1cc2nc(C)c([C@H](OC(C)(C)C)C(=O)O)c(-c3cc(F)c4c(c3C)CCCO4)n2n1]

(2S)-2-(tert-butoxy)-2-(7-(8-fluoro-5-methylchroman-6-yl)-2-((2-methoxybenzyl)carbamoyl)-5-methylpyrazolo[1,5-a]pyrimidin-6-yl)acetic acid $^1$H NMR (400 MHz, DMSO-d$_6$) δ: 8.37 (t, J=6.1 Hz, 1H), 7.97 (s, 1H), 7.28-7.22 (m, 1H), 7.15 (d, J=6.0 Hz, 1H), 7.09 (d, J=11.0 Hz, 1H), 7.04 (s, 1H), 7.00 (d, J=8.3 Hz, 1H), 6.92-6.86 (m, 1H), 4.83 (s, 1H), 4.43 (d, J=6.0 Hz, 2H), 4.27 (t, J=5.0 Hz, 2H), 3.78 (s, 3H), 2.74-2.68 (m, 5H), 2.11-2.02 (m, 2H), 1.80 (s, 3H), 1.08 (s, 9H). LCMS (M+H)=591.3.

Example 43

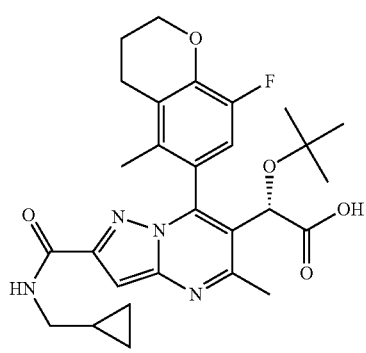 [SMILES: Cc1nc2cc(C(=O)NCC3CC3)nn2c(-c2cc(F)c3c(c2C)CCCO3)c1[C@H](OC(C)(C)C)C(=O)O]

(2S)-2-(tert-butoxy)-2-(2-((cyclopropylmethyl)carbamoyl)-7-(8-fluoro-5-methylchroman-6-yl)-5-methylpyrazolo[1,5-a]pyrimidin-6-yl)acetic acid $^1$H NMR (400 MHz, DMSO-d$_6$) δ: 8.16 (t, J=6.0 Hz, 1H), 7.97 (s, 1H), 7.07 (d, J=11.3 Hz, 1H), 7.00 (s, 1H), 4.76 (s, 1H), 4.27 (t, J=5.1 Hz, 2H), 3.18-3.05 (m, 2H), 2.74-2.67 (m, 5H), 2.14-2.03 (m, 2H), 1.80 (s, 3H), 1.07 (s, 9H), 1.05-0.98 (m, 1H), 0.44-0.38 (m, 2H), 0.25-0.20 (m, 2H). LCMS (M+H)=525.3.

Example 44

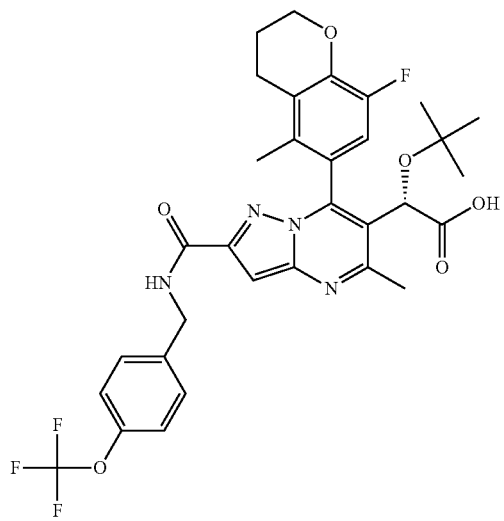 [SMILES: Cc1nc2cc(C(=O)NCc3ccc(OC(F)(F)F)cc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((4-(trifluoromethoxy)benzyl)carbamoyl)pyrazolo[1,5-a]pyrimidin-6-yl)acetic acid $^1$H NMR (400 MHz, DMSO-d$_6$) δ: 8.75 (t, J=6.3 Hz, 1H), 7.97 (s, 1H), 7.42 (d, J=8.8 Hz, 2H), 7.31 (d, J=8.0 Hz, 2H), 7.07 (d, J=11.0 Hz, 1H), 7.03 (s, 1H), 4.78 (s, 1H), 4.46 (d, J=6.5 Hz, 2H), 4.26 (t, J=5.3 Hz, 2H), 2.75-2.69 (m, 5H), 2.11-2.02 (m, 2H), 1.79 (s, 3H), 1.07 (s, 9H). LCMS (M+H)=645.3.

Example 45

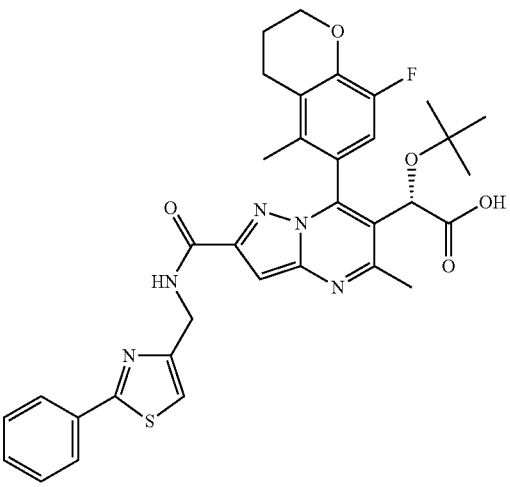 [SMILES: Cc1nc2cc(C(=O)NCc3csc(-c4ccccc4)n3)nn2c(-c2cc(F)c3c(c2C)CCCO3)c1[C@H](OC(C)(C)C)C(=O)O]

45

(2S)-2-(tert-butoxy)-2-(7-(8-fluoro-5-methylchroman-6-yl)-5-methyl-2-(((2-phenylthiazol-4-yl)methyl)carbamoyl)pyrazolo[1,5-a]pyrimidin-6-yl)acetic acid ¹H NMR (400 MHz, DMSO-d₆) δ: 8.69 (t, J=6.0 Hz, 1H), 7.97 (s, 1H), 7.94-7.89 (m, 2H), 7.54-7.48 (m, 3H), 7.43 (s, 1H), 7.06 (d, J=10.5 Hz, 1H), 7.05 (s, 1H), 4.77 (s, 1H), 4.62-4.58 (m, 2H), 4.25 (t, J=5.1 Hz, 2H), 2.71 (s, 5H), 2.10-2.01 (m, 2H), 1.80 (s, 3H), 1.07 (s, 9H). LCMS (M+H)= 644.3.

Example 46

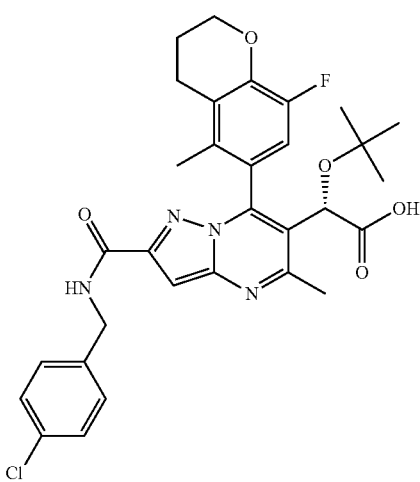 [SMILES: Cc1nc2cc(C(=O)NCc3ccc(Cl)cc3)nn2c(-c2cc(F)c3c(c2C)CCCO3)c1[C@H](OC(C)(C)C)C(=O)O]

(2S)-2-(tert-butoxy)-2-(2((4-chlorobenzyl)carbamoyl)-7-(8-fluoro-5-methylchroman-6-yl)-5-methylpyrazolo[1,5-a]pyrimidin-6-yl)acetic acid ¹H NMR (500 MHz, DMSO-d₆) δ: 8.77 (t, J=6.3 Hz, 1H), 7.97 (s, 1H), 7.40-7.36 (m, 2H), 7.34-7.29 (m, 2H), 7.09 (d, J=11.0 Hz, 1H), 7.04 (s, 1H), 4.79 (s, 1H), 4.42 (d, J=7.0 Hz, 2H), 4.26 (t, J=5.2 Hz, 2H), 2.74-2.68 (m, 5H), 2.10-2.02 (m, 2H), 1.78 (s, 3H), 1.07 (s, 9H). LCMS (M+H)=595.3.

Example 47

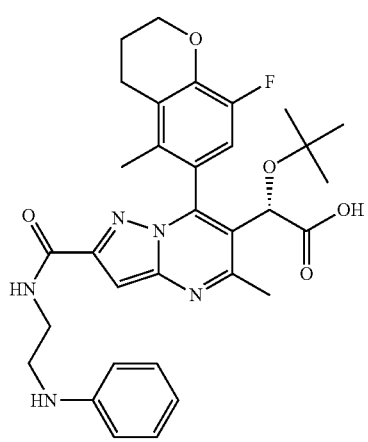 [SMILES: Cc1nc2cc(C(=O)NCCNc3ccccc3)nn2c(-c2cc(F)c3c(c2C)CCCO3)c1[C@H](OC(C)(C)C)C(=O)O]

46

(2S)-2-(tert-butoxy)-2-(7-(8-fluoro-5-methylchroman-6-yl)-5-methyl-2-((2-(phenylamino)ethyl)carbamoyl)pyrazolo[1,5-a]pyrimidin-6-yl)acetic acid ¹H NMR (500 MHz, DMSO-d₆) δ: 8.25 (t, J=6.0 Hz, 1H), 7.97 (s, 1H), 7.10-7.04 (m, 3H), 7.00 (s, 1H), 6.63-6.58 (m, 2H), 6.52 (t, J=7.2 Hz, 1H), 5.73 (br. s., 1H), 4.75 (s, 1H), 4.26 (t, J=5.0 Hz, 2H), 3.20-3.11 (m, 4H), 2.73-2.67 (m, 5H), 2.11-2.03 (m, 2H), 1.79 (s, 3H), 1.07 (s, 9H). LCMS (M+H)= 590.3.

Example 48

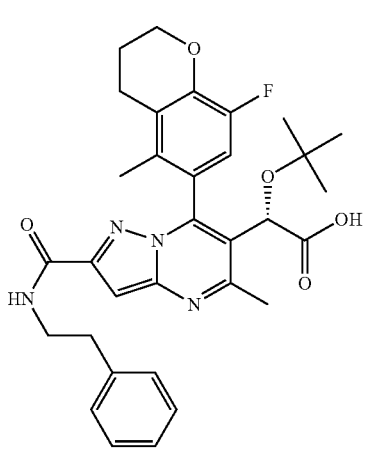 [SMILES: Cc1nc2cc(C(=O)NCCc3ccccc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(phenethylcarbamoyl)pyrazolo[1,5-a]pyrimidin-6-yl)acetic acid ¹H NMR (500 MHz, DMSO-d₆) δ: 8.11 (t, J=6.0 Hz, 1H), 7.97 (s, 1H), 7.31-7.26 (m, 2H), 7.23-7.17 (m, 3H), 7.07 (d, J=11.3 Hz, 1H), 6.98 (s, 1H), 4.76 (s, 1H), 4.27 (t, J=5.5 Hz, 2H), 3.48-3.43 (t, J=7.5 Hz, 2H), 2.81 (t, J=7.5 Hz, 2H), 2.74-2.68 (m, 5H), 2.12-2.04 (m, 2H), 1.78 (s, 3H), 1.07 (s, 9H). LCMS (M+H)=575.4.

Example 49

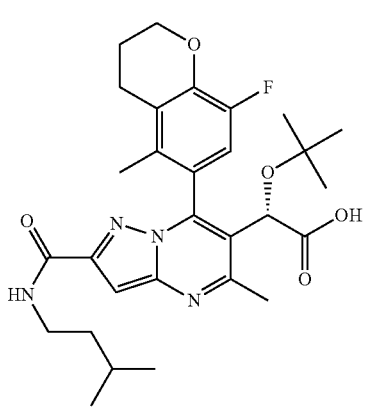 [SMILES: Cc1nc2cc(C(=O)NCCC(C)C)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-(isopentylcarbamoyl)-5-methylpyrazolo[1,5-a]pyrimidin-6-yl)acetic acid $^{1}$H NMR (500 MHz, DMSO-d$_{6}$) δ 8.11 (t, J=6.0 Hz, 1H), 7.97 (s, 1H), 7.07 (d, J=11.3 Hz, 1H), 6.98 (s, 1H), 4.75 (s, 1H), 4.27 (t, J=5.6 Hz, 2H), 3.27-3.22 (m, 2H), 2.72 (t, J=6.4 Hz, 2H), 2.69 (s, 3H), 2.10-2.03 (d, J=4.0 Hz, 2H), 1.78 (s, 3H), 1.60-1.52 (m, 1H), 1.42-1.36 (m, 2H), 1.07 (s, 9H), 0.89 (d, J=6.7 Hz, 6H). LCMS (M+H)=541.4.

Example 50

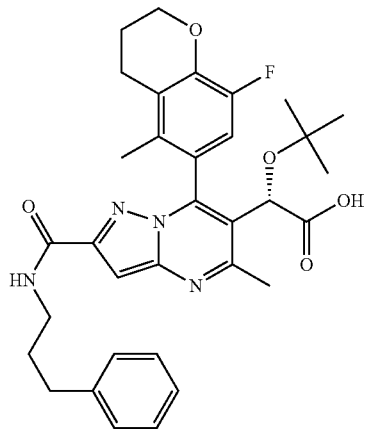 [SMILES: Cc1nc2cc(C(=O)NCCCc3ccccc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-β-phenylpropyl)carbamoyl) pyrazolo[1,5-a]pyrimidin-6-yl)acetic acid $^{1}$H NMR (500 MHz, DMSO-d$_{6}$) δ: 8.18 (t, J=6.0 Hz, 1H), 7.97 (s, 1H), 7.30-7.25 (m, 2H), 7.23-7.15 (m, 3H), 7.06 (d, J=11.3 Hz, 1H), 6.98 (s, 1H), 4.72 (br. s., 1H), 4.26 (t, J=5.3 Hz, 2H), 3.27-3.21 (m, 2H), 2.74-2.69 (m, 5H), 2.59 (t, J=7.6 Hz, 2H), 2.09-2.02 (m, 2H), 1.84-1.77 (m, 2H), 1.79 (s, 3H), 1.06 (s, 9H). LCMS (M+H)=589.4.

Example 51

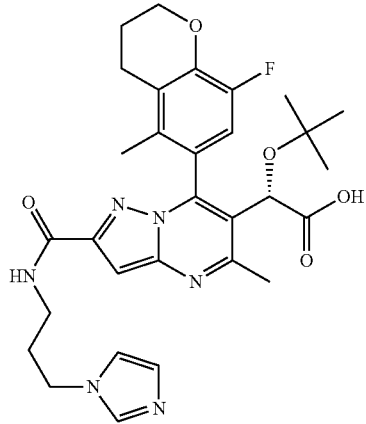 [SMILES: Cc1nc2cc(C(=O)NCCCn3ccnc3)nn2c(-c2cc(F)c3c(c2C)CCCO3)c1[C@H](OC(C)(C)C)C(=O)O]

(2S)-2-(2-O-(1H-imidazol-1-yl)propyl)carbamoyl)-7-(8-fluoro-5-methylchroman-6-yl)-5-methylpyrazolo[1,5-a]pyrimidin-6-yl)-2-(tert-butoxy)acetic acid $^{1}$H NMR (500 MHz, DMSO-d$_{6}$) δ: 8.25 (t, J=6.0 Hz, 1H), 8.27-8.23 (m, 1H), 7.98-7.96 (m, 1H), 7.65 (s, 1H), 7.20 (s, 1H), 7.07 (d, J=11.0 Hz, 1H), 7.00 (s, 1H), 6.88 (s, 1H), 4.75 (s, 1H), 4.26 (t, J=5.5 Hz, 2H), 3.98 (t, J=6.9 Hz, 2H), 3.25-3.19 (m, 2H), 2.72 (t, J=6.6 Hz, 2H), 2.70 (s, 3H), 2.10-2.03 (m, 2H), 1.97-1.90 (m, 2H), 1.79 (s, 3H), 1.07 (s, 9H). LCMS (M+H)=579.3.

Example 52

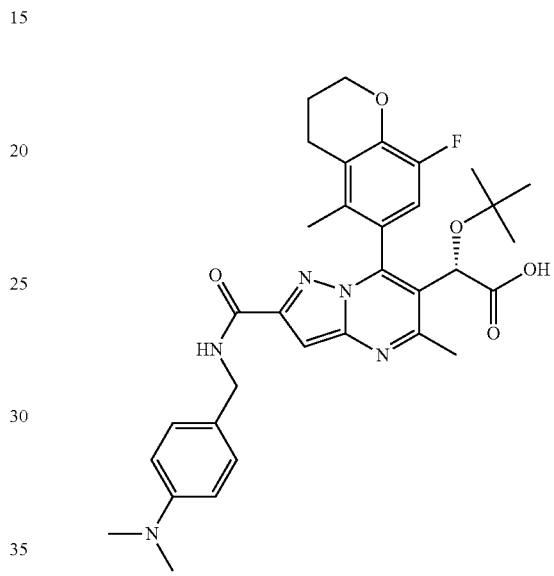

(2S)-2-(tert-butoxy)-2-(2-((4-(dimethylamino)benzyl)carbamoyl)-7-(8-fluoro-5-methylchroman-6-yl)-5-methylpyrazolo[1,5-a]pyrimidin-6-yl)acetic acid $^{1}$H NMR (500 MHz, DMSO-d$_{6}$) δ: 8.53 (t, J=6.1 Hz, 1H), 7.97 (s, 1H), 7.12 (d, J=8.9 Hz, 2H), 7.06 (d, J=11.3 Hz, 1H), 7.01 (s, 1H), 6.68-6.64 (m, 2H), 4.72 (s, 1H), 4.31 (d, J=6.1 Hz, 2H), 4.25 (t, J=5.3 Hz, 2H), 2.85 (s, 6H), 2.73-2.68 (m, 5H), 2.08-2.02 (m, 2H), 1.78 (s, 3H), 1.06 (s, 9H). LCMS (M+H)=604.4.

Example 53

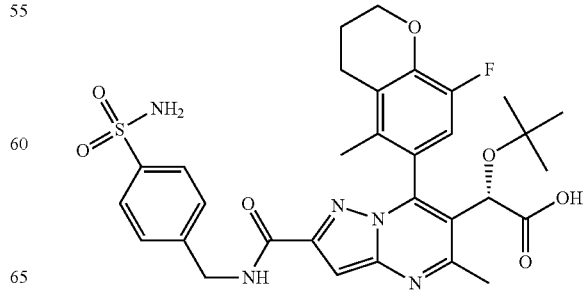

(2S)-2-(tert-butoxy)-2-(7-(8-fluoro-5-methylchroman-6-yl)-5-methyl-2-((4-sulfamoylbenzyl)carbamoyl)pyrazolo[1,5-a]pyrimidin-6-yl)acetic acid $^1$H NMR (500 MHz, DMSO-d$_6$) δ: 8.82 (t, J=6.3 Hz, 1H), 7.97 (s, 1H), 7.78-7.75 (d, J=8.5 Hz, 2H), 7.46 (d, J=8.5 Hz, 2H), 7.30 (s, 2H), 7.08 (d, J=11.3 Hz, 1H), 7.04 (s, 1H), 4.75 (s, 1H), 4.52-4.48 (m, 2H), 4.26 (t, J=5.0 Hz, 2H), 2.74-2.69 (m, 5H), 2.09-2.02 (m, 2H), 1.80 (s, 3H), 1.06 (s, 9H). LCMS (M+H)=640.3.

Example 54

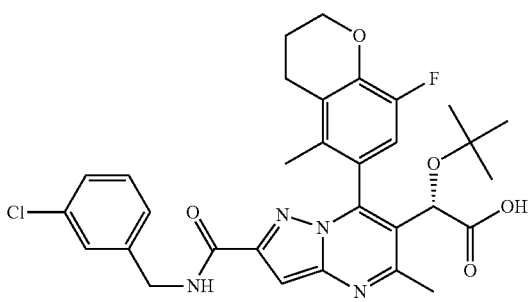 [SMILES: Cc1nc2cc(C(=O)NCc3cccc(Cl)c3)nn2c(-c2cc(F)c3c(c2C)CCCO3)c1[C@H](OC(C)(C)C)C(=O)O]

(2S)-2-(tert-butoxy)-2-(2((3-chlorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.78 (t, J=6.4 Hz, 1H), 7.97 (s, 1H), 7.37-7.29 (m, 3H), 7.26 (d, J=7.6 Hz, 1H), 7.08 (d, J=11.3 Hz, 1H), 7.03 (s, 1H), 4.73 (s, 1H), 4.44 (d, J=6.4 Hz, 2H), 4.25 (t, J=5.2 Hz, 2H), 2.74-2.69 (m, 5H), 2.09-2.02 (m, 2H), 1.80 (s, 3H), 1.06 (s, 9H). LCMS (M+H)=595.3.

Example 55

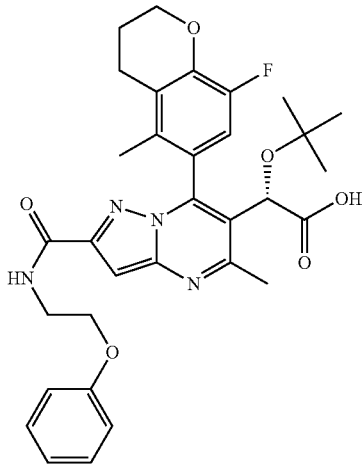 [SMILES: Cc1nc2cc(C(=O)NCCOc3ccccc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((2-phenoxyethyl)carbamoyl)pyrazolo[1,5-a]pyrimidin-6-yl)acetic acid $^1$H NMR (500 MHz, DMSO-d$_6$) δ: 8.27 (t, J=5.8 Hz, 1H), 7.97 (s, 1H), 7.31-7.26 (m, 2H), 7.07 (d, J=11.3 Hz, 1H), 7.01 (s, 1H), 6.97-6.92 (m, 3H), 4.73 (s, 1H), 4.26 (t, J=5.2 Hz, 2H), 4.09 (t, J=6.1 Hz, 2H), 3.65-3.56 (m, 2H), 2.74-2.68 (m, 5H), 2.10-2.02 (m, 2H), 1.79 (s, 3H), 1.06 (s, 9H). LCMS (M+H)=591.3.

Example 56

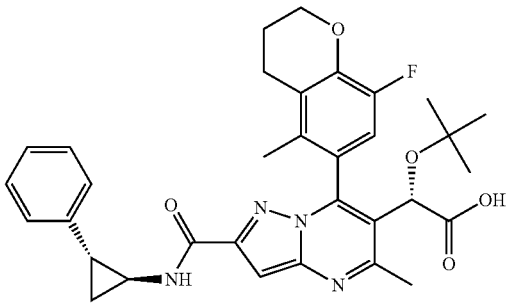 [SMILES: Cc1nc2cc(C(=O)N[C@H]3C[C@@H]3c3ccccc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(((1S,2R)-2-phenylcyclopropyl)carbamoyl)pyrazolo[1,5-a]pyrimidin-6-yl)acetic acid $^1$H NMR (500 MHz, DMSO-d$_6$) δ: 8.53-8.50 (m, 1H), 7.97 (s, 1H), 7.30-7.25 (m, 2H), 7.20-7.14 (m, 3H), 7.05 (d, J=11.3 Hz, 1H), 7.02 (s, 0.5H), 7.01 (s, 0.5H), 4.70 (br. s., 1H), 4.29-4.23 (m, 2H), 2.97-2.93 (m, 1H), 2.74-2.69 (m, 5H), 2.15-2.03 (m, 3H), 1.80 (s, 1.5H), 1.79 (s, 1.5H), 1.41-1.34 (m, 1H), 1.24-1.20 (m, 1H), 1.06 (s, 4.5H), 1.06 (s, 4.5H). LCMS (M+H)=587.3.

Example 57

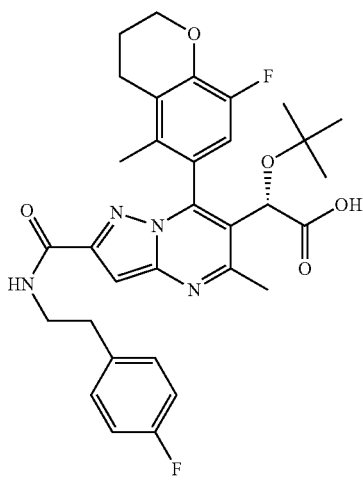 [SMILES: Cc1nc2cc(C(=O)NCCc3ccc(F)cc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-((4-fluorophenethyl)carbamoyl)-5-methylpyrazolo[1,5-a]pyrimidin-6-yl)acetic acid $^1$H NMR (500 MHz, DMSO-d$_6$) δ: 8.11 (t, J=6.0 Hz, 1H), 7.97 (s, 1H), 7.27-7.20 (m, 2H), 7.12-7.05 (m, 3H), 6.97 (s, 1H), 4.75 (s, 1H), 4.27 (t, J=5.2 Hz, 2H), 3.47-3.42 (m, 2H), 2.80 (t, J=7.3 Hz, 2H), 2.74-2.68 (m, 5H), 2.11-2.04 (m, 2H), 1.78 (s, 3H), 1.06 (s, 9H). LCMS (M+H)=593.3.

Example 58

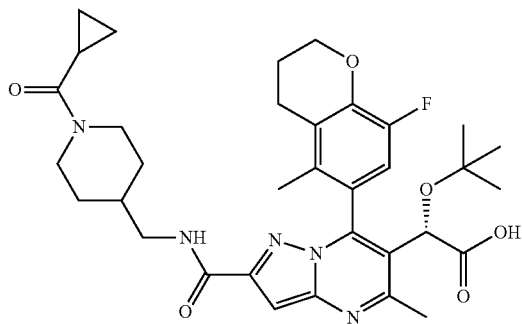 [SMILES: Cc1nc2cc(C(=O)NCC3CCN(C(=O)C4CC4)CC3)nn2c(-c2cc(F)c3c(c2C)CCCO3)c1[C@H](OC(C)(C)C)C(=O)O]

(2S)-2-(tert-butoxy)-2-(2-(((1-(cyclopropanecarbonyl)piperidin-4-yl)methyl)carbamoyl)-7-(8-fluoro-5-methylchroman-6-yl)-5-methylpyrazolo[1,5-a]pyrimidin-6-yl)acetic acid ¹H NMR (500 MHz, CHLOROFORM-d) δ 7.17 (s, 1H), 7.04 (br. s., 1H), 6.90 (d, J=10.7 Hz, 1H), 5.05 (s, 1H), 4.61 (d, J=12.8 Hz, 1H), 4.41-4.32 (m, 2H), 4.23 (d, J=11.0 Hz, 1H), 3.44-3.25 (m, 2H), 3.14-3.03 (m, 1H), 2.77 (s, 3H), 2.60 (d, J=12.2 Hz, 2H), 2.25-2.15 (m, 2H), 1.98 (s, 1H), 1.88 (s, 3H), 1.83 (d, J=11.3 Hz, 1H), 1.75 (br. s., 2H), 1.25 (br. s., 1H), 1.21 (s, 9H), 1.15 (d, J=13.4 Hz, 1H), 0.97 (br. s., 2H), 0.75 (d, J=5.5 Hz, 2H). LCMS (M+H)=636.6.

Example 59

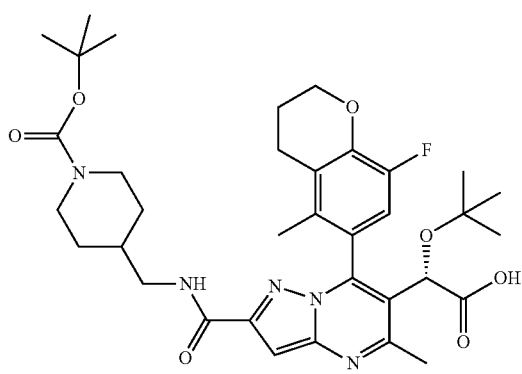 [SMILES: Cc1nc2cc(C(=O)NCC3CCN(C(=O)OC(C)(C)C)CC3)nn2c(-c2cc(F)c3c(c2C)CCCO3)c1[C@H](OC(C)(C)C)C(=O)O]

(2S)-2-(tert-butoxy)-2-(2-(((1-(tert-butoxycarbonyl)piperidin-4-yl)methyl)carbamoyl)-7-(8-fluoro-5-methylchroman-6-yl)-5-methylpyrazolo[1,5-a]pyrimidin-6-yl)acetic acid ¹H NMR (500 MHz, CHLOROFORM-d) δ 7.16 (s, 1H), 7.01 (t, J=6.1 Hz, 1H), 6.90 (d, J=10.7 Hz, 1H), 5.05 (s, 1H), 4.41-4.32 (m, 2H), 4.11 (br. s., 2H), 3.28-3.00 (m, 3H), 2.89 (br. s., 1H), 2.76 (s, 3H), 2.68 (br. s., 2H), 2.24-2.15 (m, 2H), 1.87 (s, 3H), 1.78 (br. s., 1H), 1.68 (d, J=11.3 Hz, 2H), 1.45 (s, 9H), 1.20 (s, 9H), 1.19-1.08 (m, 2H). LCMS (M+H)=668.6.

Example 60

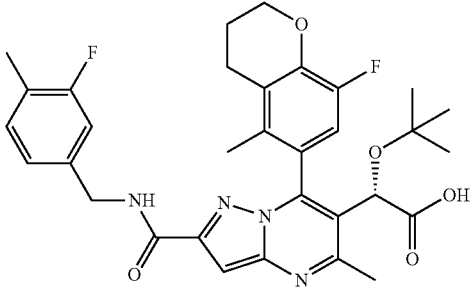

(2S)-2-(tert-butoxy)-2-(2-((3-fluoro-4-methylbenzyl)carbamoyl)-7-(8-fluoro-5-methylchroman-6-yl)-5-methylpyrazolo[1,5-a]pyrimidin-6-yl)acetic acid ¹H NMR (500 MHz, CHLOROFORM-d) δ 7.28-7.25 (m, 1H), 7.19 (s, 1H), 7.13 (t, J=7.8 Hz, 1H), 7.01-6.94 (m, 2H), 6.87 (d, J=10.7 Hz, 1H), 5.02 (s, 1H), 4.63-4.53 (m, 2H), 4.33 (t, J=4.4 Hz, 2H), 2.76 (s, 3H), 2.75-2.70 (m, 2H), 2.26 (s, 3H), 2.19-2.12 (m, 2H), 1.85 (s, 3H), 1.19 (s, 9H). LCMS (M+H)=593.5.

Example 61

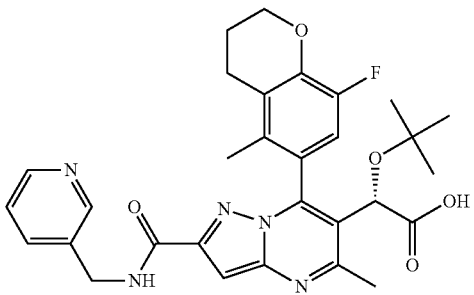 [SMILES: Cc1nc2cc(C(=O)NCc3cccnc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((pyridin-3-ylmethyl)carbamoyl)pyrazolo[1,5-a]pyrimidin-6-yl)acetic acid ¹H NMR (500 MHz, DMSO-d₆) δ: 8.80 (t, J=6.3 Hz, 1H), 8.52 (d, J=1.8 Hz, 1H), 8.45 (dd, J=4.9, 1.5 Hz, 1H), 7.70 (dt, J=7.9, 2.0 Hz, 1H), 7.35 (ddd, J=7.8, 4.7, 0.9 Hz, 1H), 7.08 (d, J=11.3 Hz, 1H), 7.03 (s, 1H), 4.76 (br. s., 1H), 4.46 (d, J=7.3

Hz, 2H), 4.26 (t, J=5.2 Hz, 2H), 2.74-2.68 (m, 5H), 2.09-2.02 (m, 2H), 1.79 (s, 3H), 1.06 (s, 9H). LCMS (M+H)=562.3.

Example 62

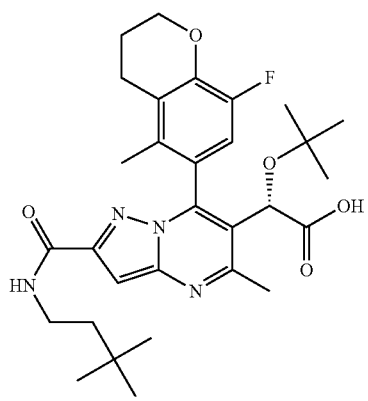 [SMILES: Cc1nc2cc(C(=O)NCCC(C)(C)C)nn2c(-c2cc(F)c3c(c2C)CCCO3)c1[C@H](OC(C)(C)C)C(=O)O]

(2S)-2-(tert-butoxy)-2-(2-((3,3-dimethylbutyl)carbamoyl)-7-(8-fluoro-5-methylchroman-6-yl)-5-methylpyrazolo[1,5-a]pyrimidin-6-yl)acetic acid ¹H NMR (500 MHz, DMSO-d₆) δ: 8.07 (t, J=5.8 Hz, 1H), 7.06 (d, J=11.3 Hz, 1H), 6.96 (s, 1H), 4.75 (s, 1H), 4.27 (t, J=5.6 Hz, 2H), 3.27-3.23 (m, 2H), 2.72 (t, J=6.6 Hz, 2H), 2.69 (s, 3H), 2.10-2.04 (m, 2H), 1.78 (s, 3H), 1.44-1.39 (m, 2H), 1.07 (s, 9H), 0.91 (s, 9H). LCMS (M+H)=555.3.

Example 63

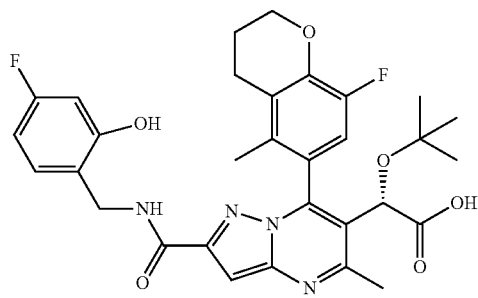 [SMILES: Cc1nc2cc(C(=O)NCc3ccc(F)cc3O)nn2c(-c2cc(F)c3c(c2C)CCCO3)c1[C@H](OC(C)(C)C)C(=O)O]

(2S)-2-(tert-butoxy)-2-(2-((4-fluoro-2-hydroxybenzyl)carbamoyl)-7-(8-fluoro-5-methylchroman-6-yl)-5-methylpyrazolo[1,4-a]pyrimidin-6yl)acetic acid ¹H NMR (500 MHz, DMSO-d₆) δ: 10.12 (s, 1H), 8.58 (t, J=6.1 Hz, 1H), 7.16-7.00 (m, 3H), 6.64-6.41 (m, 2H), 4.84 (s, 1H), 4.35 (d, J=6.4 Hz, 2H), 4.27 (t, J=5.3 Hz, 2H), 2.74-2.71 (m, 2H), 2.70 (s, 3H), 2.09-2.04 (m, 2H), 1.78 (s, 3H), 1.08 (s, 9H). LCMS (M+H)=595.4.

Example 64

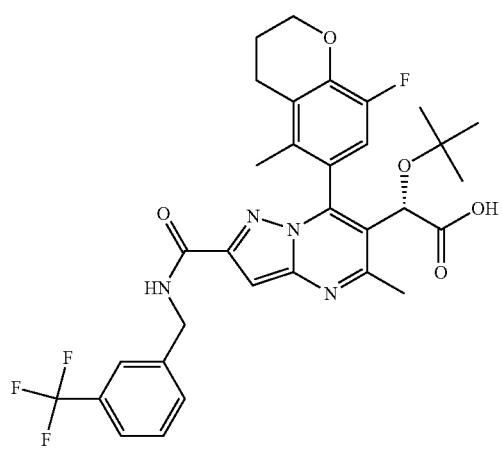 [SMILES: Cc1nc2cc(C(=O)NCc3cccc(C(F)(F)F)c3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-β-(trifluoromethyl)benzyl)carbamoyl)pyrazolo[1,5-a]pyrimidin-6-yl)acetic acid ¹H NMR (500 MHz, DMSO-d₆) δ: 8.86 (t, J=6.3 Hz, 1H), 7.65-7.59 (m, 3H), 7.59-7.54 (m, 1H), 7.13-7.11 (d, J=11.3 Hz, 1H), 7.06 (s, 1H), 4.84 (s, 1H), 4.52 (d, J=6.1 Hz, 2H), 4.26 (t, J=5.2 Hz, 2H), 2.74-2.69 (m, 5H), 2.10-2.02 (m, 2H), 1.78 (s, 3H), 1.08 (s, 9H). LCMS (M+H)=629.3.

Example 65

(2S)-2-(tert-butoxy)-2-(7-(8-fluoro-5-methylchroman-6-yl)-2-((4-methoxyphenethyl)carbamoyl)-5-methylpyrazolo[1,5-a]pyrimidin-6-yl)acetic acid ¹H NMR (500 MHz, DMSO-d₆) δ: 8.10 (t, J=6.0 Hz, 1H), 7.13-7.07 (m, 3H), 7.00 (s, 1H), 6.86-6.83 (m, 2H), 4.84 (s, 1H), 4.28 (t, J=5.6 Hz, 2H), 3.72 (s, 3H), 2.77-2.75 (m, 4H), 2.74-2.69 (m, 5H), 2.11-2.04 (m, 2H), 1.77 (s, 3H), 1.08 (s, 9H). LCMS (M+H)=605.3.

Example 66

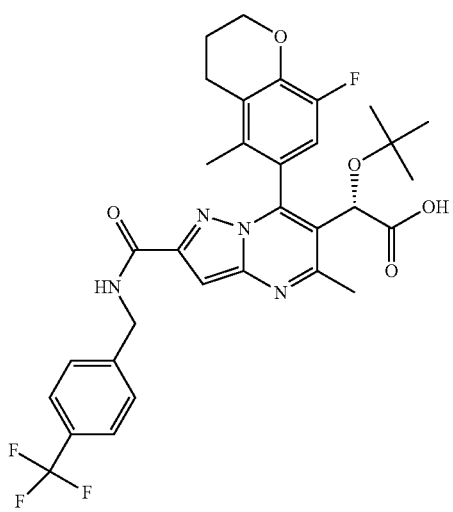 [SMILES: Cc1nc2cc(C(=O)NCc3ccc(C(F)(F)F)cc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((4-(trifluoromethyl)benzyl)carbamoyl)pyrazolo[1,5-a]pyrimidin-6-yl)acetic acid $^1$H NMR (400 MHz, DMSO-d$_6$) δ: 8.78 (t, J=6.3 Hz, 1H), 7.69 (d, J=8.0 Hz, 2H), 7.51 (d, J=8.0 Hz, 2H), 7.06 (d, J=11.3 Hz, 1H), 7.02 (s, 1H), 4.71 (s, 1H), 4.53 (d, J=6.3 Hz, 2H), 4.25 (t, J=5.1 Hz, 2H), 2.74-2.70 (m, 5H), 2.10-2.02 (m, 2H), 1.81 (s, 3H), 1.07 (s, 9H). LCMS (M+H)=629.3.

Example 67

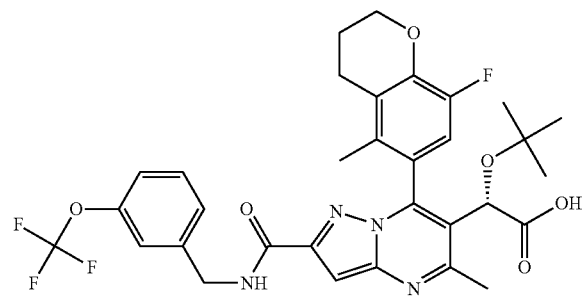 [SMILES: Cc1nc2cc(C(=O)NCc3cccc(OC(F)(F)F)c3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-β-(trifluoromethoxy)benzyl)carbamoyl)pyrazolo[1,5-a]pyrimidin-6-yl)acetic acid $^1$H NMR (500 MHz, DMSO-d$_6$) δ: 8.83 (t, J=6.3 Hz, 1H), 7.49-7.43 (m, 1H), 7.33 (d, J=7.9 Hz, 1H), 7.27-7.22 (m, 2H), 7.10 (d, J=12.2 Hz, 1H), 7.06 (s, 1H), 4.84 (s, 1H), 4.48 (d, J=6.4 Hz, 2H), 4.26 (t, J=5.2 Hz, 2H), 2.74-2.69 (m, 5H), 2.10-2.02 (m, 2H), 1.78 (s, 3H), 1.08 (s, 9H). LCMS (M+H)=645.3.

Example 68

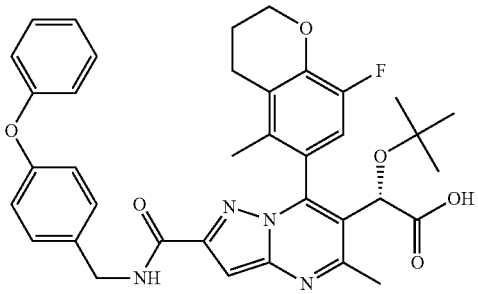 [SMILES: Cc1nc2cc(C(=O)NCc3ccc(Oc4ccccc4)cc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((4-phenoxybenzyl)carbamoyl)pyrazolo[1,5-a]pyrimidin-6-yl)acetic acid $^1$H NMR (500 MHz, DMSO-d$_6$) δ: 8.75 (t, J=6.3 Hz, 1H), 7.40-7.35 (m, 2H), 7.32 (d, J=8.5 Hz, 2H), 7.15-7.11 (m, 1H), 7.09 (d, J=11.0 Hz, 1H), 7.05 (s, 1H), 7.00-6.96 (m, 4H), 4.82 (s, 1H), 4.43 (dd, J=6.0, 3.5 Hz, 2H), 4.26 (t, J=5.2 Hz, 2H), 2.74-2.68 (m, 5H), 2.09-2.02 (m, 2H), 1.78 (s, 3H), 1.07 (s, 9H). LCMS (M+H)=653.4.

Example 69

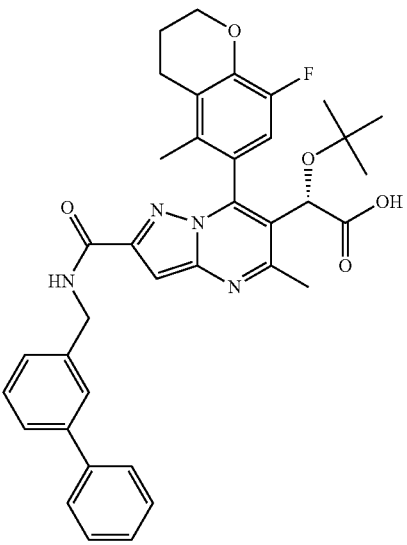 [SMILES: Cc1nc2cc(C(=O)NCc3cccc(-c4ccccc4)c3)nn2c(-c2cc(F)c3c(c2C)CCCO3)c1[C@H](OC(C)(C)C)C(=O)O]

(2S)-2-(2-(([1,1'-biphenyl]-3-ylmethyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-d$_6$) δ: 8.75 (br. s., 1H), 7.64-7.57 (m, 3H), 7.53 (d, J=7.6 Hz, 1H), 7.47 (t, J=7.8 Hz, 2H), 7.41 (t, J=7.6 Hz, 1H), 7.37 (t, J=7.6 Hz, 1H), 7.30 (d, J=7.6 Hz, 1H), 7.06 (d, J=11.6 Hz, 1H), 7.02 (s, 1H), 4.67 (br. s., 1H), 4.52 (d, J=6.4 Hz, 2H), 4.24 (br. s., 2H), 2.73-2.66 (m., 5H), 2.07-2.00 (m, 2H), 1.80 (s, 3H), 1.05 (s., 9H). LCMS (M+H)=637.3.

Example 70

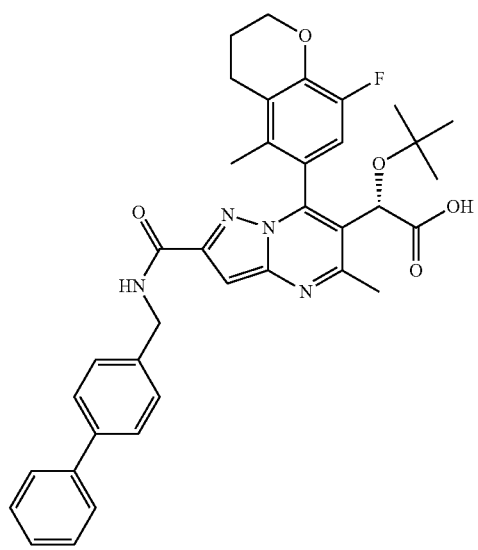 [SMILES: Cc1nc2cc(C(=O)NCc3ccc(-c4ccccc4)cc3)nn2c(-c2cc(F)c3c(c2C)CCCO3)c1[C@H](OC(C)(C)C)C(=O)O]

(2S)-2-(2-(((1,1'-biphenyl]-4-ylmethyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-$d_6$) δ: 8.79 (t, J=6.3 Hz, 1H), 7.67-7.59 (m, 4H), 7.48-7.44 (m, 2H), 7.41-7.33 (m, 3H), 7.10 (d, J=11.0 Hz, 1H), 7.07 (s, 1H), 4.83 (s, 1H), 4.49 (d, J=6.4 Hz, 2H), 4.26 (t, J=5.2 Hz, 2H), 2.74-2.69 (m, 5H), 2.09-2.03 (m, 2H), 1.79 (s, 3H), 1.08 (s, 9H). LCMS (M+H)=637.3.

Example 71

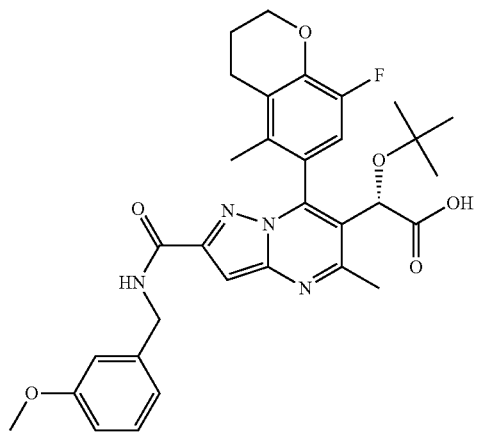 [SMILES: COc1cccc(CNC(=O)c2cc3nc(C)c([C@H](OC(C)(C)C)C(=O)O)c(-c4cc(F)c5c(c4C)CCCO5)n3n2)c1]

(2S)-2-(tert-butoxy)-2-(7-(8-fluoro-5-methylchroman-6-yl)-2-β-methoxybenzyl)carbamoyl)-5-methylpyrazolo[1,5-a]pyrimidin-6-yl)acetic acid $^1$H NMR (500 MHz, DMSO-$d_6$) δ: 8.68 (t, J=6.3 Hz, 1H), 7.23 (t, J=8.1 Hz, 1H), 7.06 (d, J=11.3 Hz, 1H), 7.02 (s, 1H), 6.86 (d, J=11.3 Hz, 1H), 6.85 (m, 1H), 6.83-6.78 (m, 1H), 4.68 (br. s., 1H), 4.41 (d, J=6.4 Hz, 2H), 4.25 (t, J=5.2 Hz, 2H), 3.72 (s, 3H), 2.74-2.68 (m, 5H), 2.09-2.00 (m, 2H), 1.80 (s, 3H), 1.06 (s, 9H). LCMS (M+H)=591.3.

Example 72

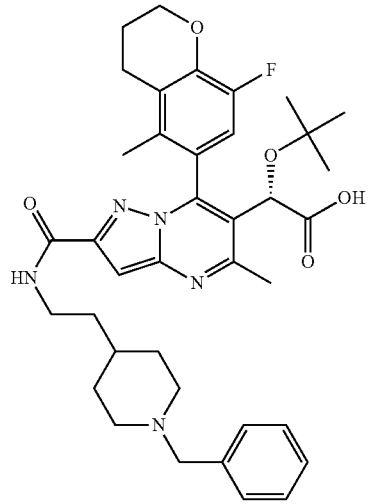 [SMILES: Cc1nc2cc(C(=O)NCCC3CCN(Cc4ccccc4)CC3)nn2c(-c2cc(F)c3c(c2C)CCCO3)c1[C@H](OC(C)(C)C)C(=O)O]

(2S)-2-(2-((2-(1-benzylpiperidin-4-yl)ethyl)carbamoyl)-7-(8-fluoro-5-methylchroman-6-yl)-5-methylpyrazolo[1,5-a]pyrimidin-6-yl)-2-(tert-butoxy) acetic acid $^1$H NMR (500 MHz, DMSO-$d_6$) δ: 8.09 (t, J=5.8 Hz, 1H), 7.34-7.27 (m, 4H), 7.27-7.22 (m, 1H), 7.05 (d, J=11.0 Hz, 1H), 6.96 (s, 1H), 4.70 (s, 1H), 4.26 (t, J=5.3 Hz, 2H), 3.46 (2, 2H), 3.27-3.22 (m, 2H), 2.81-2.76 (m, 2H), 2.73-2.68 (m, 5H), 2.09-2.03 (m, 2H), 1.95-1.87 (m, 2H), 1.78 (s, 3H), 1.68-1.62 (m, 2H), 1.45-1.39 (m, 2H), 2.28-1.21 (m, 1H), 1.19-1.09 (m, 2H), 1.06 (s, 9H) LCMS (M+H)=672.4.

Example 73

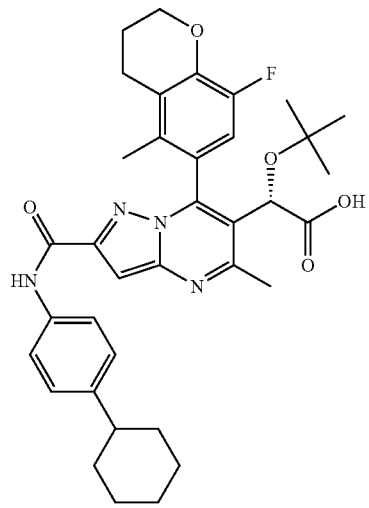 [SMILES: Cc1nc2cc(C(=O)Nc3ccc(C4CCCCC4)cc3)nn2c(-c2cc(F)c3c(c2C)CCCO3)c1[C@H](OC(C)(C)C)C(=O)O]

(2S)-2-(tert-butoxy)-2-(2-((4-cyclohexylphenyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 9.94 (s, 1H), 7.61 (d, J=8.2 Hz, 2H), 7.21 (d, J=8.2 Hz, 2H), 7.20 (s, 1H), 7.08 (d, J=11.3 Hz, 1H), 4.78 (s, 1H), 4.31-4.23 (m, 2H), 2.74-2.71 (m, 5H), 2.50-2.44 (m, 1H), 2.10-2.03 (m, 2H), 1.81 (s, 3H), 1.83-1.76 (m, 4H), 1.73-1.68 (m, 1H), 1.44-1.32 (m, 4H), 1.28-1.18 (m, 1H), 1.08 (s, 9H). LCMS (M+H)=629.4.

Example 74

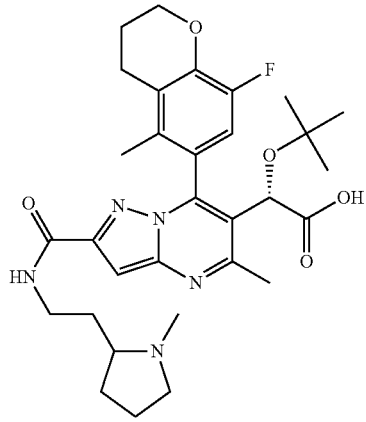 [SMILES: Cc1nc2cc(C(=O)NCCC3CCCN3C)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((2-(1-methylpyrrolidin-2-yl)ethyl)carbamoyl)pyrazolo[1,5-a]pyrimidin-6-yl)acetic acid $^1$H NMR (500 MHz, DMSO-d$_6$) δ: 8.56 (br. s., 1H), 7.06 (d, J=6.1 Hz, 0.5H), 7.04 (d, J=6.4 Hz, 0.5H), 6.93 (s, 0.5H), 6.92 (s, 0.5H), 4.68 (s, 1H), 4.25 (br. s., 2H), 2.73-2.57 (m, 7H), 2.46 (br. s., 1H), 2.31-2.20 (m, 5H), 2.11-1.93 (m, 4H), 1.77 (s, 1.5H), 1.76 (s, 1.5H), 1.71-1.48 (m, 4H), 1.05 (s, 9H). LCMS (M+H)=582.4.

Example 75

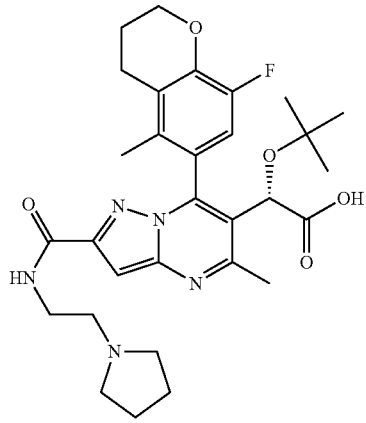 [SMILES: Cc1nc2cc(C(=O)NCCN3CCCC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((2-(pyrrolidin-1-yl)ethyl)carbamoyl)pyrazolo[1,5-a]pyrimidin-6-yl)acetic acid $^1$H NMR (500 MHz, DMSO-d$_6$) δ 8.15 (t, J=5.5 Hz, 1H), 7.05 (d, J=11.3 Hz, 1H), 6.95 (s, 1H), 4.72 (s, 1H), 4.25 (t, J=5.2 Hz, 2H), 2.73-2.68 (m, 8H), 2.65-2.60 (m, 5H), 2.10-2.02 (m, 2H), 1.78 (s, 3H), 1.72-1.67 (m, 4H), 1.06 (s, 9H). LCMS (M+H)=568.4.

Example 76

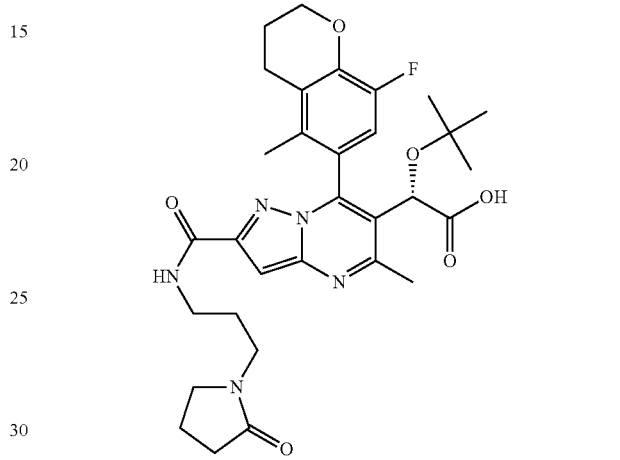

(2S)-2-(tert-butoxy)-2-(7-(8-fluoro-5-methylchroman-6-yl)-5-methyl-2-O-(2-oxopyrrolidin-1-yl)propyl)carbamoyl)pyrazolo[1,5-a]pyrimidin-6-yl)acetic acid $^1$H NMR (500 MHz, DMSO-d$_6$) δ: 8.15 (t, J=6.1 Hz, 1H), 7.06 (d, J=11.3 Hz, 1H), 6.98 (s, 1H), 4.80 (s, 1H), 4.30-4.24 (m, 2H), 3.25-3.12 (m, 6H), 2.74-2.68 (m, 5H), 2.22-2.17 (m, 2H), 2.10-2.03 (m, 2H), 1.95-1.87 (m, 2H), 1.78 (s, 3H), 1.69-1.64 (m, 2H), 1.08 (s, 9H). LCMS (M+H)=596.4.

Example 77

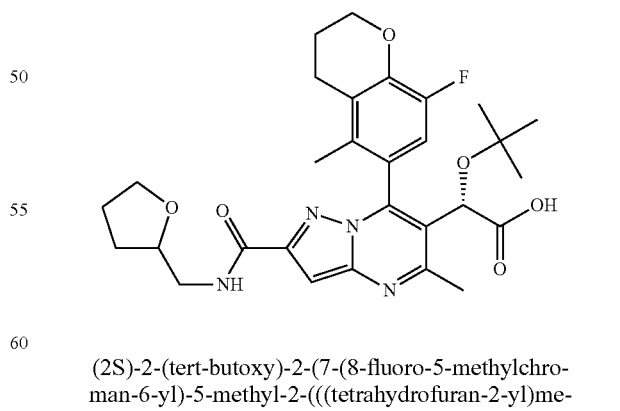

(2S)-2-(tert-butoxy)-2-(7-(8-fluoro-5-methylchroman-6-yl)-5-methyl-2-(((tetrahydrofuran-2-yl)methyl)carbamoyl)pyrazolo[1,5-a]pyrimidin-6-yl)acetic acid $^1$H NMR (500 MHz, DMSO-d$_6$) δ: 8.05-8.00 (m, 1H), 7.08 (d, J=11.3 Hz, 1H), 7.01 (s, 1H), 4.78 (s, 0.5H), 4.76 (s, 0.5H), 4.27 (t, J=5.2 Hz, 2H), 4.00-3.94 (m, 1H), 3.75-3.69 (m, 1H), 3.63-3.58 (m, 1H), 3.31-3.24 (m, 2H), 2.74-2.69 (m, 5H), 2.10-2.04 (m, 2H), 1.91-1.80 (m, 3H), 1.79 (s, 1.5H), 1.77 (s, 1.5H), 1.58-1.49 (m, 1H), 1.07 (s, 4.5H), 1.06 (s, 4.5H). LCMS (M+H)=555.4.

Example 78

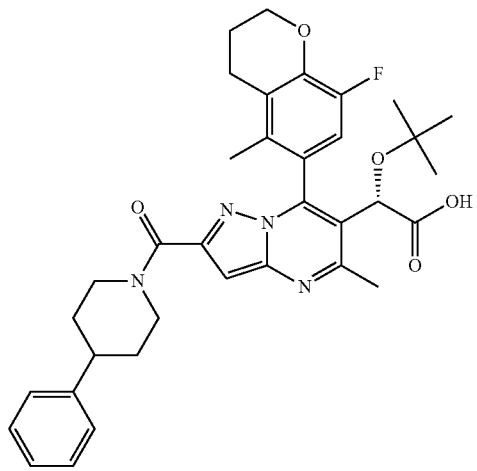

(2S)-2-(tert-butoxy)-2-(7-(8-fluoro-5-methylchroman-6-yl)-5-methyl-2-(4-phenylpiperidine-1-carbonyl)pyrazolo[1,5-a]pyrimidin-6-yl)acetic acid $^1$H NMR (500 MHz, DMSO-d$_6$) δ: 7.34-7.29 (m, 2H), 7.24-7.18 (m, 2H), 7.10-7.04 (m, 1H), 6.81 (d, J=15.0 Hz, 1H), 4.84 (br. s., 0.6H), 4.83 (br. s., 0.4H), 4.59 (t, J=11.9 Hz, 1H), 4.25-4.04 (m, 1H), 3.94 (d, J=11.9 Hz, 1H), 3.10-3.02 (m, 2H), 2.87-2.79 (m, 2H), 2.73-2.63 (m, 5H), 2.05-1.93 (m, 2H), 1.87-1.82 (m, 1H), 1.79 (s, 1.4H), 1.74 (s, 1.6H), 1.68-1.40 (m, 3H), 1.10 (s, 5H), 1.08 (s, 4H). LCMS (M+H)=615.4.

Example 79

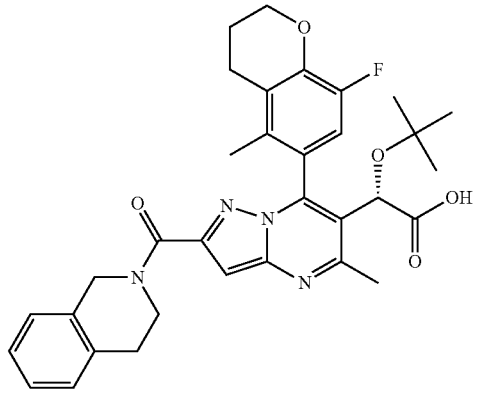 [SMILES: Cc1nc2cc(C(=O)N3CCc4ccccc4C3)nn2c(-c2cc(F)c3c(c2C)CCCO3)c1[C@H](OC(C)(C)C)C(=O)O]

Example 80

(2S)-2-(tert-butoxy)-2-(7-(8-fluoro-5-methylchroman-6-yl)-5-methyl-2-(1,2,3,4-tetrahydroisoquinoline-2-carbonyl)pyrazolo[1,5-a]pyrimidin-6-yl)acetic acid $^1$H NMR (500 MHz, DMSO-d$_6$) δ: 7.25-7.07 (m, 4H), 6.87 (d, J=6.1 Hz, 0.3H), 6.86 (s, 1H), 6.83 (d, J=7.3 Hz, 0.7H), 4.88-4.67 (m, 3H), 4.30-4.24 (m, 2H), 3.89-3.63 (m, 3H), 2.87 2.74-2.65 (m, 6H), 2.12-2.01 (m, 2H), 1.83 (s, 1H), 1.80 (s, 2H), 1.10 (s, 5H), 1.09 (s, 4H). LCMS (M+H)=587.4.

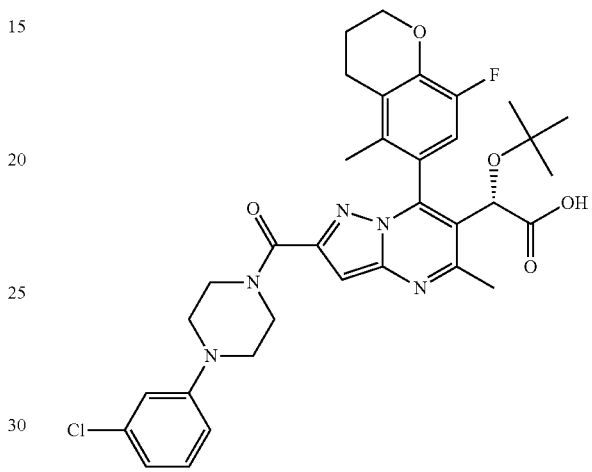

(2S)-2-(tert-butoxy)-2-(2-(4-(3-chlorophenyl)piperazine-1-carbonyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 7.24 (t, J=8.2 Hz, 1H), 7.08 (d, J=11.0 Hz, 1H), 6.95 (t, J=2.1 Hz, 1H), 6.89 (dd, J=8.5, 2.1 Hz, 1H), 6.85-6.81 (m, 2H), 4.82 (s, 1H), 4.28-4.20 (m, 2H), 3.81-3.75 (m, 1H), 3.72-3.55 (m, 3H), 3.27-3.09 (m, 3H), 3.03-2.97 (m, 1H), 2.74-2.70 (m, 5H), 2.11-1.98 (m, 2H), 1.80 (s, 3H), 1.09 (s, 9H). LCMS (M+H)=650.3 and 652.4.

Example 81

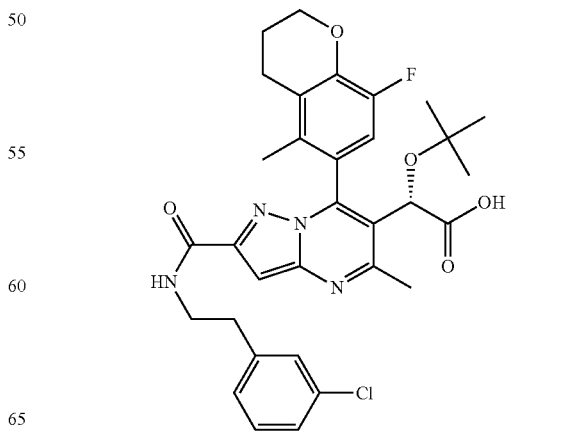

(2S)-2-(tert-butoxy)-2-(2-((3-chlorophenethyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.15 (t, J=6.0 Hz, 1H), 7.33-7.25 (m, 3H), 7.17 (d, J=7.6 Hz, 1H), 7.07 (d, J=11.0 Hz, 1H), 6.97 (s, 1H), 4.75 (s, 1H), 4.27 (t, J=5.6 Hz, 2H), 3.50-3.44 (m, 2H), 2.83 (t, J=7.3 Hz, 2H), 2.74-2.68 (m, 5H), 2.10-2.04 (m, 2H), 1.77 (s, 3H), 1.07 (s, 9H). LCMS (M+H)= 609.3 and 611.3.

Example 82

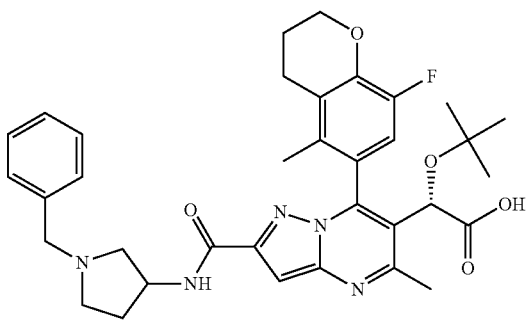 [SMILES: Cc1nc2cc(C(=O)NC3CCN(Cc4ccccc4)C3)nn2c(-c2cc(F)c3c(c2C)CCCO3)c1[C@H](OC(C)(C)C)C(=O)O]

(2S)-2-(2-((1-benzylpyrrolidin-3-yl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-d$_6$) δ: 8.20 (t, J=6.7 Hz, 1H), 7.34-7.28 (m, 4H), 7.27-7.23 (m, 1H), 7.08-7.04 (m, 2H), 4.77 (s, 1H), 4.41-4.34 (m, 1H), 4.26 (t, J=5.2 Hz, 2H), 3.64-3.57 (m, 4H), 2.74-2.66 (m, 5H), 2.50-2.43 (m, 2H), 2.19-2.11 (m, 1H), 2.09-2.02 (m, 2H), 1.77 (s, 3H), 1.07 (s, 9H). LCMS (M+H)=630.4.

Example 83

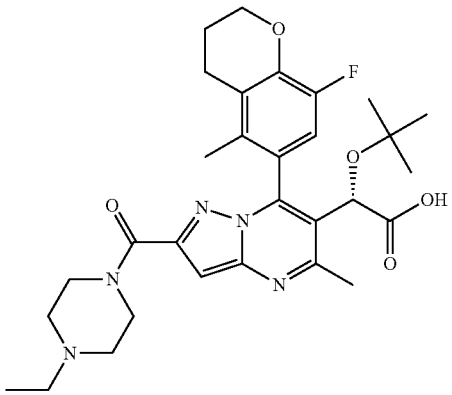 [SMILES: CCN1CCN(C(=O)c2cc3nc(C)c([C@H](OC(C)(C)C)C(=O)O)c(-c4cc(F)c5c(c4C)CCCO5)n3n2)CC1]

(2S)-2-(tert-butoxy)-2-(2-(4-ethylpiperazine-1-carbonyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 7.07 (d, J=11.3 Hz, 1H), 6.78 (s, 1H), 4.84 (s, 1H), 4.26 (t, J=5.2 Hz, 2H), 3.66-3.46 (m, 4H), 2.74-2.67 (m, 5H), 2.44-2.30 (m, 5H), 2.29-2.16 (m, 2H), 2.12-1.99 (m, 2H), 1.77 (s, 3H), 1.09 (s, 9H), 0.99 (t, J=7.2 Hz, 3H). LCMS (M+H)=568.4.

Example 84

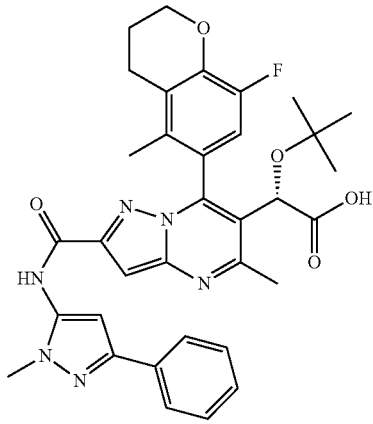 [SMILES: Cc1nc2cc(C(=O)Nc3cc(-c4ccccc4)nn3C)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((1-methyl-3-phenyl-1H-pyrazol-5-yl)carbamoyl)pyrazolo[1,5-a]pyrimidin-6-yl)acetic acid $^1$H NMR (500 MHz, DMSO-d$_6$) δ: 10.24 (br. s., 1H), 7.78 (d, J=7.6 Hz, 2H), 7.41 (t, J=7.6 Hz, 2H), 7.33-7.28 (m, 1H), 7.21 (s, 1H), 7.10 (d, J=11.0 Hz, 1H), 6.70 (s, 1H), 4.77 (br. s., 1H), 4.26 (t, J=5.3 Hz, 2H), 3.70 (s, 3H), 2.74 (s, 4H), 2.07 (br. s., 2H), 1.84 (s, 3H), 1.08 (s, 9H). LCMS (M+H)=627.5.

Example 85

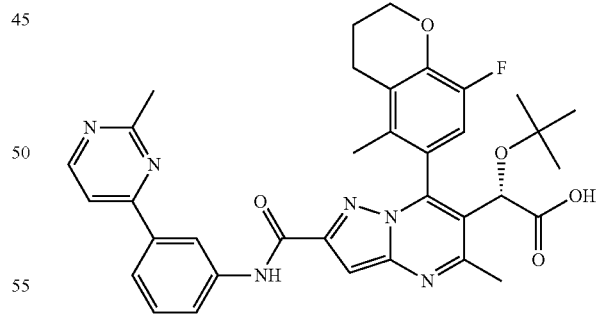

(2S)-2-(tert-butoxy)-2-(7-(8-fluoro-5-methylchroman-6-yl)-5-methyl-2-O-(2-methylpyrimidin-4-yl)phenyl)carbamoyl)pyrazolo[1,5-a]pyrimidin-6-yl)acetic acid $^1$H NMR (500 MHz, DMSO-d$_6$) δ: 8.77 (d, J=5.5 Hz, 1H), 8.55 (s, 1H), 7.98-7.95 (m, 2H), 7.91 (d, J=8.2 Hz, 1H), 7.83 (d, J=5.2 Hz, 1H), 7.53 (t, J=7.9 Hz, 1H), 7.19 (s, 1H), 7.02 (d, J=11.3 Hz, 1H), 4.47 (s, 1H), 4.28-4.23 (m, 2H), 2.75-2.71 (m, 5H), 2.70 (s, 3H), 2.10-2.03 (m, 2H), 1.90 (s, 3H), 1.05 (s, 9H). LCMS (M+H)=639.4.

Example 86

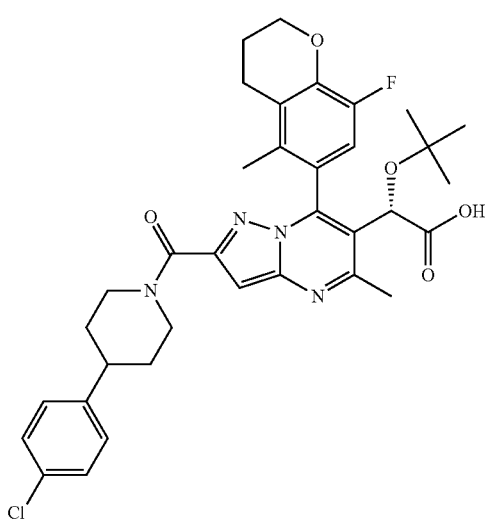 [SMILES: Cc1nc2cc(C(=O)N3CCC(c4ccc(Cl)cc4)CC3)nn2c(-c2cc(F)c3c(c2C)CCCO3)c1[C@H](OC(C)(C)C)C(=O)O]

(2S)-2-(tert-butoxy)-2-(2-(4-(4-chlorophenyl)piperidine-1-carbonyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 7.38-7.34 (m, 2H), 7.25 (dd, J=16.8, 8.2 Hz, 2H), 7.03-6.97 (m, 1H), 6.74-6.69 (m, 1H), 4.59 (br. s., 1H), 4.52 (s, 1H), 4.24-3.98 (m, 3H), 2.88-2.78 (m, 2H), 2.74 (2, 2H), 2.73 (d, 1H), 1.97-2.02 (m, 2H), 1.90-1.80 (m, 4H), 1.65-1.37 (m, 4H), 1.06 (s, 5H), 1.05 (s, 4H). LCMS (M+H)=649.4 and 650.4.

Example 87

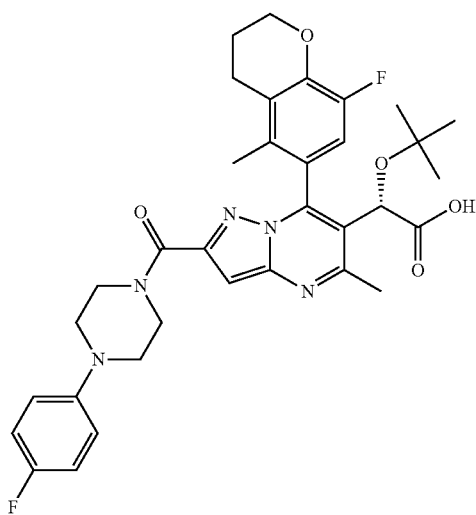 [SMILES: Cc1nc2cc(C(=O)N3CCN(c4ccc(F)cc4)CC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-(4-(4-fluorophenyl)piperazine-1-carbonyl)-5-methylpyrazolo[1,5-a]pyrimidin-6-yl)acetic acid $^1$H NMR (500 MHz, DMSO-d$_6$) δ: 7.12-7.05 (m, 3H), 7.00-6.93 (m, 2H), 6.82 (s, 1H), 4.80 (s, 1H), 4.29-4.15 (m, 2H), 3.80-3.59 (m, 5H), 3.16-3.05 (m, 3H), 3.03-2.94 (m, 2H), 2.72 (s, 3H), 2.12-1.96 (m, 2H), 1.80 (s, 3H), 1.09 (s, 9H). LCMS (M+H)=634.4.

Example 88

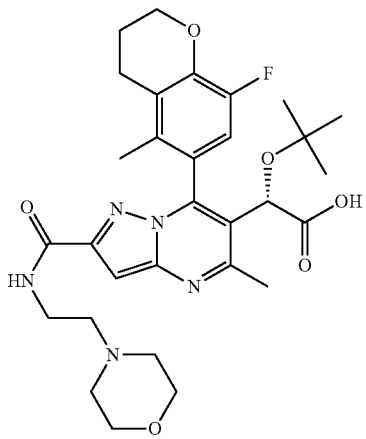 [SMILES: Cc1nc2cc(C(=O)NCCN3CCOCC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((2-morpholinoethyl)carbamoyl)pyrazolo[1,5-a]pyrimidin-6-yl)acetic acid $^1$H NMR (500 MHz, DMSO-d$_6$) δ: 7.95 (t, J=5.5 Hz, 1H), 7.09 (d, J=11.3 Hz, 1H), 6.97 (s, 1H), 4.78 (s, 1H), 4.26 (t, J=4.3 Hz, 2H), 3.51-3.49 (m, 6H), 2.74-2.67 (m, 5H), 2.47-2.32 (m, 6H), 2.12-2.02 (m, 2H), 1.79 (s, 3H), 1.07 (s, 9H). LCMS (M+H)=584.4.

Example 89

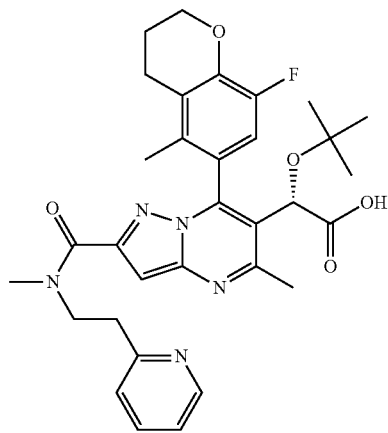 [SMILES: Cc1nc2cc(C(=O)N(C)CCc3ccccn3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(methyl(2-(pyridin-2-yl)ethyl)carbamoyl)pyrazolo[1,5-a]pyrimidin-6-yl)acetic acid ¹H NMR (500 MHz, DMSO-d₆) δ: 8.38 (d, J=4.3 Hz, 1H), 7.64 (td, J=7.6, 1.8 Hz, 1H), 7.20 (dd, J=7.2, 5.3 Hz, 1H), 7.09-7.03 (m, 1H), 7.00 (d, J=7.9 Hz, 1H), 6.67 (s, 1H), 4.80 (s, 1H), 4.26-4.12 (m, 3H), 3.78-3.68 (m, 3H), 2.90 (s, 3H), 2.85 (t, J=8.5 Hz, 2H), 2.71 (s, 3H), 2.09-1.95 (m, 2H), 1.73 (s, 2H), 1.08 (s, 9H). LCMS (M+H)=590.4.

Example 90

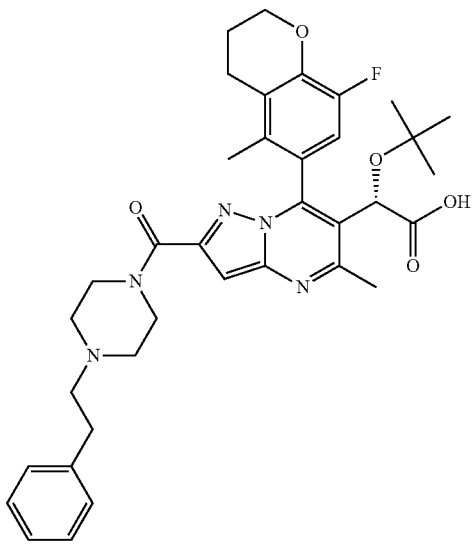 [SMILES: Cc1nc2cc(C(=O)N3CCN(CCc4ccccc4)CC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(4-phenethylpiperazine-1-carbonyl)pyrazolo[1,5-a]pyrimidin-6-yl)acetic acid ¹H NMR (500 MHz, DMSO-d₆) δ: 7.31-7.27 (m, 2H), 7.25-7.17 (m, 3H), 7.07 (d, J=11.3 Hz, 1H), 6.77 (s, 1H), 4.80 (s, 1H), 4.25 (t, J=5.2 Hz, 2H), 3.60-3.20 (m, 6H), 2.73-2.70 (m, 5H), 2.50-2.46 (m, 3H), 2.39-2.26 (m, 3H), 2.10-1.99 (m, 2H), 1.78 (s, 3H), 1.08 (s, 9H). LCMS (M+H)=644.4.

Example 91

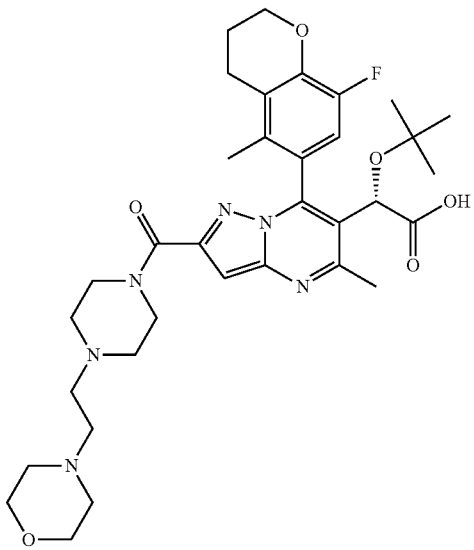 [SMILES: Cc1nc2cc(C(=O)N3CCN(CCN4CCOCC4)CC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(4-(2-morpholinoethyl)piperazine-1-carbonyl)pyrazolo[1,5-a]pyrimidin-6-yl)acetic acid ¹H NMR (500 MHz, DMSO-d₆) δ: 7.00 (d, J=11.6 Hz, 1H), 6.67 (s, 1H), 4.49 (s, 1H), 4.32-4.19 (m, 2H), 3.56 (t, J=4.6 Hz, 6H), 2.72 (s, 3H), 2.46-2.36 (m, 10H), 2.32-2.24 (m, 2H), 2.14-2.01 (m, 2H), 1.85 (s, 3H), 1.05 (s, 9H). LCMS (M+H)= 653.5.

Example 92

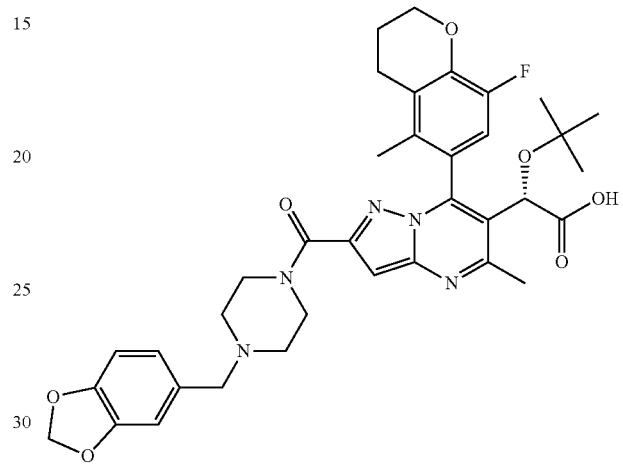

(2S)-2-(2-(4-(benzo[d][1,3]dioxol-5-ylmethyl)piperazine-1-carbonyl)-7-(8-fluoro-5-methylchroman-6-yl)-5-methylpyrazolo[1,5-a]pyrimidin-6-yl)-2-(tert-butoxy)acetic acid ¹H NMR (500 MHz, DMSO-d₆) δ: 7.06 (d, J=11.3 Hz, 1H), 6.88-6.83 (m, 2H), 6.77 (s, 1H), 6.74 (dd, J=8.1, 1.4 Hz, 1H), 6.00 (s, 2H), 4.82 (s, 1H), 4.30-4.20 (m, 2H), 3.65-3.50 (m, 5H), 2.70 (s, 3H), 2.68-2.60 (m, 2H), 2.42-2.30 (m, 3H), 2.26-2.14 (m, 2H), 2.09-1.97 (m, 2H), 1.74 (s, 3H), 1.08 (s, 9H). LCMS (M+H)=674.4.

Example 93

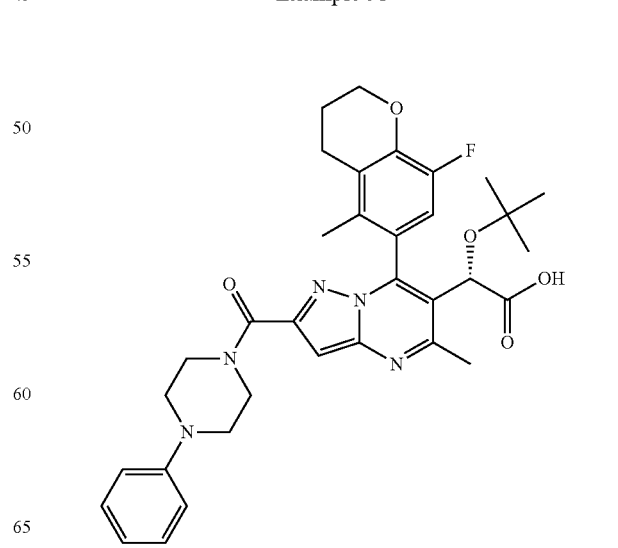

(2S)-2-(tert-butoxy)-2-(7-(8-fluoro-5-methylchroman-6-yl)-5-methyl-2-(4-phenylpiperazine-1-carbonyl)pyrazolo[1,5-a]pyrimidin-6-yl)acetic acid ¹H NMR (500 MHz, DMSO-d₆) δ: 7.27-7.21 (m, 2H), 7.09 (d, J=11.3 Hz, 1H), 6.93 (d, J=7.9 Hz, 2H), 6.85-6.80 (m, 2H), 4.82 (s, 1H), 4.29-4.17 (m, 2H), 3.82-3.68 (m, 2H), 3.67-3.58 (m, 2H), 3.25-3.11 (m, 4H), 3.08-2.93 (m, 2H), 2.72 (s, 3H), 2.12-1.96 (m, 2H), 1.80 (s, 3H), 1.09 (s, 9H). LCMS (M+H)=616.4.

Example 94

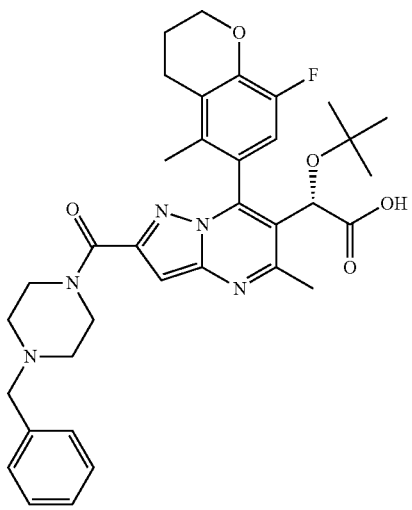

(2S)-2-(2-(4-benzylpiperazine-1-carbonyl)-7-(8-fluoro-5-methylchroman-6-yl)-5-methylpyrazolo[1,5-a]pyrimidin-6-yl)-2-(tert-butoxy)acetic acid ¹H NMR (500 MHz, DMSO-d₆) δ: 7.37-7.26 (m, 5H), 7.04 (d, J=11.3 Hz, 1H), 6.75 (s, 1H), 4.75 (s, 1H), 4.29-4.16 (m, 2H), 3.64-3.52 (m, 3H), 3.25-3.19 (m, 2H), 3.03-2.99 (m, 1H), 2.70 (s, 3H), 2.69-2.57 (m, 2H), 2.40-2.33 (m, 2H), 2.23-2.16 (m, 2H), 2.11-1.96 (m, 2H), 1.75 (s, 3H), 1.11 (s, 9H). LCMS (M+H)=630.4.

Example 95

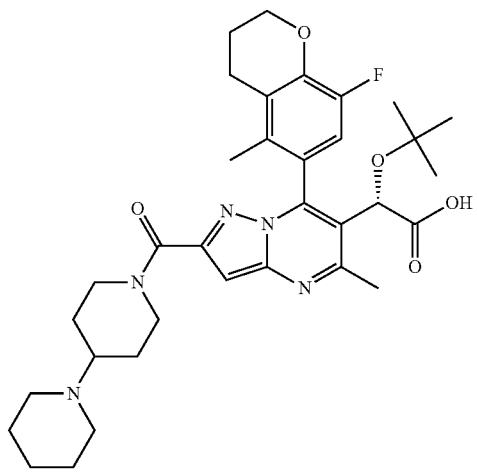 [SMILES: Cc1nc2cc(C(=O)N3CCC(N4CCCCC4)CC3)nn2c(-c2cc(F)c3c(c2C)CCCO3)c1[C@H](OC(C)(C)C)C(=O)O]

(2S)-2-(2-([1,4'-bipiperidine]-1'-carbonyl)-7-(8-fluoro-5-methylchroman-6-yl)-5-methylpyrazolo[1,5-a]pyrimidin-6-yl)-2-(tert-butoxy)acetic acid

LCMS (M+H)=622.4.

Example 96

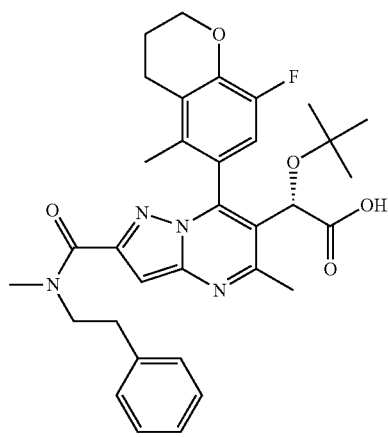

(2S)-2-(tert-butoxy)-2-(7-(8-fluoro-5-methylchroman-6-yl)-5-methyl-2-(methyl(phenethyl)carbamoyl)pyrazolo[1,5-a]pyrimidin-6-yl)acetic acid ¹H NMR (500 MHz, DMSO-d₆) δ: 7.33-7.25 (m, 2H), 7.24-7.16 (m, 2H), 7.07 (d, J=11.3 Hz, 1H), 6.95-6.90 (m, 1H), 6.76 (s, 0.3H), 6.67 (s, 0.7H), 4.83 (s, 1H), 4.26 (t, J=5.2 Hz, 1H), 4.23-4.17 (m, 1H), 4.15-4.08 (m, 1H), 3.70-3.53 (m, 4H), 2.90 (s, 3H), 2.88-2.81 (m, 1H), 2.71 (s, 2H), 2.71 (s., 1H), 2.03-1.95 (m, 1.5H), 1.92-1.85 (m, 0.5H), 1.78 (s, 1H), 1.74 (s, 2H), 1.09 (s, 9H). LCMS (M+H)=589.4.

Example 97

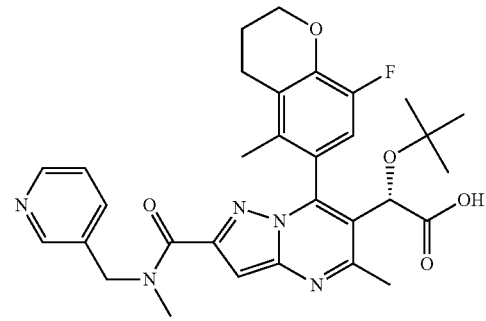 [SMILES: Cc1nc2cc(C(=O)N(C)Cc3cccnc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(methyl(pyridin-3-ylmethyl)carbamoyl)pyrazolo[1,5-a]pyrimidin-6-yl)acetic acid

LCMS (M+H)=576.3.

Example 98

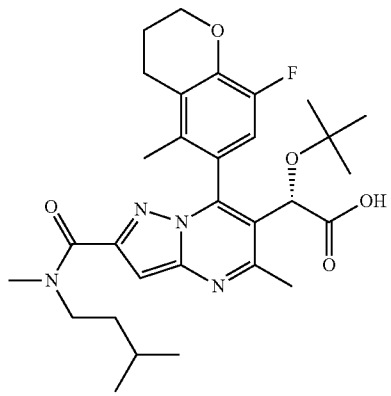 [SMILES: Cc1nc2cc(C(=O)N(C)CCC(C)C)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-(isopentyl(methyl)carbamoyl)-5-methylpyrazolo[1,5-a]pyrimidin-6-yl)acetic acid $^1$H NMR (500 MHz, DMSO-d$_6$) δ: 7.03 (d, J=11.0 Hz, 1H), 6.82 (s, 1H), 4.78 (s, 1H), 4.28-4.23 (m, 2H), 3.40 (s, 3H), 2.74-2.67 (m, 5H), 2.10-2.00 (m, 2H), 1.78 (s, 3H), 1.46-1.39 (m, 1H), 1.31-1.16 (m, 2H), 1.07 (s, 9H), 0.93-0.91 (m, 2H), 0.67 (d, J=2.7 Hz, 3H), 0.65 (d, J=2.7 Hz, 3H). LCMS (M+H)= 555.4.

Example 99

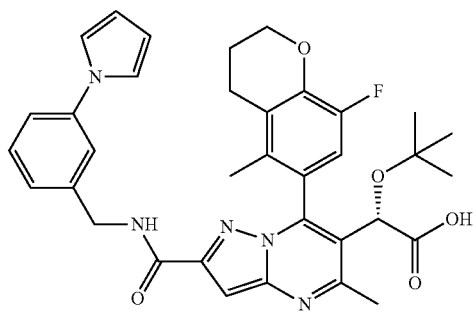 [SMILES: Cc1nc2cc(C(=O)NCc3cccc(-n4cccc4)c3)nn2c(-c2cc(F)c3c(c2C)CCCO3)c1[C@H](OC(C)(C)C)C(=O)O]

(2S)-2-(2-((3-(1H-pyrrol-1-yl)benzyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (400 MHz, CDCl$_3$) δ: 7.42-7.35 (m, 2H), 7.34-7.30 (m, 2H), 7.24-7.20 (m, 2H), 7.07 (t, J=2.1 Hz, 2H), 6.89 (d, J=10.8 Hz, 1H), 6.35 (t, J=2.1 Hz, 2H), 5.06 (s, 1H), 4.76-4.63 (m, 2H), 4.35-4.30 (m, 2H), 2.77 (s, 3H), 2.73 (d, J=3.3 Hz, 2H), 2.19-2.13 (m, 2H), 1.88 (s, 3H), 1.21 (s, 9H). LCMS (M+H)=626.5.

Example 100

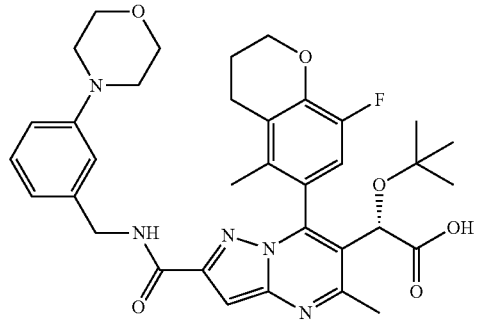 [SMILES: Cc1nc2cc(C(=O)NCc3cccc(N4CCOCC4)c3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-β-morpholinobenzyl)carbamoyl)pyrazolo[1,5-a]pyrimidin-6-yl)acetic acid $^1$H NMR (400 MHz, CDCl$_3$) δ: 7.28-7.15 (m, 3H), 6.93-6.80 (m, 4H), 5.06 (s, 1H), 4.69-4.52 (m, 2H), 4.38-4.29 (m, 2H), 3.89-3.79 (m, 4H), 3.18-3.11 (m, 4H), 2.79-2.74 (m, 2H), 2.74 (s, 3H), 2.23-2.13 (m, 2H), 1.90 (s, 3H), 1.21 (s, 9H). LCMS (M+H)=646.6.

Example 101

(2S)-2-(tert-butoxy)-2-(7-(8-fluoro-5-methylchroman-6-yl)-5-methyl-2-(((tetrahydro-2H-pyran-4-yl)methyl)carbamoyl)pyrazolo[1,5-a]pyrimidin-6-yl)acetic acid $^1$H NMR (400 MHz, CDCl$_3$) δ: 7.17 (s, 1H), 6.97 (t, J=6.5 Hz, 1H), 6.90 (d, J=10.5 Hz, 1H), 5.06 (s, 1H), 4.42-4.29 (m, 2H), 3.98 (dd, J=11.4, 4.1 Hz, 2H), 3.44-3.23 (m, 4H), 2.77 (s, 3H), 2.26-2.16 (m, 2H), 1.88 (s, 3H), 1.67-1.57 (m, 2H), 1.43-1.27 (m, 4H), 1.21 (s, 9H). LCMS (M+H)=569.5.

Example 102

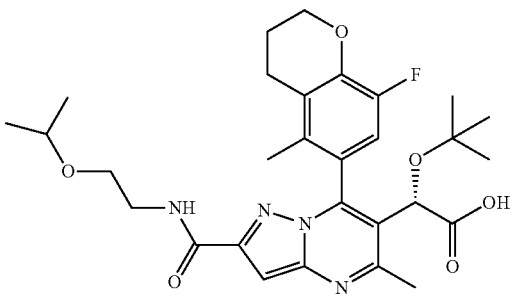 [SMILES: Cc1nc2cc(C(=O)NCCOC(C)C)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-((2-isopropoxyethyl)carbamoyl)-5-methylpyrazolo[1,5-a]pyrimidin-6-yl)acetic acid ¹H NMR (400 MHz, CDCl₃) δ: 7.33-7.29 (m, 1H), 7.16 (s, 1H), 6.88 (d, J=10.8 Hz, 1H), 5.07 (s, 1H), 4.38-4.30 (m, 2H), 3.67-3.47 (m, 5H), 2.79-2.76 (m, 2H), 2.76 (s, 3H), 2.23-2.15 (m, 2H), 1.89 (s, 3H), 1.22 (s, 9H), 1.09 (d, J=5.0 Hz, 3H), 1.11 (d, J=5.3 Hz, 3H). LCMS (M+H)=557.5.

Example 103

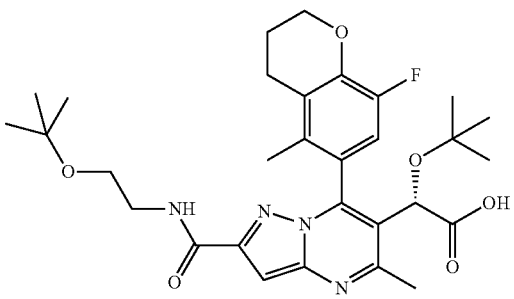 [SMILES: Cc1nc2cc(C(=O)NCCOC(C)(C)C)nn2c(-c2cc(F)c3c(c2C)CCCO3)c1[C@H](OC(C)(C)C)C(=O)O]

(2S)-2-(tert-butoxy)-2-(2-((2-(tert-butoxy)ethyl)carbamoyl)-7-(8-fluoro-5-methylchroman-6-yl)-5-methylpyrazolo[1,5-a]pyrimidin-6-yl)acetic acid ¹H NMR (400 MHz, CDCl₃) δ: 7.38-7.31 (m, 1H), 7.16 (s, 1H), 6.87 (d, J=10.8 Hz, 1H), 5.07 (s, 1H), 4.34 (dd, J=5.4, 3.9 Hz, 2H), 3.64-3.43 (m, 4H), 2.76 (s, 3H), 2.75-2.72 (m, 2H), 2.22-2.14 (m, 2H), 1.89 (s, 3H), 1.22 (s, 9H), 1.12 (s, 9H). LCMS (M+H)=571.5.

Example 104

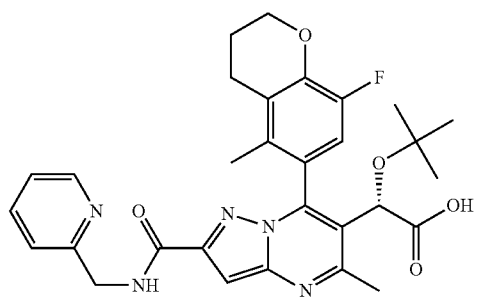 [SMILES: Cc1nc2cc(C(=O)NCc3ccccn3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((pyridin-2-ylmethyl)carbamoyl)pyrazolo[1,5-a]pyrimidin-6-yl)acetic acid ¹H NMR (500 MHz, DMSO-d₆) δ: 8.77 (t, J=6.0 Hz, 1H), 8.49 (d, J=4.3 Hz, 1H), 7.75 (td, J=7.6, 1.8 Hz, 1H), 7.31-7.25 (m, 2H), 7.10 (d, J=11.0 Hz, 1H), 7.05 (s, 1H), 4.81 (s, 1H), 4.59-4.49 (m, 2H), 4.26 (t, J=5.2 Hz, 2H), 2.74-2.70 (m, 5H), 2.10-2.02 (m, 2H), 1.80 (s, 3H), 1.08 (s, 9H). LCMS (M+H)=562.4.

Example 105

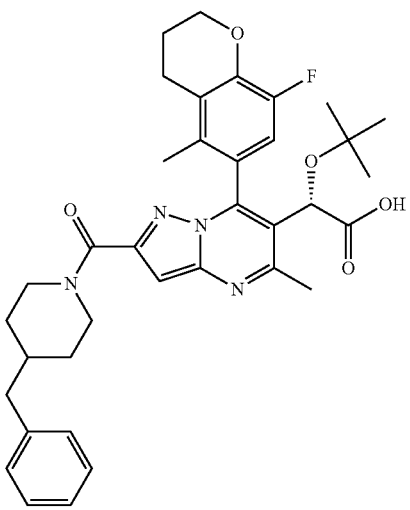 [SMILES: Cc1nc2cc(C(=O)N3CCC(Cc4ccccc4)CC3)nn2c(-c2cc(F)c3c(c2C)CCCO3)c1[C@H](OC(C)(C)C)C(=O)O]

(2S)-2-(2-(4-benzylpiperidine-1-carbonyl)-7-(8-fluoro-5-methylchroman-6-yl)-5-methylpyrazolo[1,5-a]pyrimidin-6-yl)-2-(tert-butoxy)acetic acid ¹H NMR (500 MHz, DMSO-d₆) δ: 7.64-7.62 (m, 0.6H), 7.60-7.54 (m, 0.4H), 7.32-7.26 (m, 2H), 7.22-7.14 (m, 3H), 7.07 (dd, J=11.1, 6.0 Hz, 1H), 6.76 (s, 0.4H), 6.75 (s, 0.6H), 4.86 (s, 0.6H), 4.84 (s, 0.4H), 4.45-4.38 (m, 1H), 4.30-4.22 (m, 2H), 3.94-3.86 (m, 1H), 2.90-2.85 (m, 1H), 2.73-2.62 (m, 6H), 2.55-2.54 (m, 4H), 2.11-1.99 (m, 2H), 1.77 (s, 1.2H), 1.72 (s, 1.8H), 1.67-1.62 (m, 1H), 1.45-1.39 (m, 1H), 1.10 (s, 5H), 1.08 (s, 4H). LCMS (M+H)=629.5.

Example 106

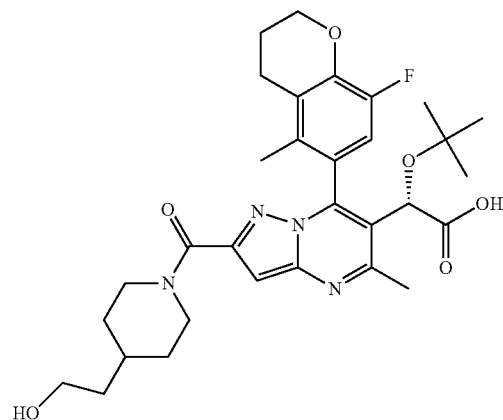 [SMILES: Cc1nc2cc(C(=O)N3CCC(CCO)CC3)nn2c(-c2cc(F)c3c(c2C)CCCO3)c1[C@H](OC(C)(C)C)C(=O)O]

75

(2S)-2-(tert-butoxy)-2-(7-(8-fluoro-5-methylchroman-6-yl)-2-(4-(2-hydroxyethyl)piperidine-1-carbonyl)-5-methylpyrazolo[1,5-a]pyrimidin-6-yl)acetic acid $^1$H NMR (500 MHz, DMSO-d$_6$) δ: 7.09-7.05 (m, 1H), 6.76 (s, 0.4H), 6.75 (s, 0.6H), 4.85 (br. s., 0.6H), 4.83 (br. s., 0.4H), 4.45-4.38 (m, 1H), 4.26 (t, J=5.0 Hz, 2H), 3.91-3.81 (m, 1H), 3.45-3.41 (m, 2H), 2.96-2.88 (m, 1H), 2.73-2.67 (m, 6H), 2.12-2.00 (m, 2H), 1.78 (s, 1.2H), 1.74 (s, 1.8H), 1.73-1.62 (m, 3H), 1.39-1.31 (m, 2H), 1.10 (s, 5H), 1.08 (s, 4H). LCMS (M+H)=583.4.

Example 107

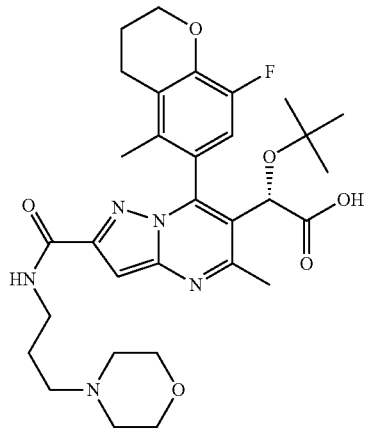 [SMILES: Cc1nc2cc(C(=O)NCCCN3CCOCC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-β-morpholinopropyl)carbamoyl)pyrazolo[1,5-a]pyrimidin-6-yl)acetic acid $^1$H NMR (500 MHz, DMSO-d$_6$) δ: 8.22 (t, J=5.6 Hz, 1H), 7.07 (d, J=11.3 Hz, 1H), 6.99 (s, 1H), 4.75 (s, 1H), 4.28-4.24 (m, 2H), 3.38-3.24 (m, 8H), 2.74-2.67 (m, 5H), 2.35-2.27 (m, 6H), 1.80 (s, 3H), 1.67-1.62 (m, 2H), 1.05 (s, 9H). LCMS (M+H)=598.4.

Example 108

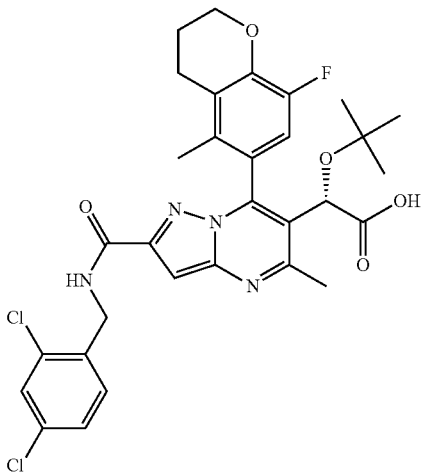 [SMILES: Cc1nc2cc(C(=O)NCc3ccc(Cl)cc3Cl)nn2c(-c2cc(F)c3c(c2C)CCCO3)c1[C@H](OC(C)(C)C)C(=O)O]

76

(2S)-2-(tert-butoxy)-2-(2-((2,4-dichlorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.75 (t, J=6.1 Hz, 1H), 7.62 (d, J=1.8 Hz, 1H), 7.41 (dd, J=8.4, 2.0 Hz, 1H), 7.29 (d, J=8.5 Hz, 1H), 7.08 (d, J=11.3 Hz, 1H), 7.05 (s, 1H), 4.73 (s, 1H), 4.48 (d, J=6.4 Hz, 2H), 4.25 (t, J=5.2 Hz, 2H), 2.74-2.68 (m, 5H), 2.09-2.01 (m, 2H), 1.80 (s, 3H), 1.07 (s, 9H). LCMS (M+H)=629.3 and 631.3.

Example 109

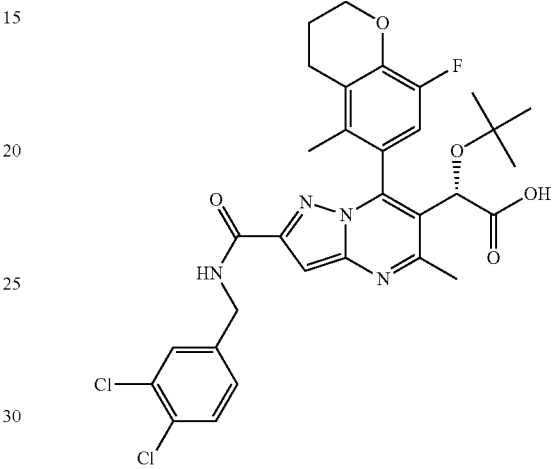

(2S)-2-(tert-butoxy)-2-(2-((3,4-dichlorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: $^1$H 8.80 (t, J=6.3 Hz, 1H), 7.60-7.57 (m, 1H), 7.53 (d, J=2.1 Hz, 1H), 7.29 (dd, J=8.2, 1.8 Hz, 1H), 7.09 (d, J=11.0 Hz, 1H), 7.04 (s, 1H), 4.77 (s, 1H), 4.43 (d, J=6.4 Hz, 2H), 4.26 (t, J=5.2 Hz, 2H), 2.74-2.69 (m, 5H), 2.10-2.02 (m, 2H), 1.79 (s, 3H), 1.07 (s, 9H). LCMS (M+H)=629.4 and 631.3.

Example 110

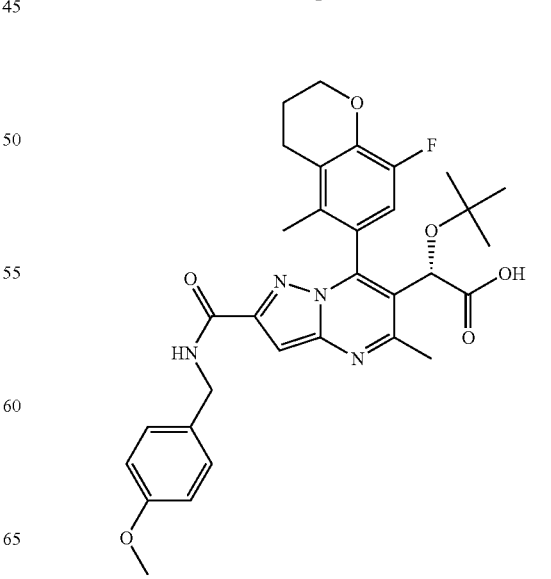

(2S)-2-(tert-butoxy)-2-(7-(8-fluoro-5-methylchroman-6-yl)-2-((4-methoxybenzyl)carbamoyl)-5-methylpyrazolo[1,5-a]pyrimidin-6-yl)acetic acid $^1$H NMR (500 MHz, DMSO-d$_6$) δ: 8.65 (t, J=6.1 Hz, 1H), 7.22 (d, J=8.9 Hz, 2H), 7.08 (d, J=11.3 Hz, 1H), 7.03 (s, 1H), 6.89-6.85 (m, 2H), 4.78 (s, 1H), 4.37 (d, J=6.7 Hz, 2H), 4.26 (t, J=5.2 Hz, 2H), 3.72 (s, 3H), 2.74-2.68 (m, 5H), 2.09-2.02 (m, 2H), 1.78 (s, 3H), 1.07 (s, 9H). LCMS (M+H)=591.4.

Example 111

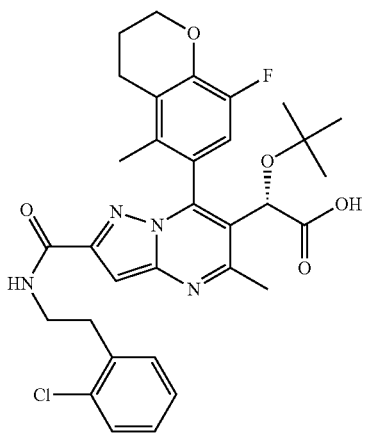 [SMILES: Cc1nc2cc(C(=O)NCCc3ccccc3Cl)nn2c(-c2cc(F)c3c(c2C)CCCO3)c1[C@H](OC(C)(C)C)C(=O)O]

(2S)-2-(tert-butoxy)-2-(2-((2-chlorophenethyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.18 (t, J=5.8 Hz, 1H), 7.43-7.39 (m, 1H), 7.33-7.29 (m, 1H), 7.28-7.22 (m, 2H), 7.07 (d, J=11.0 Hz, 1H), 6.97 (s, 1H), 4.77 (br. s., 1H), 4.27 (t, J=5.3 Hz, 2H), 3.52-3.46 (m, 2H), 2.95 (t, J=7.3 Hz, 2H), 2.73-2.67 (m, 5H), 2.11-2.03 (m, 2H), 1.78 (s, 3H), 1.07 (s, 9H). LCMS (M+H)=609.3 and 611.3.

Example 112

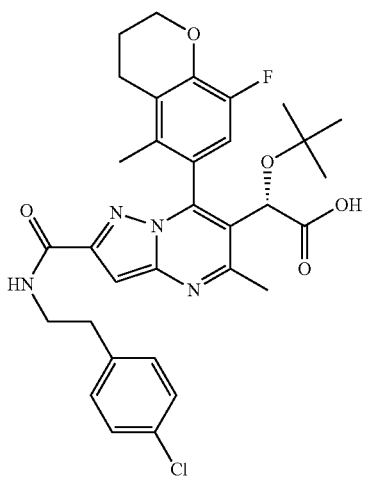 [SMILES: Cc1nc2cc(C(=O)NCCc3ccc(Cl)cc3)nn2c(-c2cc(F)c3c(c2C)CCCO3)c1[C@H](OC(C)(C)C)C(=O)O]

(2S)-2-(tert-butoxy)-2-(2-((4-chlorophenethyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.12 (t, J=6.0 Hz, 1H), 7.34-7.31 (m, 2H), 7.23 (d, J=8.5 Hz, 2H), 7.07 (d, J=11.3 Hz, 1H), 6.97 (s, 1H), 4.76 (s, 1H), 4.27 (t, J=5.3 Hz, 2H), 3.49-3.42 (m, 2H), 2.81 (t, J=7.3 Hz, 2H), 2.74-2.68 (m, 5H), 2.10-2.04 (m, 2H), 1.78 (s, 3H), 1.07 (s, 9H). LCMS (M+H)=609.4 and 611.4.

Example 113

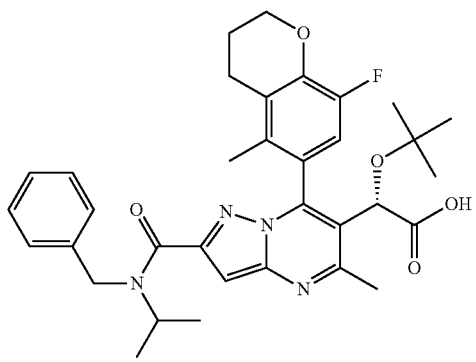 [SMILES: Cc1nc2cc(C(=O)N(Cc3ccccc3)C(C)C)nn2c(-c2cc(F)c3c(c2C)CCCO3)c1[C@H](OC(C)(C)C)C(=O)O]

(2S)-2-(2-(benzyl(isopropyl)carbamoyl)-7-(8-fluoro-5-methylchroman-6-yl)-5-methylpyrazolo[1,5-a]pyrimidin-6-yl)-2-(tert-butoxy)acetic acid $^1$H NMR (500 MHz, DMSO-d$_6$) δ: 7.31 (d, J=4.3 Hz, 2H), 7.24-7.17 (m, 3H), 7.09 (d, J=11.0 Hz, 0.5H), 6.94 (d, J=11.0 Hz, 0.5H), 6.87 (s, 0.5H), 6.86 (s, 0.5H), 4.87 (s, 0.5H), 4.75 (s, 0.5H), 4.73-4.57 (m, 2H), 4.34-4.21 (m, 3H), 2.74-2.65 (m, 4H), 2.09-1.98 (m, 2H), 1.79 (s, 1.5H), 1.48 (s, 1.5H), 1.10 (s, 4.5H), 1.08 (dd, J=6.9, 2.9 Hz, 3H), 1.06 (s, 4.5H), 0.97 (dd, J=6.4, 4.3 Hz, 3H). LCMS (M+H)=603.5.

Example 114

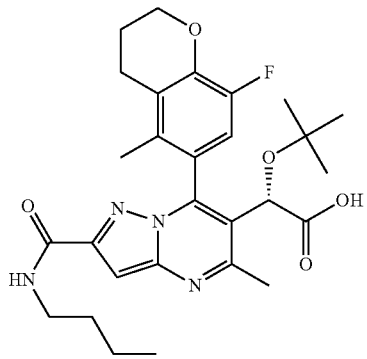 [SMILES: CCCCNC(=O)c1cc2nc(C)c([C@H](OC(C)(C)C)C(=O)O)c(-c3cc(F)c4c(c3C)CCCO4)n2n1]

(2S)-2-(tert-butoxy)-2-(2-(butylcarbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.11 (t, J=6.0 Hz, 1H), 7.06 (d, J=11.3 Hz, 1H), 6.98 (s, 1H), 4.74 (s, 1H), 4.27 (t, J=5.5 Hz, 2H), 3.25-3.20 (m, 2H), 2.74-2.68 (m, 5H), 2.10-2.03 (m, 2H), 1.78 (s, 3H), 1.50-1.44 (m, 2H), 1.32-1.25 (m, 2H), 1.06 (s, 9H), 0.89 (t, J=7.3 Hz, 3H). LCMS (M+H)=527.4.

Example 115

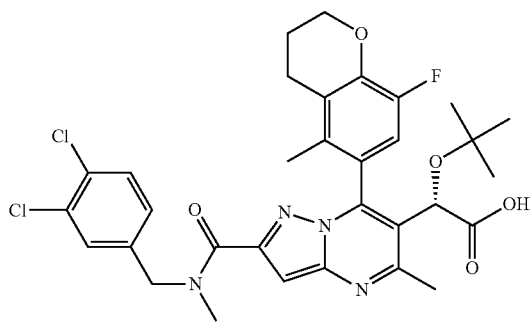 [SMILES: Cc1nc2cc(C(=O)N(C)Cc3ccc(Cl)c(Cl)c3)nn2c(-c2cc(F)c3c(c2C)CCCO3)c1[C@H](OC(C)(C)C)C(=O)O]

(2S)-2-(tert-butoxy)-2-(2-((3,4-dichlorobenzyl)(methyl)carbamoyl)-7-(8-fluoro-5-methylchroman-6-yl)-5-methylpyrazolo[1,5-a]pyrimidin-6-yl)acetic acid LCMS (M+H)=643.4 and 645.4.

Example 116

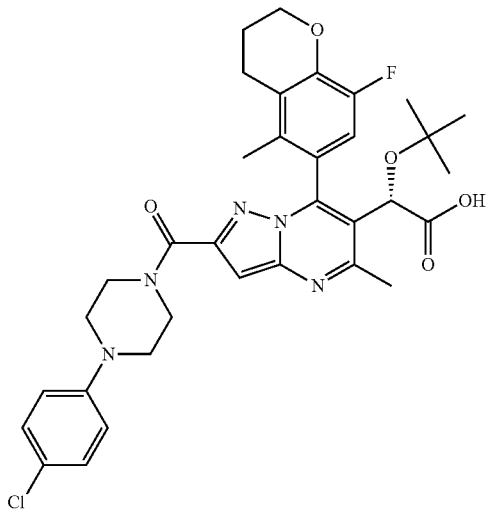 [SMILES: Cc1nc2cc(C(=O)N3CCN(c4ccc(Cl)cc4)CC3)nn2c(-c2cc(F)c3c(c2C)CCCO3)c1[C@H](OC(C)(C)C)C(=O)O]

(2S)-2-(tert-butoxy)-2-(2-(4-(4-chlorophenyl)piperazine-1-carbonyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 7.67-7.55 (m, 1H), 7.26 (d, J=9.2 Hz, 2H), 7.07 (d, J=11.3 Hz, 1H), 6.94 (d, J=9.2 Hz, 2H), 6.81 (s, 1H), 4.77 (s, 1H), 4.28-4.19 (m, 2H), 3.81-3.57 (m, 4H), 3.24-3.12 (m, 2H), 3.09-2.93 (m, 2H), 2.74-2.68 (m, 5H), 2.11-1.97 (m, 2H), 1.80 (s, 3H), 1.08 (s, 9H). LCMS (M+H)=650.5 and 651.5.

Example 117

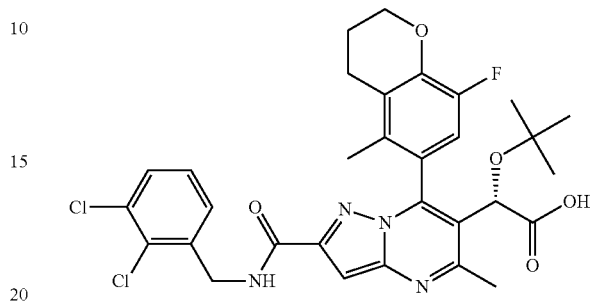

(2S)-2-(tert-butoxy)-2-(2-((2,3-dichlorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.79 (t, J=6.1 Hz, 1H), 7.56 (dd, J=7.9, 1.2 Hz, 1H), 7.35 (t, J=7.8 Hz, 1H), 7.25 (d, J=7.9 Hz, 1H), 7.09 (d, J=11.0 Hz, 1H), 7.07 (s, 1H), 4.78 (s, 1H), 4.54 (d, J=6.1 Hz, 2H), 4.25 (t, J=5.0 Hz, 2H), 2.74-2.68 (m, 5H), 2.09-2.01 (m, 2H), 1.80 (s, 3H), 1.07 (s, 9H). LCMS (M+H)=629.3 and 631.3.

Example 118

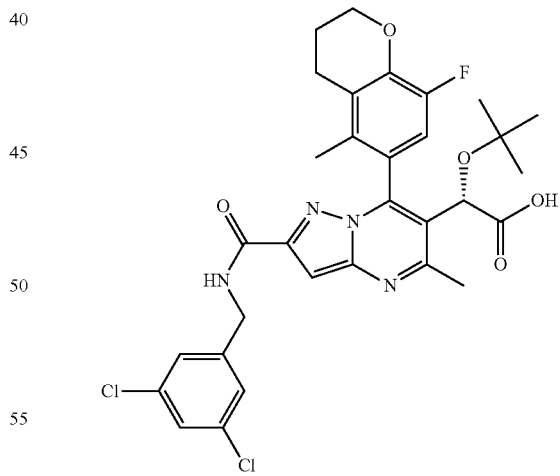

(2S)-2-(tert-butoxy)-2-(2-((3,5-dichlorobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.81 (t, J=6.3 Hz, 1H), 7.49 (t, J=2.0 Hz, 1H), 7.33 (d, J=1.8 Hz, 2H), 7.09 (d, J=11.3 Hz, 1H), 7.04 (s, 1H), 4.74 (s, 1H), 4.43 (d, J=6.1 Hz, 2H), 4.26 (t, J=5.2 Hz, 2H), 2.74-2.68 (m, 5H), 2.10-2.01 (m, 2H), 1.80 (s, 3H), 1.06 (s, 9H). LCMS (M+H)=629.3 and 631.3.

Example 119

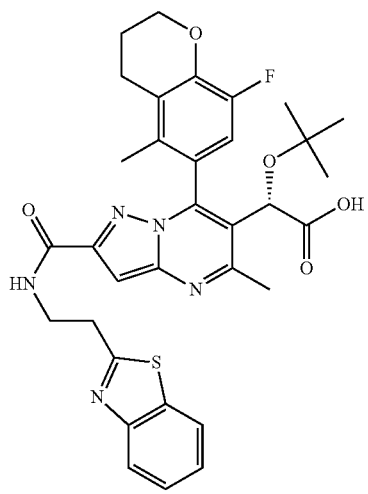 [SMILES: Cc1nc2cc(C(=O)NCCc3nc4ccccc4s3)nn2c(-c2cc(F)c3c(c2C)CCCO3)c1[C@H](OC(C)(C)C)C(=O)O]

(2S)-2-(2-((2-(benzo[d]thiazol-2-yl)ethyl)carbamoyl)-7-(8-fluoro-5-methylchroman-6-yl)-5-methylpyrazolo[1,5-a]pyrimidin-6-yl)-2-(tert-butoxy) acetic acid $^1$H NMR (500 MHz, DMSO-d$_6$) δ: 8.36 (t, J=6.0 Hz, 1H), 8.06 (d, J=7.9 Hz, 1H), 7.91 (d, J=7.9 Hz, 1H), 7.53-7.48 (m, 1H), 7.45-7.40 (m, 1H), 7.08 (d, J=11.0 Hz, 1H), 6.99 (s, 1H), 4.76 (s, 1H), 4.26 (t, J=5.0 Hz, 2H), 3.76-3.68 (m, 2H), 3.38-3.34 (m, 2H), 2.72-2.62 (m, 5H), 2.10-1.98 (m, 2H), 1.77 (s, 3H), 1.07 (s, 9H). LCMS (M+H)=632.4.

Example 120

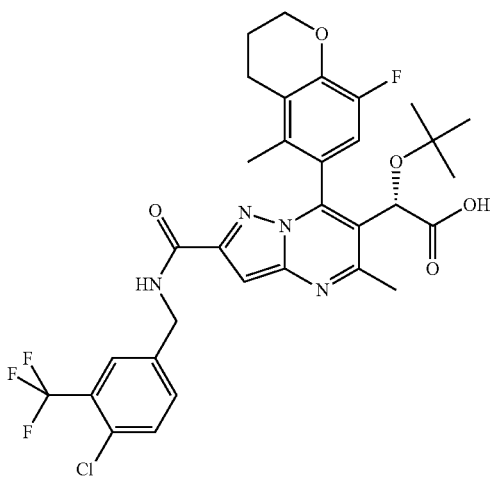 [SMILES: Cc1nc2cc(C(=O)NCc3ccc(Cl)c(C(F)(F)F)c3)nn2c(-c2cc(F)c3c(c2C)CCCO3)c1[C@H](OC(C)(C)C)C(=O)O]

(2S)-2-(tert-butoxy)-2-(2-((4-chloro-3-(trifluoromethyl)benzyl)carbamoyl)-7-(8-fluoro-5-methylchroman-6-yl)-5-methylpyrazolo[1,5-a]pyrimidin-6-yl) acetic acid $^1$H NMR (500 MHz, DMSO-d$_6$) δ: 8.84 (t, J=6.3 Hz, 1H), 7.78 (d, J=1.5 Hz, 1H), 7.69 (d, J=8.2 Hz, 1H), 7.62-7.59 (m, 1H), 7.08 (d, J=11.3 Hz, 1H), 7.03 (s, 1H), 4.76 (s, 1H), 4.49 (d, J=6.1 Hz, 2H), 4.26 (t, J=5.0 Hz, 2H), 2.74-2.68 (m, 5H), 2.10-2.01 (m, 2H), 1.79 (s, 3H), 1.06 (s, 9H). LCMS (M+H)=663.4 and 665.4.

Example 121

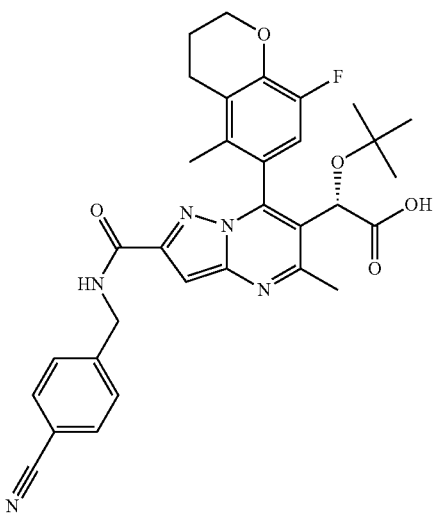 [SMILES: Cc1nc2cc(C(=O)NCc3ccc(C#N)cc3)nn2c(-c2cc(F)c3c(c2C)CCCO3)c1[C@H](OC(C)(C)C)C(=O)O]

(2S)-2-(tert-butoxy)-2-(2-((4-cyanobenzyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.83 (t, J=6.1 Hz, 1H), 7.79 (d, J=8.2 Hz, 2H), 7.47 (d, J=8.2 Hz, 2H), 7.08 (d, J=11.0 Hz, 1H), 7.03 (s, 1H), 4.73 (s, 1H), 4.51 (dd, J=6.1, 2.7 Hz, 2H), 4.25 (t, J=5.0 Hz, 2H), 2.74-2.68 (m, 5H), 2.10-2.01 (m, 2H), 1.80 (s, 3H), 1.06 (s, 9H). LCMS (M+H)=586.4.

Example 122

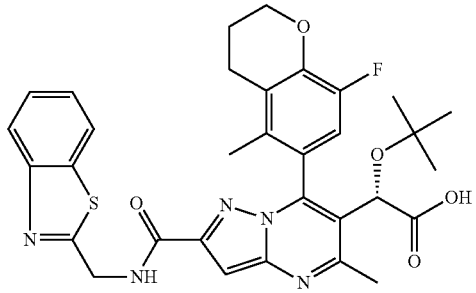 [SMILES: Cc1nc2cc(C(=O)NCc3nc4ccccc4s3)nn2c(-c2cc(F)c3c(c2C)CCCO3)c1[C@H](OC(C)(C)C)C(=O)O]

(2S)-2-(2-((benzo[d]thiazol-2-ylmethyl)carbamoyl)-7-(8-fluoro-5-methylchroman-6-yl)-5-methylpyrazolo[1,5-a]pyrimidin-6-yl)-2-(tert-butoxy)acetic acid ¹H NMR (500 MHz, DMSO-d₆) δ: 9.11 (t, J=6.0 Hz, 1H), 8.05 (d, J=7.9 Hz, 1H), 7.95 (d, J=7.9 Hz, 1H), 7.52-7.48 (m, 1H), 7.44-7.39 (m, 1H), 7.08 (d, J=11.3 Hz, 1H), 7.05 (s, 1H), 4.84 (dd, J=6.0, 2.6 Hz, 2H), 4.67 (br. s., 1H), 4.25 (t, J=5.2 Hz, 2H), 2.74-2.70 (m, 5H), 2.09-2.02 (m, 2H), 1.83 (s, 3H), 1.06 (s, 9H). LCMS (M+H)=618.4.

Example 123

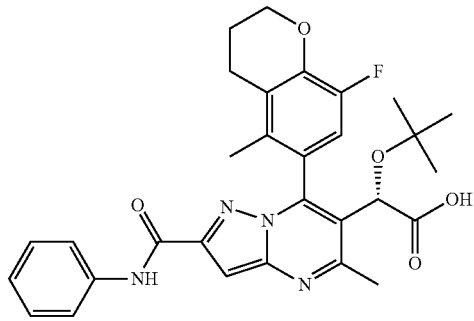 [SMILES: Cc1nc2cc(C(=O)Nc3ccccc3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(phenylcarbamoyl)pyrazolo[1,5-a]pyrimidin-6-yl)acetic acid ¹H NMR (500 MHz, DMSO-d₆) δ: 10.03 (s, 1H), 7.72 (d, J=7.9 Hz, 2H), 7.36 (t, J=7.9 Hz, 2H), 7.22 (s, 1H), 7.13 (t, J=7.3 Hz, 1H), 7.09 (d, J=11.3 Hz, 1H), 4.79 (s, 1H), 4.32-4.23 (m, 2H), 2.73 (s, 5H), 2.11-2.04 (m, 2H), 1.81 (s, 3H), 1.08 (s, 9H). LCMS (M+H)=547.5.

Example 124

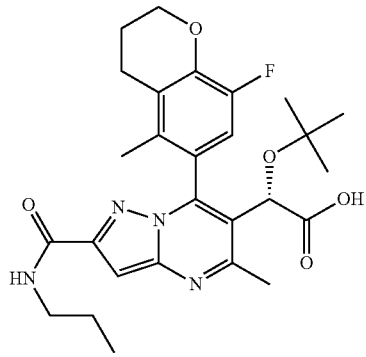 [SMILES: CCCNC(=O)c1cc2nc(C)c([C@H](OC(C)(C)C)C(=O)O)c(-c3cc(F)c4c(c3C)CCCO4)n2n1]

(2S)-2-(tert-butoxy)-2-(7-(8-fluoro-5-methylchroman-6-yl)-5-methyl-2-(propylcarbamoyl)pyrazolo[1,5-a]pyrimidin-6-yl)acetic acid ¹H NMR (500 MHz, DMSO-d₆) δ: 8.15 (t, J=6.0 Hz, 1H), 7.07 (d, J=11.3 Hz, 1H), 6.99 (s, 1H), 4.77 (s, 1H), 4.27 (t, J=5.6 Hz, 2H), 3.22-3.15 (m, 2H), 2.72 (t, J=6.7 Hz, 2H), 2.70 (s, 3H), 2.04-2.10 (m, 2H), 1.78 (s, 3H), 1.54-1.47 (m, 2H), 1.07 (s, 9H), 0.85 (t, J=7.5 Hz, 3H). LCMS (M+H)=513.4.

Example 125

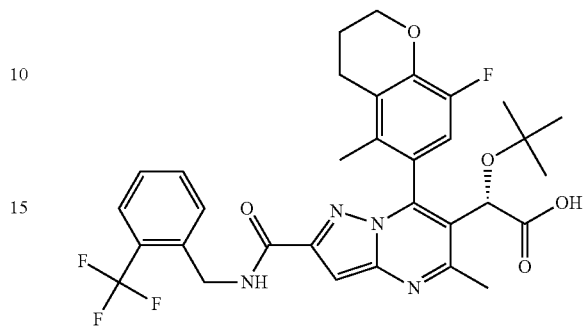

(2S)-2-(tert-butoxy)-2-(7-(8-fluoro-5-methylchroman-6-yl)-5-methyl-2-((2-(trifluoromethyl)benzyl)carbamoyl)pyrazolo[1,5-a]pyrimidin-6-yl)acetic acid ¹H NMR (500 MHz, DMSO-d₆) δ: 8.80 (t, J=6.1 Hz, 1H), 7.73 (d, J=7.6 Hz, 1H), 7.67-7.62 (m, 1H), 7.47 (t, J=7.6 Hz, 1H), 7.43 (d, J=7.6 Hz, 1H), 7.11 (d, J=11.3 Hz, 1H), 7.08 (s, 1H), 4.82 (s, 1H), 4.64 (d, J=6.1 Hz, 2H), 4.25 (t, J=5.0 Hz, 2H), 2.72 (s, 5H), 2.10-2.01 (m, 2H), 1.80 (s, 3H), 1.08 (s, 9H). LCMS (M+H)=629.4.

Example 126

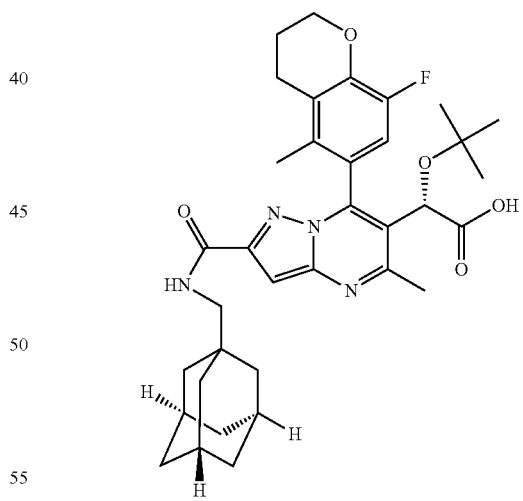

(2S)-2-(2-(((3S,5S,7S)-adamantan-1-ylmethyl)carbamoyl)-7-(8-fluoro-5-methylchroman-6-yl)-5-methylpyrazolo[1,5-a]pyrimidin-6-yl)-2-(tert-butoxy)acetic acid ¹H NMR (500 MHz, DMSO-d₆) δ: 7.85 (t, J=6.4 Hz, 1H), 7.08 (d, J=11.3 Hz, 1H), 7.05 (s, 1H), 4.86 (s, 1H), 4.26 (t, J=5.0 Hz, 2H), 3.02 (dd, J=13.1, 6.7 Hz, 1H), 2.94-2.87 (m, 1H), 2.73-2.67 (m, 5H), 2.12-2.00 (m, 2H), 1.91 (br. s., 3H), 1.77 (s, 3H), 1.68-1.62 (m, 3H), 1.60-1.53 (m, 3H), 1.44 (br. s., 7H), 1.08 (s, 9H). LCMS (M+H)=619.5.

Example 127

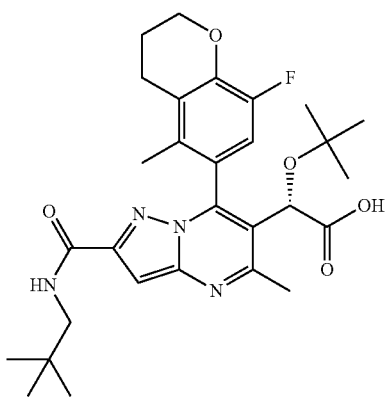 [SMILES: Cc1nc2cc(C(=O)NCC(C)(C)C)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-(neopentylcarbamoyl)pyrazolo[1,5-a]pyrimidin-6-yl)acetic acid $^1$H NMR (500 MHz, DMSO-d$_6$) δ: 7.92 (t, J=6.4 Hz, 1H), 7.09 (d, J=11.0 Hz, 1H), 7.06 (s, 1H), 4.83 (s, 1H), 4.26 (t, J=5.2 Hz, 2H), 3.16-3.10 (m, 1H), 3.07-3.00 (m, 1H), 2.74-2.66 (m, 5H), 2.11-2.02 (m, 2H), 1.77 (s, 3H), 1.08 (s, 9H), 0.86 (s, 9H). LCMS (M+H)=541.4.

Example 128

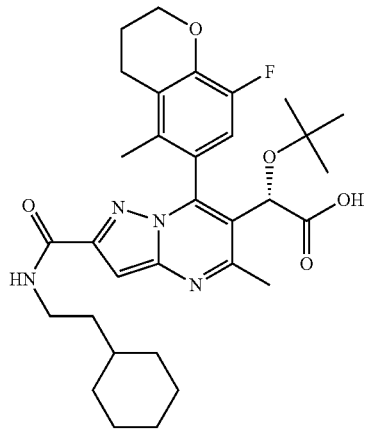 [SMILES: Cc1nc2cc(C(=O)NCCC3CCCCC3)nn2c(-c2cc(F)c3c(c2C)CCCO3)c1[C@H](OC(C)(C)C)C(=O)O]

(2S)-2-(tert-butoxy)-2-(2-((2-cyclohexylethyl)carbamoyl)-7-(8-fluoro-5-methylchroman-6-yl)-5-methylpyrazolo[1,5-a]pyrimidin-6-yl)acetic acid $^1$H NMR (500 MHz, DMSO-d$_6$) δ: 8.09 (t, J=5.8 Hz, 1H), 7.07 (d, J=11.0 Hz, 1H), 6.98 (s, 1H), 4.78 (s, 1H), 4.27 (t, J=5.3 Hz, 2H), 3.28-3.22 (m, 2H), 2.72 (t, J=6.7 Hz, 2H), 2.69 (s, 3H), 2.10-2.04 (m, 2H), 1.78 (s, 3H), 1.73-1.58 (m, 5H), 1.42-1.36 (m, 2H), 1.28-1.12 (m, 4H), 1.07 (s, 9H), 0.93-0.83 (m, 2H). LCMS (M+H)=581.5.

Example 129

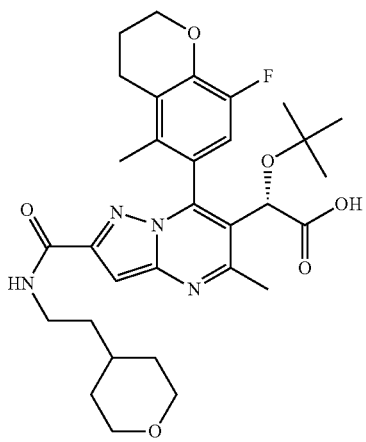

(2S)-2-(tert-butoxy)-2-(7-(8-fluoro-5-methylchroman-6-yl)-5-methyl-2-((2-(tetrahydro-2H-pyran-4-yl)ethyl)carbamoyl)pyrazolo[1,5-a]pyrimidin-6-yl) acetic acid $^1$H NMR (500 MHz, DMSO-d$_6$) δ: 8.12 (t, J=6.0 Hz, 1H), 7.06 (d, J=11.3 Hz, 1H), 6.97 (s, 1H), 4.74 (s, 1H), 4.26 (t, J=5.5 Hz, 2H), 3.81 (dd, J=11.1, 3.5 Hz, 2H), 3.30-3.21 (m, 4H), 2.72 (t, J=6.6 Hz, 2H), 2.70 (s, 3H), 2.10-2.04 (m, 2H), 1.78 (s, 3H), 1.59 (d, J=13.4 Hz, 2H), 1.53-1.41 (m, 3H), 1.19-1.10 (m, 2H), 1.06 (s, 9H). LCMS (M+H)=583.5.

Example 130

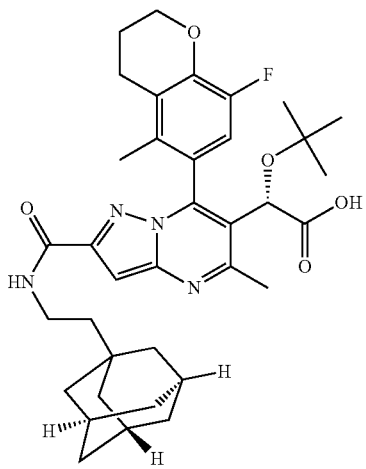 [SMILES: Cc1nc2cc(C(=O)NCCC34C[C@H]5C[C@@H](C3)C[C@@H](C4)C5)nn2c(-c2cc(F)c3c(c2C)CCCO3)c1[C@H](OC(C)(C)C)C(=O)O]

(2S)-2-(2-((2-(3S,5S,7S)-adamantan-1-yl)ethyl)carbamoyl)-7-(8-fluoro-5-methylchroman-6-yl)-5-methylpyrazolo[1,5-a]pyrimidin-6-yl)-2-(tert-butoxy) acetic acid $^1$H NMR (500 MHz, DMSO-d$_6$) δ: 8.03 (t, J=5.8 Hz, 1H), 7.07 (d, J=11.3 Hz, 1H), 6.97 (s, 1H), 4.80 (s, 1H), 4.27 (t, J=5.6 Hz, 2H), 3.27-3.22 (m, 2H), 2.74-2.70 (m, 2H), 2.69 (s, 3H), 2.10-2.04 (m, 2H), 1.92 (br. s., 2H), 1.77 (s, 3H), 1.71-1.58 (m, 7H), 1.50 (d, J=2.1 Hz, 6H), 1.31-1.26 (m, 2H), 1.07 (s, 9H). LCMS (M+H)=633.5.

Example 131

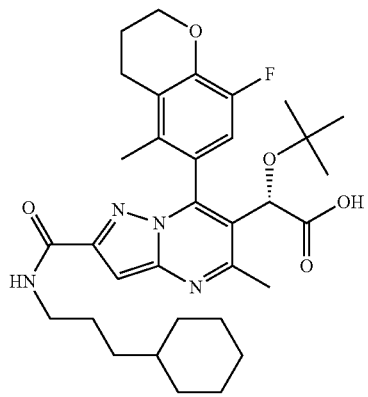 [SMILES: Cc1nc2cc(C(=O)NCCCC3CCCCC3)nn2c(-c2cc(F)c3c(c2C)CCCO3)c1[C@H](OC(C)(C)C)C(=O)O]

(2S)-2-(tert-butoxy)-2-(2-β-cyclohexylpropyl)carbamoyl)-7-(8-fluoro-5-methylchroman-6-yl)-5-methylpyrazolo[1,5-a]pyrimidin-6-yl)acetic acid ¹H NMR (500 MHz, DMSO-d₆) δ: 8.12 (t, J=6.0 Hz, 1H), 7.07 (d, J=11.0 Hz, 1H), 6.98 (s, 1H), 4.78 (s, 1H), 4.27 (t, J=5.5 Hz, 2H), 3.22-3.16 (m, 2H), 2.74-2.70 (m, 2H), 2.69 (s, 3H), 2.10-2.04 (m, 2H), 1.78 (s, 3H), 1.71-1.58 (m, 5H), 1.49 (dt, J=14.7, 7.4 Hz, 2H), 1.23-1.11 (m, 6H), 1.07 (s, 9H), 0.88-0.80 (m, 2H). LCMS (M+H)=595.5.

Example 132

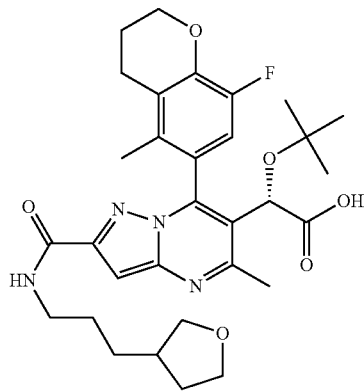 [SMILES: Cc1nc2cc(C(=O)NCCCC3CCOC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-5-methyl-2-((3-(tetrahydrofuran-3-yl)propyl)carbamoyl)pyrazolo[1,5-a]pyrimidin-6-yl)acetic acid ¹H NMR (500 MHz, DMSO-d₆) δ: 8.15 (t, J=6.0 Hz, 1H), 7.08 (d, J=11.3 Hz, 1H), 6.99 (s, 1H), 4.78 (s, 1H), 4.27 (t, J=5.3 Hz, 2H), 3.77 (t, J=7.6 Hz, 1H), 3.70 (td, J=8.2, 4.6 Hz, 1H), 3.60 (q, J=7.5 Hz, 1H), 3.22 (q, J=7.0 Hz, 2H), 3.18 (t, J=7.6 Hz, 1H), 2.74-2.71 (m, 2H), 2.70 (s, 3H), 2.15-2.04 (m, 3H), 2.00-1.93 (m, 1H), 1.78 (s, 3H), 1.56-1.29 (m, 5H), 1.07 (s, 9H). LCMS (M+H)=583.5.

Example 133

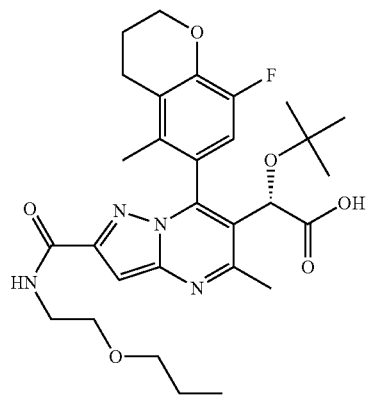 [SMILES: CCCOCCNC(=O)c1cc2nc(C)c([C@H](OC(C)(C)C)C(=O)O)c(-c3cc(F)c4c(c3C)CCCO4)n2n1]

(2S)-2-(tert-butoxy)-2-(7-(8-fluoro-5-methylchroman-6-yl)-5-methyl-2-((2-propoxyethyl)carbamoyl)pyrazolo[1,5-a]pyrimidin-6-yl)acetic acid ¹H NMR (500 MHz, DMSO-d₆) δ: 7.99 (t, J=5.8 Hz, 1H), 7.08 (d, J=11.3 Hz, 1H), 7.00 (s, 1H), 4.79 (s, 1H), 4.27 (t, J=5.2 Hz, 2H), 3.48-3.32 (m, 6H), 2.72 (t, J=7.3 Hz, 2H), 2.70 (s, 3H), 2.10-2.03 (m, 2H), 1.78 (s, 3H), 1.51-1.43 (m, 2H), 1.07 (s, 9H), 0.82 (t, J=7.3 Hz, 3H). LCMS (M+H)=557.5.

Example 134

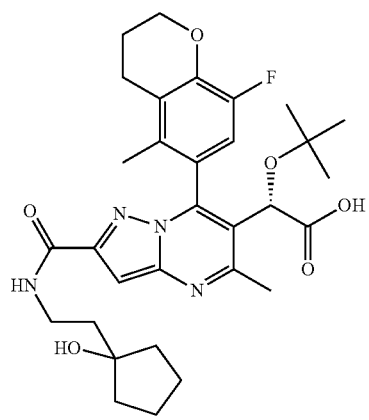 [SMILES: Cc1nc2cc(C(=O)NCCC3(O)CCCC3)nn2c(-c2cc(F)c3c(c2C)CCCO3)c1[C@H](OC(C)(C)C)C(=O)O]

(2S)-2-(tert-butoxy)-2-(7-(8-fluoro-5-methylchroman-6-yl)-2-((2-(1-hydroxycyclopentyl)ethyl)carbamoyl)-5-methylpyrazolo[1,5-a]pyrimidin-6-yl)acetic acid ¹H NMR (500 MHz, DMSO-d₆) δ: 8.11 (t, J=5.8 Hz, 1H), 7.06 (d, J=11.3 Hz, 1H), 6.97 (s, 1H), 4.81 (s, 1H), 4.29-4.24 (m, 2H), 4.18 (br. s., 1H), 2.74-2.71 (m, 2H), 2.70 (s, 3H), 2.10-2.04 (m, 2H), 1.77 (s, 3H), 1.74-1.67 (m, 4H), 1.60-1.41 (m, 8H), 1.08 (s, 9H). LCMS (M+H)=583.5.

Example 135

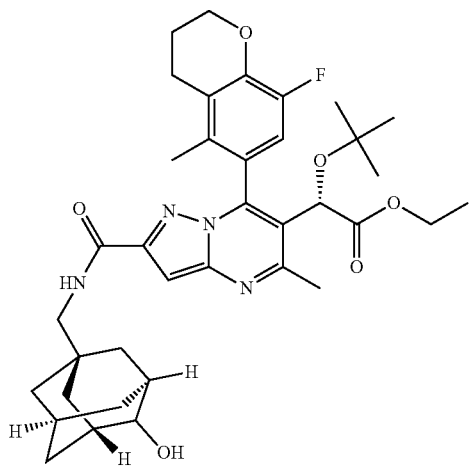 [SMILES: CCOC(=O)[C@@H](OC(C)(C)C)c1c(C)nc2cc(C(=O)NC[C@]34C[C@@H]5C[C@H](C3)C(O)[C@@H](C5)C4)nn2c1-c1cc(F)c2c(c1C)CCCO2]

(2S)-2-(tert-butoxy)-2-(7-(8-fluoro-5-methylchroman-6-yl)-2-((((1R,3R,4S,5R,7S)-4-hydroxyadamantan-1-yl)methyl)carbamoyl)-5-methylpyrazolo[1,5-a]pyrimidin-6-yl)acetic acid

LCMS (M+H)=635.5.

Example 136

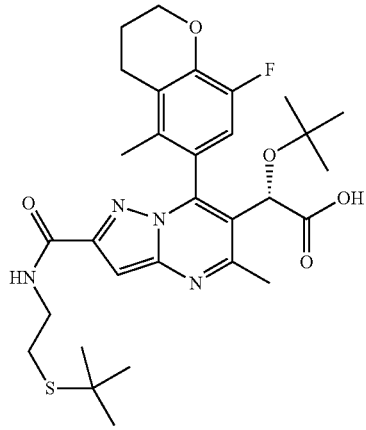 [SMILES: Cc1nc2cc(C(=O)NCCSC(C)(C)C)nn2c(-c2cc(F)c3c(c2C)CCCO3)c1[C@H](OC(C)(C)C)C(=O)O]

(2S)-2-(tert-butoxy)-2-(2-((2-(tert-butylthio)ethyl)carbamoyl)-7-(8-fluoro-5-methylchroman-6-yl)-5-methylpyrazolo[1,5-a]pyrimidin-6-yl)acetic acid $^1$H NMR (500 MHz, DMSO-$d_6$) δ: 8.23 (t, J=6.0 Hz, 1H), 7.08 (d, J=11.0 Hz, 1H), 6.99 (s, 1H), 4.78 (s, 1H), 4.27 (t, J=5.2 Hz, 2H), 3.45-3.26 (m, 2H), 2.74-2.71 (m, 2H), 2.70 (s, 3H), 2.68-2.63 (m, 2H), 2.10-2.04 (m, 2H), 1.78 (s, 3H), 1.27 (s, 9H), 1.07 (s, 9H). LCMS (M+H)=587.5.

Example 137

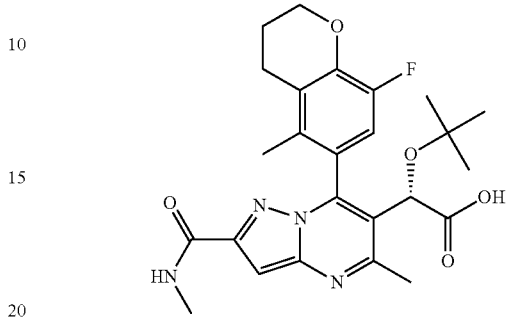

(2S)-2-(tert-butoxy)-2-(7-(8-fluoro-5-methylchroman-6-yl)-5-methyl-2-(methylcarbamoyl)pyrazolo[1,5-a]pyrimidin-6-yl)acetic acid $^1$H NMR (500 MHz, DMSO-$d_6$) δ: 8.01 (q, J=4.3 Hz, 1H), 7.03 (d, J=11.3 Hz, 1H), 6.92 (s, 1H), 4.64 (s, 1H), 4.26 (t, J=5.6 Hz, 2H), 2.75 (s, 3H), 2.74-2.68 (m, 5H), 2.10-2.04 (d, J=4.6 Hz, 2H), 1.81 (s, 3H), 1.05 (s, 8H). LCMS (M+H)=485.4.

Example 138

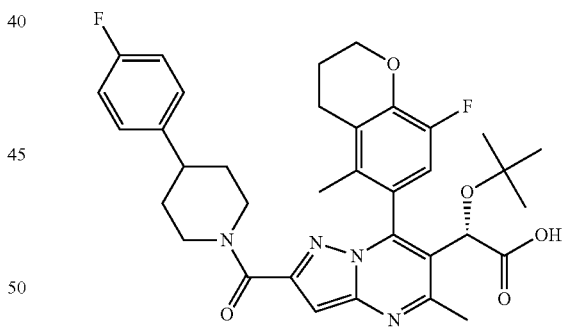

(S)-2-(tert-Butoxy)-2-((S)-7-(8-fluoro-5-methylchroman-6-yl)-2-(4-(4-fluorophenyl)piperidine-1-carbonyl)-5-methylpyrazolo[1,5-a]pyrimidin-6-yl)acetic acid $^1$H NMR (500 MHz, CDCl$_3$) δ 7.18-7.10 (m, 2H), 7.05-6.99 (m, 2H), 6.92 (d, J=12.8 Hz, 1.3H), 6.87 (d, J=12.3 Hz, 0.7H), 5.12 (s, 1H), 4.87 (br. s., 1H), 4.29 (d, J=7.3 Hz, 1H), 4.25-4.16 (m, 2H), 3.07 (t, J=11.7 Hz, 1H), 2.87-2.78 (m, 1H), 2.78 (s, 3H), 2.77-2.56 (m, 3H), 2.15-2.07 (m, 2H), 1.89 (s, 2H), 1.85 (s, 1H), 1.77-1.64 (m, 3H), 1.62-1.44 (m, 1H), 1.24 (s, 5H), 1.23 (s, 4H). LCMS (M+H)=633.5.

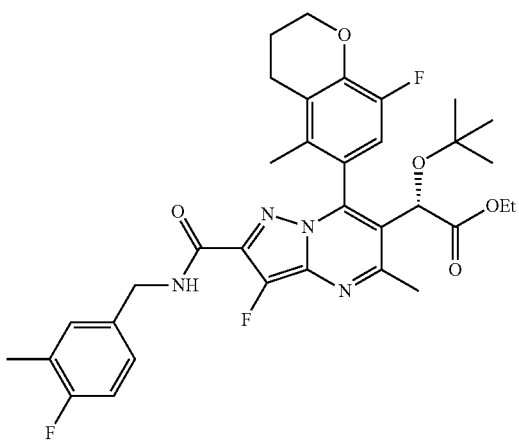 [SMILES: CCOC(=O)[C@@H](OC(C)(C)C)c1c(C)nc2c(F)c(C(=O)NCc3ccc(F)c(C)c3)nn2c1-c1cc(F)c2c(c1C)CCCO2]

(2S)-Ethyl 2-(tert-butoxy)-2-(3-fluoro-2-((4-fluoro-3-methylbenzyl)carbamoyl)-7-(8-fluoro-5-methylchroman-6-yl)-5-methylpyrazolo[1,5-a]pyrimidin-6-yl)acetate To a slurry of (2S)-ethyl 2-(tert-butoxy)-2-(2-((4-fluoro-3-methylbenzyl)carbamoyl)-7-(8-fluoro-5-methylchroman-6-yl)-5-methylpyrazolo[1,5-a]pyrimidin-6-yl)acetate (82 mg, 0.132 mmol, 1 equiv) in acetonitrile (2.6 mL) was added Selectfluor (56 mg, 0.159 mmol, 1.2 equiv). After stirring 18 h, reaction is an orange slurry. LCMS indicated ~50% conversion. The reaction was diluted with DCM and washed with saturated aqueous bicarbonate. The DCM layer was dried (Na$_2$SO$_4$) and concentrated in vacuo. The crude product was purified by flash silica gel chromatography (0-10% EtOAc in hexane) to provide desired product as a yellow solid (22 mg, 26% yield). $^1$H NMR (500 MHz, CDCl$_3$) δ 7.20-7.16 (m, 1H), 7.15-7.10 (m, 1H), 7.04-6.99 (m, 1H), 6.99-6.94 (m, 1H), 6.87-6.81 (m, 1H), 4.95 (s, 1H), 4.57 (d, J=5.8 Hz, 2H), 4.35 (br. s., 2H), 4.19-4.11 (m, 2H), 2.80 (s, 3H), 2.78-2.73 (m, 2H), 2.27 (s, 3H), 2.18 (br. s., 2H), 1.81 (s, 3H), 1.29 (t, J=6.9 Hz, 3H), 1.17 (s, 9H); $^{19}$F NMR (471 MHz, CDCl$_3$) d−119.41 (s, 1F), −139.50 (s, 1F), −175.35 (s, 1F); LCMS (ESI, M+1): 639.5.

Example 139

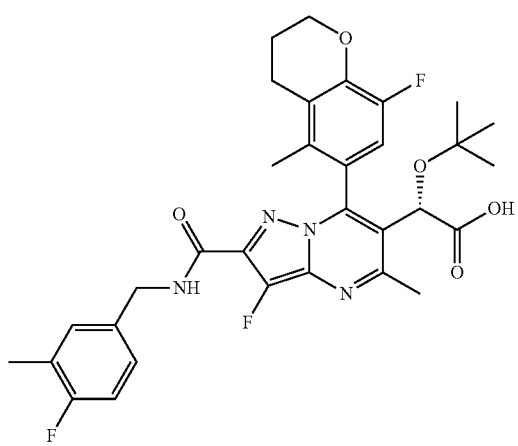 [SMILES: Cc1cc(CNC(=O)c2nn3c(-c4cc(F)c5c(c4C)CCCO5)c([C@H](OC(C)(C)C)C(=O)O)c(C)nc3c2F)ccc1F]

(2S)-2-(tert-Butoxy)-2-(3-fluoro-2-((4-fluoro-3-methylbenzyl)carbamoyl)-7-(8-fluoro-5-methylchroman-6-yl)-5-methylpyrazolo[1,5-a]pyrimidin-6-yl) acetic acid To a solution of (2S)-ethyl 2-(tert-butoxy)-2-(3-fluoro-2-((4-fluoro-3-methylbenzyl)carbamoyl)-7-(8-fluoro-5-methylchroman-6-yl)-5-methylpyrazolo[1,5-a]pyrimidin-6-yl) acetate (22 mg, 0.034 mol, 1 equiv) in ethanol (0.46 mL) and water (0.23 mL) was added lithium hydroxide monohydrate (7.2 mg, 0.172 mmol, 5 equiv). The reaction was heated in an oil bath at 60° C. for 2 h. After cooling to ambient temperature, the reaction was filtered and loaded directly onto reverse phase HPLC (acetonitrile/TFA eluent). Desired compound was isolated as an off white solid (2.0 mg, 9% yield). $^1$H NMR (400 MHz, CDCl$_3$) δ 7.19-7.14 (m, 1H), 7.14-7.09 (m, 1H), 7.08-7.03 (m, 1H), 6.99-6.92 (m, J=9.3 Hz, 1H), 6.84 (d, J=10.5 Hz, 1H), 5.05 (s, 1H), 4.56 (d, J=6.0 Hz, 2H), 4.33 (t, J=4.8 Hz, 2H), 2.75 (s, 3H), 2.74-2.71 (m, 2H), 2.26 (d, J=1.8 Hz, 3H), 2.20-2.12 (m, 2H), 1.87 (s, 3H), 1.20 (s, 9H); $^{19}$F NMR (376 MHz, CDCl$_3$) δ −119.18 (s, 1F), −139.26 (s, 1F), −174.64 (s, 1F); LCMS (ESI, M+1): 611.4.

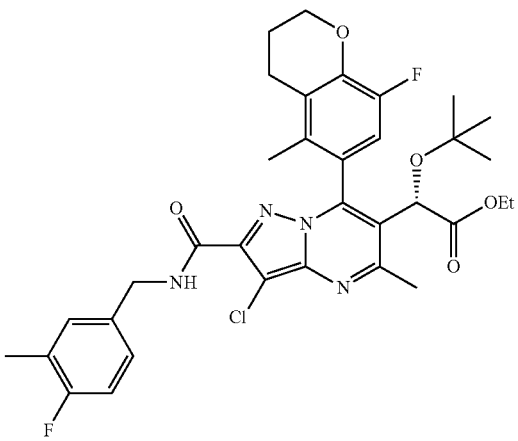 [SMILES: CCOC(=O)[C@@H](OC(C)(C)C)c1c(C)nc2c(Cl)c(C(=O)NCc3ccc(F)c(C)c3)nn2c1-c1cc(F)c2c(c1C)CCCO2]

(2S)-Ethyl 2-(tert-butoxy)-2-(3-chloro-2-((4-fluoro-3-methylbenzyl)carbamoyl)-7-(8-fluoro-5-methylchroman-6-yl)-5-methylpyrazolo[1,5-a]pyrimidin-6-yl)acetate To a solution of (2S)-ethyl 2-(tert-butoxy)-2-(2-((4-fluoro-3-methylbenzyl)carbamoyl)-7-(8-fluoro-5-methylchroman-6-yl)-5-methylpyrazolo[1,5-a]pyrimidin-6-yl)acetate (40 mg, 0.064 mmol, 1 equiv) in acetic acid (0.64 mL) was added NCS (10 mg, 0.077 mmol, 1.2 equiv). After stirring 18 h, reaction is pale yellow solution. LCMS indicated complete conversion. The reaction was diluted with DCM and washed with saturated aqueous bicarbonate. The DCM layer was dried (Na$_2$SO$_4$) and concentrated in vacuo. The crude product was purified by flash silica gel chromatography (0-10% EtOAc in hexane) to provide desired product as a viscous yellow oil (22 mg, 52% yield). $^1$H NMR (500 MHz, CDCl$_3$) δ 7.16 (s, 1H), 7.12 (d, J=5.7 Hz, 2H), 6.97 (d, J=9.1 Hz, 1H), 6.83 (d, J=10.6 Hz, 1H), 4.97 (s, 1H), 4.62-4.50 (m, 2H), 4.35 (t, J=5.3 Hz, 2H), 4.19-4.11 (m, 2H), 2.84 (s, 3H), 2.75 (s, 2H), 2.27 (d, J=1.7 Hz, 3H), 2.23-2.13 (m, 2H), 1.80 (s, 3H), 1.29 (t, J=7.1 Hz, 3H), 1.17 (s, 9H); $^{19}$F NMR (471 MHz, CDCl₃) δ −119.48 (s, 1F), −139.47 (s, 1F); LCMS (ESI, M+1): 655.5.

Example 140

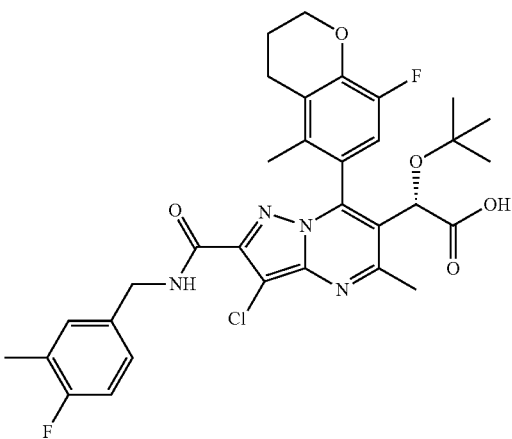 [SMILES: Cc1cc(CNC(=O)c2nn3c(-c4cc(F)c5c(c4C)CCCO5)c([C@H](OC(C)(C)C)C(=O)O)c(C)nc3c2Cl)ccc1F]

(2S)-2-(tert-Butoxy)-2-(3-chloro-2-((4-fluoro-3-methylbenzyl)carbamoyl)-7-(8-fluoro-5-methylchroman-6-yl)-5-methylpyrazolo[1,5-a]pyrimidin-6-yl) acetic acid To a solution of (2S)-ethyl 2-(tert-butoxy)-2-(3-chloro-2-((4-fluoro-3-methylbenzyl)carbamoyl)-7-(8-fluoro-5-methylchroman-6-yl)-5-methylpyrazolo[1,5-a]pyrimidin-6-yl) acetate (22 mg, 0.034 mol, 1 equiv) in ethanol (0.45 mL) and water (0.22 mL) was added lithium hydroxide monohydrate (7 mg, 0.168 mmol, 5 equiv). The reaction was heated in an oil bath at 60° C. for 16 h. After cooling to ambient temperature, the reaction was filtered and loaded directly onto reverse phase HPLC (acetonitrile/TFA eluent). The desired compound was isolated as an off white solid (2.4 mg, 11% yield). ¹H NMR (500 MHz, CDCl₃) δ 7.19-7.15 (m, 2H), 7.14-7.10 (m, 1H), 7.00-6.94 (m, 1H), 6.86 (d, J=10.6 Hz, 1H), 5.08 (s, 1H), 4.57 (d, J=6.3 Hz, 2H), 4.36-4.32 (m, 2H), 2.81 (s, 3H), 2.77-2.72 (m, 2H), 2.27 (d, J=1.7 Hz, 3H), 2.20-2.14 (m, 2H), 1.88 (s, 3H), 1.22 (s, 9H); $^{19}$F NMR (471 MHz, CDCl₃) δ 119.29 (s, 1F), −139.22 (s, 1F); LCMS (ESI, M+1): 627.5.

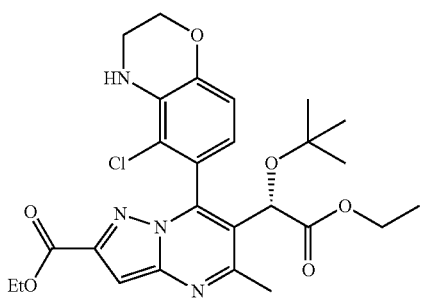 [SMILES: CCOC(=O)c1cc2nc(C)c([C@H](OC(C)(C)C)C(=O)OCC)c(-c3ccc4c(c3Cl)NCCO4)n2n1]

Ethyl 6-((S)-1-(tert-butoxy)-2-ethoxy-2-oxoethyl)-7-(5-chloro-3,4-dihydro-2H-benzo[b][1,4]oxazin-6-yl)-5-methylpyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (400 mg, 0.817 mmol), 5-chloro-6-(4,4,5,5-tetramethyl-1,3,2-dioxaborolan-2-yl)-3,4-dihydro-2H-benzo[b][1,4]oxazine (prepared according to the procedure described in WO 2009/062285; 290 mg, 0.981 mmol) and 2N Na₂CO₃ (0.817 mL, 1.635 mmol) in DMF (8 mL) was degassed for 15 min. Tetrakis(triphenylphosphine)palladium(0) (66.1 mg, 0.057 mmol) was added and the degassing was continued for another 5 min. The mixture was then heated at 90° C. for 16 h. At this point LCMS indicated completion of reaction and presence of desired product. After cooling to room temperature, water was added (25 mL) and the mixture was extracted with ethyl acetate (2×100 mL), washed with brine (100 mL), dried (Na2SO4), filtered and concentrated. The crude was purified by biotage (5-70% EtOAc/hexane) to afford ethyl 6-((S)-1-(tert-butoxy)-2-ethoxy-2-oxoethyl)-7-(5-chloro-3,4-dihydro-2H-benzo[b][1,4]oxazin-6-yl)-5-methylpyrazolo[1,5-a]pyrimidine-2-carboxylate (315 mg, 0.593 mmol, 72.6% yield) as a mixture of two atrope isomers which are not separable (approx 10-15% of minor atrope isomer present by LCMS and NMR). Mixture was used as is in the next step without further purification.

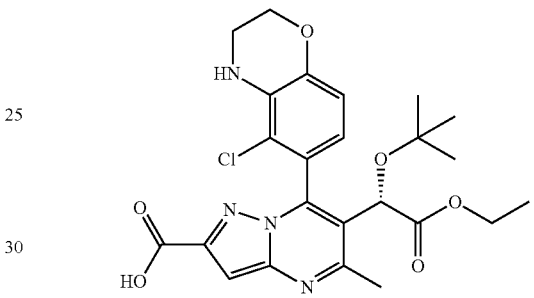

6-(((S)-1-(tert-Butoxy)-2-ethoxy-2-oxoethyl)-7-(5-chloro-3,4-dihydro-2H-benzo[b][1,4]oxazin-6-yl)-5-methylpyrazolo[1,5-a]pyrimidine-2-carboxylic acid To a solution of ethyl 6-((S)-1-(tert-butoxy)-2-ethoxy-2-oxoethyl)-7-(5-chloro-3,4-dihydro-2H-benzo[b][1,4]oxazin-6-yl)-5-methylpyrazolo[1,5-a]pyrimidine-2-carboxylate (315 mg, 0.593 mmol) in EtOH (6 mL) was added 1N NaOH (0.712 mL, 0.712 mmol) and the resulting mixture was stirred at room temp for 4 h. A this point LCMS indicated completion of reaction. Then, the reaction mixture was concentrated and the residue diluted with water (3 mL), acidified with 1N HCl, extracted with ethyl acetate (25 mL), washed with brine (10 mL), dried (Na2SO4), filtered and concentrated to afford 6-((S)-1-(tert-butoxy)-2-ethoxy-2-oxoethyl)-7-(5-chloro-3,4-dihydro-2H-benzo[b][1,4]oxazin-6-yl)-5-methylpyrazolo[1,5-a]pyrimidine-2-carboxylic acid (230 mg, 0.457 mmol, 77% yield) as off-white solid (approx 2:1 mixture of mono and di-acid) which was used as is in the next step without further purification. LCMS (M+H)=503.3.

Example 141

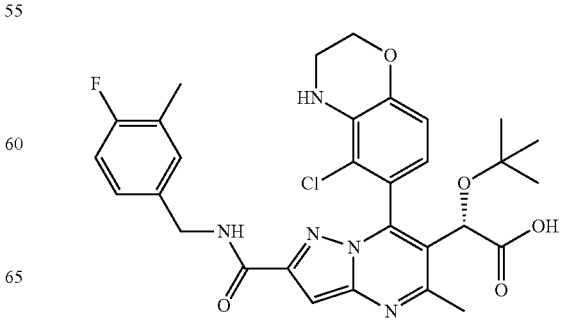

(2S)-2-(tert-Butoxy)-2-(7-(5-chloro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid To a mixture of 6-((S)-1-(tert-butoxy)-2-ethoxy-2-oxoethyl)-7-(5-chloro-3,4-dihydro-2H-benzo[b][1,4]oxazin-6-yl)-5-methylpyrazolo[1,5-a]pyrimidine-2-carboxylic acid (50 mg, 0.099 mmol) and (4-fluoro-3-methylphenyl)methanamine (27.7 mg, 0.199 mmol) in DMF (2 mL) was added DIEA (0.087 mL, 0.497 mmol), HATU (76 mg, 0.199 mmol) and DMAP (2.429 mg, 0.020 mmol) and the resulting mixture was stirred at room temperature for 16 h. At this point LCMS indicated completion of reaction. Mixture was then filtered and purified by prep-HPLC to afford desired ester, which was treated with 1N NaOH (0.298 mL, 0.298 mmol) in MeOH (2.000 mL) at 60° C. for 5 h. Mixture was then cooled and purified by prep-HPLC to afford (2S)-2-(tert-butoxy)-2-(7-(5-chloro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid (18.6 mg, 0.030 mmol, 29.8% yield). $^1$H NMR (500 MHz, DMSO-$d_6$) δ 8.67 (t, J=6.1 Hz, 1H), 7.20 (d, J=7.6 Hz, 1H), 7.16-7.11 (m, 1H), 7.10-7.03 (m, 1H), 7.02 (s, 1H), 6.84 (d, J=8.2 Hz, 1H), 6.60 (d, J=8.2 Hz, 1H), 5.95 (br. s., 1H), 4.83 (br. s., 1H), 4.38 (t, J=6.7 Hz, 2H), 4.23 (br. s., 2H), 3.42 (br. s., 2H), 2.73 (s, 3H), 2.20 (s, 3H), 1.07 (s, 9H). LCMS (M+H)=596.4.

Examples 142 and 143 were prepared similar to the procedure for example 141.

Example 142

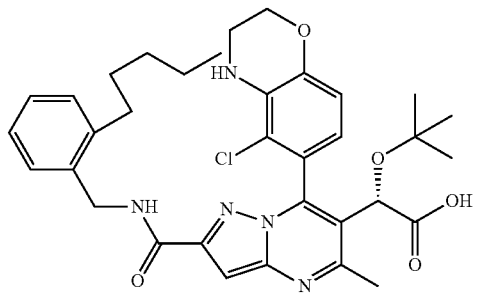 [SMILES: CCCCCc1ccccc1CNC(=O)c1cc2nc(C)c([C@H](OC(C)(C)C)C(=O)O)c(-c3ccc4c(c3Cl)NCCO4)n2n1]

(2S)-2-(tert-Butoxy)-2-(7-(5-chloro-3,4-dihydro-2H-benzo[b][1,4]oxazin-6-yl)-5-methyl-2-((2-pentylbenzyl)carbamoyl)pyrazolo[1,5-a]pyrimidin-6-yl)acetic acid $^1$H NMR (400 MHz, CDCl$_3$) δ 7.31-7.29 (m, 1H), 7.25-7.20 (m, 3H), 7.20-7.14 (m, 2H), 6.86 (d, J=8.3 Hz, 1H), 6.55 (d, J=8.3 Hz, 1H), 5.19 (s, 1H), 4.67 (d, J=6.0 Hz, 2H), 4.38-4.32 (m, 2H), 3.58 (d, J=3.8 Hz, 2H), 2.84 (s, 3H), 2.68-2.61 (m, 2H), 1.38-1.26 (m, 4H), 1.19 (s, 9H), 0.87 (t, J=7.1 Hz, 3H). LCMS (M+H)=634.5.

Example 143

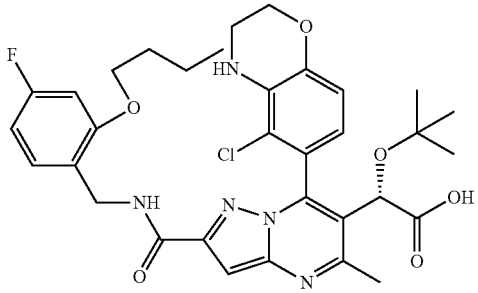 [SMILES: CCCCOc1cc(F)ccc1CNC(=O)c1cc2nc(C)c([C@H](OC(C)(C)C)C(=O)O)c(-c3ccc4c(c3Cl)NCCO4)n2n1]

(2S)-2-(tert-Butoxy)-2-(2-((2-butoxy-4-fluorobenzyl)carbamoyl)-7-(5-chloro-3,4-dihydro-2H-benzo[b][1,4]oxazin-6-yl)-5-methylpyrazolo[1,5-a]pyrimidin-6-yl)acetic acid $^1$H NMR (500 MHz, CDCl$_3$) δ 7.38-7.33 (m, 1H), 7.25 (dd, J=8.0, 6.9 Hz, 1H), 7.19 (s, 1H), 6.87 (d, J=8.4 Hz, 1H), 6.63-6.54 (m, 3H), 5.19 (s, 1H), 4.61-4.52 (m, 2H), 4.40-4.33 (m, 2H), 3.93 (t, J=6.4 Hz, 2H), 3.62-3.58 (m, 2H), 2.83 (s, 3H), 1.74-1.67 (m, 2H), 1.46 (sxt, J=7.4 Hz, 2H), 1.19 (s, 9H), 0.96 (t, J=7.4 Hz, 3H). LCMS (M+H)=654.5.

Example 144

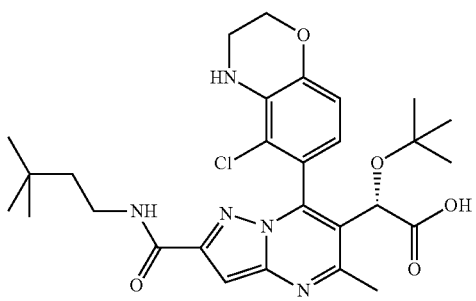 [SMILES: Cc1nc2cc(C(=O)NCCC(C)(C)C)nn2c(-c2ccc3c(c2Cl)NCCO3)c1[C@H](OC(C)(C)C)C(=O)O]

(2S)-2-(tert-Butoxy)-2-(7-(5-chloro-3,4-dihydro-2H-benzo[b][1,4]oxazin-6-yl)-2-((3,3-dimethylbutyl)carbamoyl)-5-methylpyrazolo[1,5-a]pyrimidin-6-yl)acetic acid To a mixture of 6-((S)-1-(tert-butoxy)-2-ethoxy-2-oxoethyl)-7-(5-chloro-3,4-dihydro-2H-benzo[b][1,4]oxazin-6-yl)-5-methylpyrazolo[1,5-a]pyrimidine-2-carboxylic acid (50 mg, 0.099 mmol) and 3,3-dimethylbutan-1-amine (20.12 mg, 0.199 mmol) in DMF (2 mL) was added DIEA (0.087 mL, 0.497 mmol), HATU (76 mg, 0.199 mmol) and DMAP (2.429 mg, 0.020 mmol) and the resulting mixture was stirred at room temp for 16 h. At this point LCMS indicated completion of reaction. Mixture was then filtered and purified by prep-HPLC to afford desired ester, which was treated with 1N NaOH (0.298 mL, 0.298 mmol) in MeOH (2.000 mL) at 60° C. for 5 h. Mixture was then cooled and purified by prep-HPLC to afford (2S)-2-(tert-butoxy)-2-(7-(5-chloro-3,4-dihydro-2H-benzo[b][1,4]oxazin-6-yl)-2-((3,3-dimethylbutyl)carbamoyl)-5-methylpyrazolo[1,5-a]pyrimidin-6-yl)acetic acid (17.2 mg, 0.029 mmol, 29.5% yield). $^1$H NMR (500 MHz, DMSO-$d_6$) δ 8.03 (t, J=6.0 Hz, 1H), 6.94 (s, 1H), 6.84 (d, J=8.2 Hz, 1H), 6.59 (d, J=8.2 Hz, 1H), 5.95 (br. s., 1H), 4.82 (br. s., 1H), 4.24 (d, J=4.0 Hz, 2H), 3.43 (d, J=3.1 Hz, 2H), 3.28-3.18 (m, 2H), 2.73 (s, 3H), 1.41 (t, J=8.2 Hz, 2H), 1.07 (s, 9H), 0.91 (s, 9H). LCMS (M+H)=558.4.

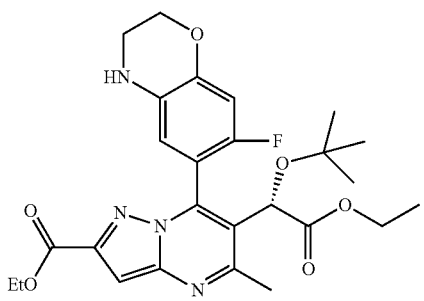 [SMILES: CCOC(=O)c1cc2nc(C)c([C@H](OC(C)(C)C)C(=O)OCC)c(-c3cc4c(cc3F)OCCN4)n2n1]

Ethyl 6-((S)-1-(tert-butoxy)-2-ethoxy-2-oxoethyl)-7-(7-fluoro-3,4-dihydro-2H-benzo[b][1,4]oxazin-6-yl)-5-methylpyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (300 mg, 0.613 mmol), 7-fluoro-6-(4,4,5,5-tetramethyl-1,3,2-dioxaborolan-2-yl)-3,4-dihydro-2H-benzo[b][1,4]oxazine (prepared according to the procedure described in WO 2009/062285; 205 mg, 0.736 mmol) and 2N Na$_2$CO$_3$ (0.613 mL, 1.226 mmol) in DMF (6 mL) was degassed for 15 min. Tetrakis(triphenylphosphine)palladium(0) (49.6 mg, 0.043 mmol) was added and the degassing was continued for another 5 min. The mixture was then heated at 100° C. for 16 h. At this point LCMS indicated completion of reaction and presence of desired product. After cooling to room temperature, water was added (50 mL) and the mixture was extracted with ethyl acetate (2×100 mL), washed with brine (100 mL), dried (Na$_2$SO$_4$), filtered and concentrated. The crude was then purified by prep-HPLC to afford ethyl 6-((S)-1-(tert-butoxy)-2-ethoxy-2-oxoethyl)-7-(7-fluoro-3,4-dihydro-2H-benzo[b][1,4]oxazin-6-yl)-5-methylpyrazolo[1,5-a]pyrimidine-2-carboxylate (approx 10-15% of minor atrope isomer present by LCMS and NMR). $^1$H NMR (500 MHz, CDCl$_3$) δ 7.11 (s, 1H), 6.74 (dd, J=8.3, 1.8 Hz, 2H), 5.17 (s, 1H), 4.48-4.33 (m, 4H), 4.24 (t, J=7.0 Hz, 2H), 3.83 (br. s., 1H), 3.51-3.41 (m, 2H), 2.70 (s, 3H), 1.43-1.39 (m, 3H), 1.31-1.26 (m, 3H), 1.05 (s, 9H). LCMS (M+H)=515.4.

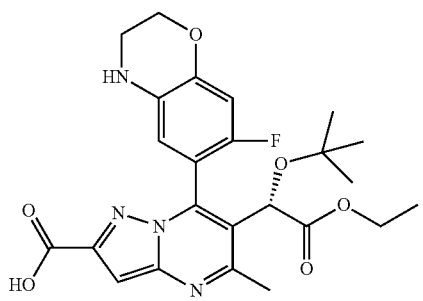 [SMILES: CCOC(=O)[C@@H](OC(C)(C)C)c1c(C)nc2cc(C(=O)O)nn2c1-c1cc2c(cc1F)OCCN2]

6-((S)-1-(tert-Butoxy)-2-ethoxy-2-oxoethyl)-7-(7-fluoro-3,4-dihydro-2H-benzo[b][1,4]oxazin-6-yl)-5-methylpyrazolo[1,5-a]pyrimidine-2-carboxylic acid To a solution of ethyl 6-((S)-1-(tert-butoxy)-2-ethoxy-2-oxoethyl)-7-(7-fluoro-3,4-dihydro-2H-benzo[b][1,4]oxazin-6-yl)-5-methylpyrazolo[1,5-a]pyrimidine-2-carboxylate (130 mg, 0.253 mmol) in EtOH (4 mL) was added 1N NaOH (0.303 mL, 0.303 mmol) and the resulting mixture was stirred at room temp for 4 h. At this point LCMS indicated completion of reaction. The reaction mixture concentrated and the residue diluted with water (3 mL), acidified with 1N HCl, extracted with ethyl acetate (25 mL), washed with brine (10 mL), dried (Na2SO4), filtered and concentrated to afford 6-((S)-1-(tert-butoxy)-2-ethoxy-2-oxoethyl)-7-(7-fluoro-3,4-dihydro-2H-benzo[b][1,4]oxazin-6-yl)-5-methylpyrazolo[1,5-a]pyrimidine-2-carboxylic acid (110 mg, 0.226 mmol, 89% yield) as off-white solid (mixture of mono and diacid and also atrope isomers) which was used as is in the next step without further purification. LCMS (M+H)=487.3.

Example 145

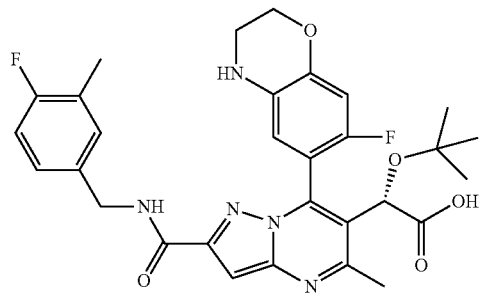 [SMILES: Cc1cc(CNC(=O)c2cc3nc(C)c([C@H](OC(C)(C)C)C(=O)O)c(-c4cc5c(cc4F)OCCN5)n3n2)ccc1F]

(2S)-2-(tert-Butoxy)-2-(7-(7-fluoro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid To a mixture of 6-((S)-1-(tert-butoxy)-2-ethoxy-2-oxoethyl)-7-(7-fluoro-3,4-dihydro-2H-benzo[b][1,4]oxazin-6-yl)-5-methylpyrazolo[1,5-a]pyrimidine-2-carboxylic acid (50 mg, 0.103 mmol) and (4-fluoro-3-methylphenyl)methanamine (28.6 mg, 0.206 mmol) in DMF (2 mL) was added DIEA (0.090 mL, 0.514 mmol), HATU (78 mg, 0.206 mmol) and DMAP (2.51 mg, 0.021 mmol) and the resulting mixture was stirred at room temp for 16 h. At this point LCMS indicated completion of reaction. Mixture was then filtered and purified by prep-HPLC to afford desired ester, which was treated with 1N NaOH (0.308 mL, 0.308 mmol) in MeOH (2.000 mL) at 60° C. for 5 h. Mixture was then cooled and purified by prep HPLC to afford (2S)-2-(tert-butoxy)-2-(7-(7-fluoro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid (35.3 mg, 0.058 mmol, 56.3% yield). $^1$H NMR (500 MHz, DMSO-d$_6$) δ 8.65 (t, J=6.3 Hz, 1H), 7.20 (d, J=7.6 Hz, 1H), 7.17-7.12 (m, 1H), 7.10-7.04 (m, 1H), 7.02-6.95 (m, 2H), 6.79 (d, J=10.7 Hz, 1H), 5.97 (br. s., 1H), 4.92 (s, 1H), 4.39 (d, J=6.7 Hz, 2H), 4.24 (t, J=4.3 Hz, 2H), 3.29 (d, J=4.3 Hz, 2H), 2.60 (s, 3H), 2.20 (s, 3H), 0.93 (s, 9H). LCMS (M+H)=580.4.

Example 146

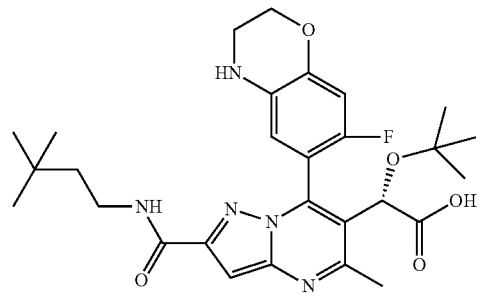 [SMILES: Cc1nc2cc(C(=O)NCCC(C)(C)C)nn2c(-c2cc3c(cc2F)OCCN3)c1[C@H](OC(C)(C)C)C(=O)O]

(2S)-2-(tert-Butoxy)-2-(2-((3,3-dimethylbutyl)carbamoyl)-7-(7-fluoro-3,4-dihydro-2H-benzo[b][1,4]oxazin-6-yl)-5-methylpyrazolo[1,5-a]pyrimidin-6-yl)acetic acid To a mixture of 6-((S)-1-(tert-butoxy)-2-ethoxy-2-oxoethyl)-7-(7-fluoro-3,4-dihydro-2H-benzo[b][1,4]oxazin-6-yl)-5-methylpyrazolo[1,5-a]pyrimidine-2-carboxylic acid (50 mg, 0.103 mmol) and 3,3-dimethylbutan-1-amine (20.80 mg, 0.206 mmol) in DMF (2 mL) was added DIEA (0.090 mL, 0.514 mmol), HATU (78 mg, 0.206 mmol) and DMAP (2.51 mg, 0.021 mmol) and the resulting mixture was stirred at room temp for 16 h. At this point LCMS indicates completion of reaction. Mixture was then filtered and purified by prep-HPLC to afford desired ester, which was treated with 1N NaOH (0.308 mL, 0.308 mmol) in MeOH (2.000 mL) at 60° C. for 5 h. Mixture was then cooled and purified by prep HPLC to afford (2S)-2-(tert-butoxy)-2-(2-((3,3-dimethylbutyl)carbamoyl)-7-(7-fluoro-3,4-dihydro-2H-benzo[b][1,4]oxazin-6-yl)-5-methylpyrazolo[1,5-a]pyrimidin-6-yl)acetic acid (10.5 mg, 0.018 mmol, 17.92% yield). $^1$H NMR (500 MHz, DMSO-$d_6$) δ 8.03 (t, J=5.8 Hz, 1H), 6.96 (d, J=6.1 Hz, 1H), 6.93 (s, 1H), 6.80 (d, J=10.7 Hz, 1H), 5.99 (br. s., 1H), 4.96 (s, 1H), 4.25 (t, J=4.1 Hz, 2H), 3.30-3.22 (m, 4H), 2.60 (s, 3H), 1.46-1.40 (m, 2H), 0.94 (s, 9H), 0.91 (s, 9H). LCMS (M+H)=542.4.

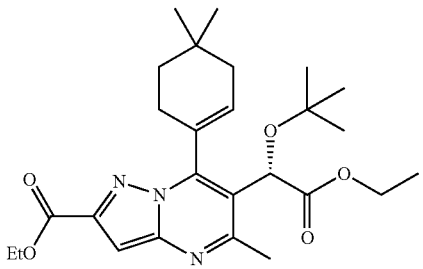

(S)-Ethyl 6-(1-(tert-butoxy)-2-ethoxy-2-oxoethyl)-7-(4,4-dimethylcyclohex-1-en-1-yl)-5-methylpyrazolo[1,5-]pyrimidine-2-carboxylate A mixture of Reactant 1 (300 mg, 0.613 mmol), (4,4-dimethylcyclohex-1-en-1-yl)boronic acid (113 mg, 0.736 mmol) and 2N Na$_2$CO$_3$ (0.613 mL, 1.226 mmol) in DMF (6 mL) was degassed for 15 min. Tetrakis(triphenylphosphine)palladium(0) (49.6 mg, 0.043 mmol) was then added and the degassing was continued for another 5 min. The mixture was then heated at 100° C. for 2 h. At this point LCMS indicates completion of reaction and presence of desired product. After cooling to room temperature, water was added (10 mL) and the mixture was extracted with ether (2×50 mL), washed with brine (25 mL), dried (Na$_2$SO$_4$), filtered and concentrated. The crude was then purified by biotage (5-30% EtOAc/hexane) to afford (S)-ethyl 6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylate (185 mg, 0.392 mmol, 64.0% yield) as off-white solid. $^1$H NMR (500 MHz, CDCl$_3$) δ 7.05 (s, 1H), 6.25 (br. s., 0.7H), 5.93 (s, 0.3H), 5.55 (s, 0.7H), 5.48 (s, 0.3H), 4.50-4.36 (m, 2H), 4.27-4.17 (m, 2H), 3.36-3.23 (m, 1H), 2.77 (s, 1H), 2.69 (s, 2H), 2.30-2.16 (m, 2H), 2.09-1.92 (m, 1H), 1.80-1.69 (m, 1H), 1.60 (s, 6H), 1.59-1.50 (m, 1H), 1.44 (t, J=7.2 Hz, 3H), 1.26-1.20 (m, 12H). LCMS (M+H)=472.8.

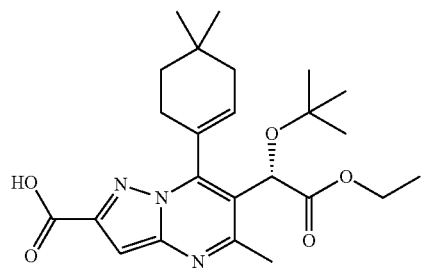 [SMILES: CCOC(=O)[C@@H](OC(C)(C)C)c1c(C)nc2cc(C(=O)O)nn2c1C1=CCC(C)(C)CC1]

(S)-6-(1-(tert-Butoxy)-2-ethoxy-2-oxoethyl)-7-(4,4-dimethylcyclohex-1-en-1-yl)-5-methylpyrazolo[1,5-a]pyrimidine-2-carboxylic acid To a solution of (S)-ethyl 6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylate (185 mg, 0.392 mmol) in EtOH (4 mL) was added 1N NaOH (0.392 mL, 0.392 mmol) and the resulting mixture was stirred at room temp for 4 h. A this point LCMS indicated completion of reaction. Solvents were then removed under reduced pressure and the mixture was diluted with water (3 mL), acidified with 1N HCl, extracted with ethyl acetate (25 mL), washed with brine (10 mL), dried (Na$_2$SO$_4$), filtered and concentrated to afford (S)-6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylic acid (150 mg, 0.338 mmol, 86% yield) as light yellow solid. $^1$H NMR (500 MHz, CDCl$_3$) δ 7.15 (s, 1H), 6.26 (br. s., 0.6H), 5.93 (br. s., 0.4H), 5.53 (s, 0.6H), 5.46 (s, 0.4H), 4.29-4.19 (m, 2H), 2.79 (s, 1H), 2.72 (s, 2H), 2.19-2.14 (m, 2H), 1.77-1.54 (m, 4H), 1.29-1.16 (m, 18H). LCMS (M+H)=444.4.

Example 147

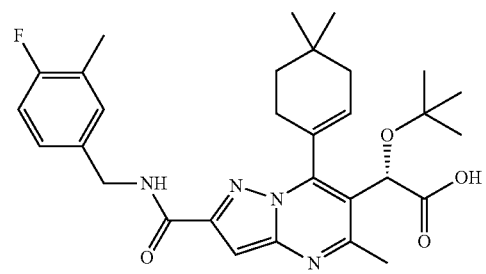 [SMILES: Cc1cc(CNC(=O)c2cc3nc(C)c([C@H](OC(C)(C)C)C(=O)O)c(C4=CCC(C)(C)CC4)n3n2)ccc1F]

(S)-2-(tert-butoxy)-2-(7-(4,4-dimethylcyclohex-1-en-1-yl)-2-((4-fluoro-3-methylbenzyl)carbamoyl)-5-methylpyrazolo[1,5-a]pyrimidin-6-yl)acetic acid To a mixture of (S)-6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylic acid (30 mg, 0.068 mmol) and (4-fluoro-3-methylphenyl)methanamine (18.83 mg, 0.135 mmol) in DMF (1.5 mL) was added DIEA (0.059 mL, 0.338 mmol), HATU (51.4 mg, 0.135 mmol) and DMAP (1.653 mg, 0.014 mmol) and the resulting mixture was stirred at room temp for 16 h. At this point LCMS indicated completion of reaction. Water was then added and the mixture was extracted with ether (25 mL), washed with brine (15 mL), dried (Na$_2$SO$_4$), filtered and concentrated. Crude was then treated with 1N NaOH (0.203 mL, 0.203 mmol) in MeOH (1.500 mL) at 60° C. for 5 h. Mixture was then cooled and purified by prep-HPLC to afford (S)-2-(tert-butoxy)-2-(7-(4,4-dimethylcyclohex-1-en-1-yl)-2-((4-fluoro-3-methylbenzyl)carbamoyl)-5-methylpyrazolo[1,5-a]pyrimidin-6-yl)acetic acid (16.5 mg, 0.029 mmol, 43.2% yield). $^1$H NMR (500 MHz, DMSO-d$_6$) δ 8.58 (t, J=6.0 Hz, 1H), 7.25 (d, J=7.6 Hz, 1H), 7.19 (dd, J=8.2, 5.2 Hz, 1H), 7.12-7.06 (m, 1H), 6.92 (s, 1H), 6.33 (br. s., 0.7H), 5.85 (br. s.; 0.3H), 5.31 (br. s., 0.7H), 5.23 (br. s., 0.3H), 4.54-4.39 (m, 2H), 2.67 (br. s., 1H), 2.59 (s, 2H), 2.23 (d, J=1.5 Hz, 3H), 2.14-2.10 (m, 4H), 1.70-1.59 (m, 2H), 1.18 (br. s., 3H), 1.14 (s, 7H), 1.08 (br. s., 2H), 1.07 (br. s., 4H). LCMS (M+H)=537.5.

Example 148

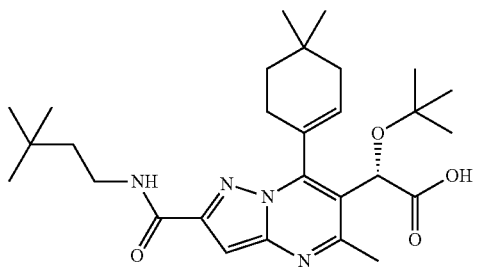 [SMILES: Cc1nc2cc(C(=O)NCCC(C)(C)C)nn2c(C2=CCC(C)(C)CC2)c1[C@H](OC(C)(C)C)C(=O)O]

(S)-2-(tert-Butoxy)-2-(2-((3,3-dimethylbutyl)carbamoyl)-7-(4,4-dimethylcyclohex-1-en-1-yl)-5-methylpyrazolo[1,5-a]pyrimidin-6-yl)acetic acid To a mixture of (S)-6-(1-(tert-butoxy)-2-ethoxy-2-oxoethyl)-7-(4,4-dimethylcyclohex-1-en-1-yl)-5-methylpyrazolo[1,5-a]pyrimidine-2-carboxylic acid (30 mg, 0.068 mmol) and 3,3-dimethylbutan-1-amine (13.69 mg, 0.135 mmol) in DMF (1.5 mL) was added DIEA (0.059 mL, 0.338 mmol), HATU (51.4 mg, 0.135 mmol) and DMAP (1.653 mg, 0.014 mmol) and the resulting mixture was stirred at room temp for 16 h. At this point LCMS indicated completion of reaction. Water was then added and the mixture was extracted with ether (25 mL), washed with brine (15 mL), dried (Na$_2$SO$_4$), filtered and concentrated. Crude was then treated with 1N NaOH (0.203 mL, 0.203 mmol) in MeOH (1.500 mL) at 60° C. for 5 h. Mixture was then cooled and purified by prep-HPLC to afford (S)-2-(tert-butoxy)-2-(2-((3,3-dimethylbutyl)carbamoyl)-7-(4,4-dimethylcyclohex-1-en-1-yl)-5-methylpyrazolo[1,5-a]pyrimidin-6-yl)acetic acid (23.6 mg, 0.045 mmol, 66.5% yield). $^1$H NMR (500 MHz, DMSO-d$_6$) δ 7.96 (t, J=5.8 Hz, 1H), 6.88 (s, 1H), 6.26 (br. s., 0.6H), 5.85 (br. s., 0.4H), 5.38 (s, 0.6H), 5.28 (s, 0.4H), 3.37-3.28 (m, 4H), 2.66 (s, 1H), 2.59 (s, 2H), 2.19-1.97 (m, 2H), 1.68-1.50 (m, 2H), 1.47 (t, J=7.9 Hz, 2H), 1.19 (s, 3H), 1.15 (s, 6H), 1.12 (s, 3H), 1.07 (s, 3H), 0.94 (s, 9H). LCMS (M+H)=499.4.

(S,E)-Ethyl 6-(1-(tert-butoxy)-2-ethoxy-2-oxoethyl)-5-methyl-7-(4-methylpent-1-en-1-yl)pyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (300 mg, 0.613 mmol), (E)-(4-methylpent-1-en-1-yl)boronic acid (94 mg, 0.736 mmol) and 2N Na$_2$CO$_3$ (0.613 mL, 1.226 mmol) in DMF (6 mL) was degassed for 15 min. Tetrakis(triphenylphosphine)palladium(0) (49.6 mg, 0.043 mmol) was then added and the degassing was continued for another 5 min. The mixture was then heated at 100° C. for 2 h. At this point LCMS indicated completion of reaction and presence of desired product. After cooling to room temperature, water was added (10 mL) and the mixture was extracted with ether (2×50 mL), washed with brine (25 mL), dried (Na$_2$SO$_4$), filtered and concentrated. the crude was then purified by biotage (5-30% EtOAc/hexane) to afford (S,E)-ethyl 6-(1-(tert-butoxy)-2-ethoxy-2-oxoethyl)-5-methyl-7-(4-methylpent-1-en-1-yl)pyrazolo[1,5-a]pyrimidine-2-carboxylate (200 mg, 0.449 mmol, 73.2% yield) as off-white solid. $^1$H NMR (500 MHz, CDCl$_3$) δ 7.09 (s, 1H), 7.07 (s, 0.6H), 7.04 (s, 1H), 5.57 (s, 1H), 4.49 (q, J=7.1 Hz, 2H), 4.33-4.20 (m, 2H), 2.70 (s, 3H), 2.40 (td, J=7.0, 1.3 Hz, 2H), 1.90 (dt, J=13.4, 6.7 Hz, 1H), 1.46 (t, J=7.1 Hz, 3H), 1.29 (t, J=7.1 Hz, 3H), 1.17 (s, 9H), 1.06 (dd, J=6.6, 2.7 Hz, 6H). LCMS (M+H)= 446.4.

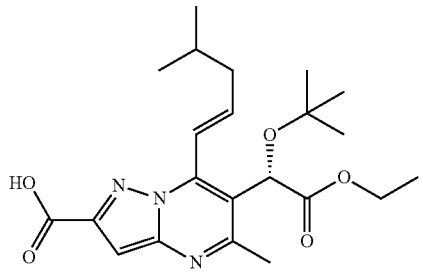

(S,E)-6-(1-(tert-Butoxy)-2-ethoxy-2-oxoethyl)-5-methyl-7-(4-methylpent-1-en-1-yl)pyrazolo[1,5-a]pyrimidine-2-carboxylic acid To a solution of (S,E)-ethyl 6-(1-(tert-butoxy)-2-ethoxy-2-oxoethyl)-5-methyl-7-(4-methylpent-1-en-1-yl)pyrazolo[1,5-a]pyrimidine-2-carboxylate (190 mg, 0.426 mmol) in EtOH (4 mL) was added 1N NaOH (0.426 mL, 0.426 mmol) and the resulting mixture was stirred at room temp for 4 h. At this point LCMS indicated completion of reaction. Solvents were then removed under reduced pressure and the mixture was diluted with water (3 mL), acidified with 1N HCl, extracted with ethyl acetate (25 mL), washed with brine (10 mL), dried (Na$_2$SO$_4$), filtered and concentrated to afford (S,E)-6-(1-(tert-butoxy)-2-ethoxy-2-oxoethyl)-5-methyl-7-(4-methylpent-1-en-1-yl)pyrazolo[1,5-a]pyrimidine-2-carboxylic acid (145 mg, 0.347 mmol, 81% yield) as light yellow solid. $^1$H NMR (500 MHz, CDCl$_3$) δ 7.20 (s, 1H), 7.01 (d, J=16.1 Hz, 1H), 6.90 (br. s., 1H), 5.57 (s, 1H), 4.48 (d, J=7.3 Hz, 1H), 4.30-4.22 (m, 2H), 2.72 (br. s., 3H), 2.00-1.85 (m, 1H), 1.32-1.25 (m, 3H), 1.18 (s, 9H), 1.10-0.97 (m, 6H). LCMS (M+H)=418.4.

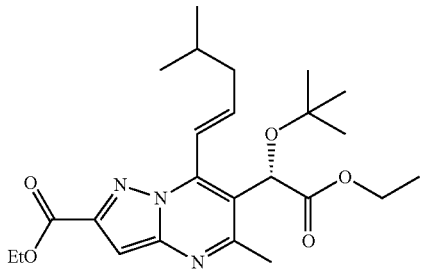 [SMILES: CCOC(=O)c1cc2nc(C)c([C@H](OC(C)(C)C)C(=O)OCC)c(/C=C/CC(C)C)n2n1]

Example 149

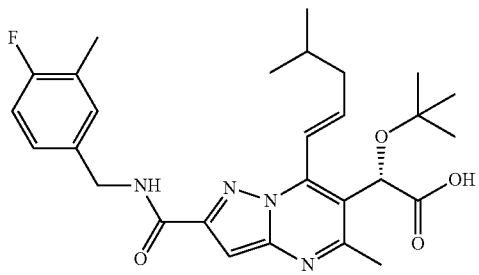 [SMILES: Cc1cc(CNC(=O)c2cc3nc(C)c([C@H](OC(C)(C)C)C(=O)O)c(/C=C/CC(C)C)n3n2)ccc1F]

(S,E)-2-(tert-Butoxy)-2-(2-((4-fluoro-3-methylbenzyl)carbamoyl)-5-methyl-7-(4-methylpent-1-en-1-yl)pyrazolo[1,5-a]pyrimidin-6-yl)acetic acid To a mixture of (S,E)-6-(1-(tert-butoxy)-2-ethoxy-2-oxoethyl)-5-methyl-7-(4-methylpent-1-en-1-yl)pyrazolo[1,5-a]pyrimidine-2-carboxylic acid (30 mg, 0.072 mmol) and (4-fluoro-3-methylphenyl)methanamine (20.00 mg, 0.144 mmol) in DMF (1.5 mL) was added DIEA (0.063 mL, 0.359 mmol), HATU (54.6 mg, 0.144 mmol) and DMAP (1.756 mg, 0.014 mmol) and the resulting mixture was stirred at room temp for 16 h. At this point LCMS indicated completion of reaction. Water was then added and the mixture was extracted with ether (25 mL), washed with brine (15 mL), dried ($Na_2SO_4$), filtered and concentrated. Crude was then treated with 1N NaOH (0.216 mL, 0.216 mmol) in MeOH (1.500 mL) at 60° C. for 5 h. Mixture was then cooled and purified by prep-HPLC to afford (S,E)-2-(tert-butoxy)-2-(2-((4-fluoro-3-methylbenzyl)carbamoyl)-5-methyl-7-(4-methylpent-1-en-1-yl)pyrazolo[1,5-a]pyrimidin-6-yl)acetic acid (12.2 mg, 0.023 mmol, 31.6% yield). $^1$H NMR (500 MHz, DMSO-$d_6$) δ 8.91 (t, J=6.4 Hz, 1H), 7.25 (d, J=7.3 Hz, 1.5H), 7.22-7.17 (m, 1.5H), 7.12-7.00 (m, 2H), 6.93 (s, 1H), 5.34 (br. s., 1H), 4.46 (t, J=5.6 Hz, 2H), 2.63 (s, 3H), 2.34 (t, J=6.3 Hz, 2H), 2.22 (s, 3H), 1.88-1.77 (m, 1H), 1.08 (s, 9H), 1.00 (dd, J=6.7, 2.4 Hz, 6H). LCMS (M+H)=511.33.

Example 150

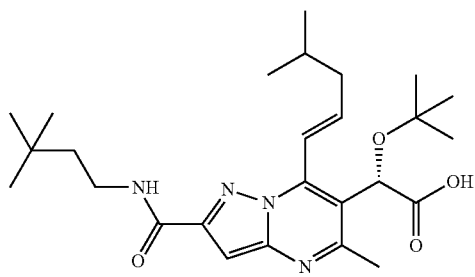 [SMILES: Cc1nc2cc(C(=O)NCCC(C)(C)C)nn2c(/C=C/CC(C)C)c1[C@H](OC(C)(C)C)C(=O)O]

(S,E)-2-(tert-Butoxy)-2-(2-((3,3-dimethylbutyl)carbamoyl)-5-methyl-7-(4-methylpent-1-en-1-yl)pyrazolo[1,5-a]pyrimidin-6-yl)acetic acid To a mixture of (S,E)-6-(1-(tert-butoxy)-2-ethoxy-2-oxoethyl)-5-methyl-7-(4-methylpent-1-en-1-yl)pyrazolo[1,5-a]pyrimidine-2-carboxylic acid (30 mg, 0.072 mmol) and 3,3-dimethylbutan-1-amine (14.54 mg, 0.144 mmol) in DMF (1.5 mL) was added DIEA (0.063 mL, 0.359 mmol), HATU (54.6 mg, 0.144 mmol) and DMAP (1.756 mg, 0.014 mmol) and the resulting mixture was stirred at room temp for 16 h. At this point LCMS indicated completion of reaction. Water was then added and the mixture was extracted with ether (25 mL), washed with brine (15 mL), dried (Na2SO4), filtered and concentrated. Crude was then treated with 1N NaOH (0.216 mL, 0.216 mmol) in MeOH (1.500 mL) at 60° C. for 5 h. Mixture was then cooled and purified by prep-HPLC to afford (S,E)-2-(tert-butoxy)-2-(2-((3,3-dimethylbutyl)carbamoyl)-5-methyl-7-(4-methylpent-1-en-1-yl)pyrazolo[1,5-a]pyrimidin-6-yl)acetic acid (3.7 mg, 7.44 μmol, 10.35% yield). $^1$H NMR (500 MHz, DMSO-$d_6$) δ 8.29 (t, J=6.0 Hz, 1H), 7.05 (d, J=14.0 Hz, 1H), 6.88 (s, 1H), 5.38 (s, 1H), 3.36-3.29 (m, 2H), 2.62 (s, 3H), 2.40-2.27 (m, 2H), 1.86 (dt, J=13.2, 6.7 Hz, 1H), 1.52-1.44 (m, 2H), 1.08 (s, 9H), 1.00 (d, J=3.7 Hz, 3H), 1.02 (d, J=3.7 Hz, 3H), 0.95 (s, 19H). LCMS (M+H)=473.4.

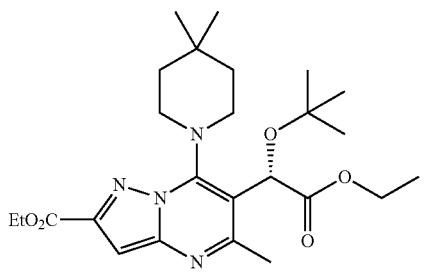 [SMILES: CCOC(=O)c1cc2nc(C)c([C@H](OC(C)(C)C)C(=O)OCC)c(N3CCC(C)(C)CC3)n2n1]

(S)-ethyl 6-(1-(tert-Butoxy)-2-ethoxy-2-oxoethyl)-7-(4,4-dimethylpiperidin-1-yl)-5-methylpyrazolo[1,5-a]pyrimidine-2-carboxylate To a solution of (S)-ethyl 6-(1-(tert-butoxy)-2-ethoxy-2-oxoethyl)-7-iodo-5-methylpyrazolo[1,5-a]pyrimidine-2-carboxylate (300 mg, 0.613 mmol) and 4,4-dimethylpiperidine, HCl (138 mg, 0.920 mmol) in NMP (3 mL) was added DIEA (0.321 mL, 1.839 mmol) and the mixture was heated at 50° C. for 72 h. At this point LCMS indicated completion of reaction. Mixture was cooled to room temperature and purified by prep-HPLC to afford (S)-ethyl 6-(1-(tert-butoxy)-2-ethoxy-2-oxoethyl)-7-(4,4-dimethylpiperidin-1-yl)-5-methylpyrazolo[1,5-a]pyrimidine-2-carboxylate (220 mg, 0.464 mmol, 76% yield) as off-white solid. $^1$H NMR (500 MHz, CDCl$_3$) δ 7.03 (s, 1H), 5.99 (s, 1H), 4.47 (q, J=7.1 Hz, 2H), 4.30-4.11 (m, 2H), 3.21-2.98 (m, 4H), 2.65 (s, 3H), 1.70-1.62 (m, 2H), 1.59-1.50 (m, 2H), 1.46 (t, J=7.1 Hz, 3H), 1.26 (s, 9H), 1.25-1.22 (m, 3H), 1.14 (s, 6H). LCMS (M+H)=475.2.

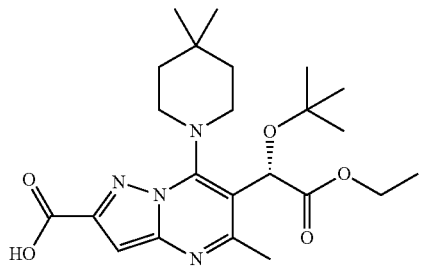 [SMILES: CCOC(=O)[C@@H](OC(C)(C)C)c1c(C)nc2cc(C(=O)O)nn2c1N1CCC(C)(C)CC1]

(S)-6-(1-(tert-Butoxy)-2-ethoxy-2-oxoethyl)-7-(4,4-dimethylpiperidin-1-yl)-5-methylpyrazolo[1,5-a]pyrimidine-2-carboxylic acid To a solution of (S)-ethyl 6-(1-(tert-butoxy)-2-ethoxy-2-oxoethyl)-7-(4,4-dimethylpiperidin-1-yl)-5-methylpyrazolo[1,5-a]pyrimidine-2-carboxylate (220 mg, 0.464 mmol) in EtOH (5 mL) was added 1N NaOH (0.464 mL, 0.464 mmol) and the resulting mixture was stirred at room temp for 4 h. At this point LCMS indicated completion of reaction. Solvents were then removed under reduced pressure and the residue was diluted with water (3 mL), acidified with 1N HCl, extracted with ethyl acetate (25 mL), washed with brine (10 mL), dried (Na$_2$SO$_4$), filtered and concentrated to afford (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (180 mg, 0.403 mmol, 87% yield) as light yellow solid. $^1$H NMR (400 MHz, CDCl$_3$) δ 7.14 (s, 1H), 5.95 (s, 1H), 4.31-4.16 (m, 2H), 2.66 (s, 3H), 1.82-1.60 (m, 4H), 1.60-1.46 (m, 4H), 1.28-1.22 (m, 12H), 1.14 (s, 6H). LCMS (M+H)=447.4.

Example 151

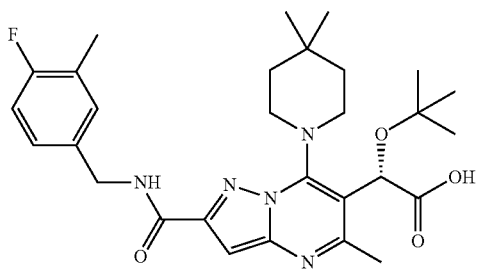 [SMILES: Cc1cc(CNC(=O)c2cc3nc(C)c([C@H](OC(C)(C)C)C(=O)O)c(N4CCC(C)(C)CC4)n3n2)ccc1F]

(S)-2-(tert-Butoxy)-2-(7-(4,4-dimethylpiperidin-1-yl)-2-((4-fluoro-3-methylbenzyl)carbamoyl)-5-methylpyrazolo[1,5-a]pyrimidin-6-yl)acetic acid To a mixture of (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (50 mg, 0.112 mmol) and (4-fluoro-3-methylphenyl)methanamine (31.2 mg, 0.224 mmol) in DMF (2 mL) was added DIEA (0.098 mL, 0.560 mmol), HATU (85 mg, 0.224 mmol) and DMAP (2.74 mg, 0.022 mmol) and the resulting mixture was stirred at room temp for 16 h. At this point LCMS indicated completion of reaction. Water was then added and the mixture was extracted with ethyl acetate (25 mL), washed with brine (15 mL), dried (Na$_2$SO$_4$), filtered and concentrated. Crude was then treated with 1N NaOH (0.336 mL, 0.336 mmol) in MeOH (2.000 mL) at 60° C. for 5 h. The mixture was then cooled and purified by prep-HPLC to afford (S)-2-(tert-butoxy)-2-(7-(4,4-dimethylpiperidin-1-yl)-2-((4-fluoro-3-methylbenzyl)carbamoyl)-5-methylpyrazolo[1,5-a]pyrimidin-6-yl)acetic acid (26.2 mg, 0.046 mmol, 41.2% yield). $^1$H NMR (500 MHz, DMSO-d$_6$) δ 8.76 (t, J=6.3 Hz, 1H), 7.27 (d, J=7.6 Hz, 1H), 7.23-7.17 (m, 1H), 7.10 (t, J=9.0 Hz, 1H), 6.82 (s, 1H), 5.43 (s, 1H), 4.48 (d, J=6.1 Hz, 2H), 3.32-3.39 (m, 4H), 2.23 (s, 3H), 1.92 (s, 3H), 1.60 (br. s., 2H), 1.46 (br. s., 2H), 1.14 (s, 9H), 1.07 (br. s., 6H). LCMS (M+H)=540.5.

Example 152

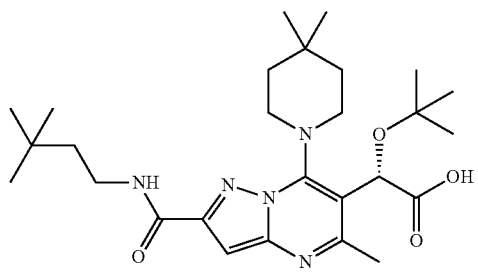 [SMILES: Cc1nc2cc(C(=O)NCCC(C)(C)C)nn2c(N2CCC(C)(C)CC2)c1[C@H](OC(C)(C)C)C(=O)O]

(S)-2-(tert-Butoxy)-2-(2-((3,3-dimethylbutyl)carbamoyl)-7-(4,4-dimethylpiperidin-1-yl)-5-methylpyrazolo[1,5-a]pyrimidin-6-yl)acetic acid To a mixture of (S)-6-(1-(tert-butoxy)-2-ethoxy-2-oxoethyl)-7-(4,4-dimethylpiperidin-1-yl)-5-methylpyrazolo[1,5-a]pyrimidine-2-carboxylic acid (50 mg, 0.112 mmol) and 3,3-dimethylbutan-1-amine (22.66 mg, 0.224 mmol) in DMF (2 mL) was added DIEA (0.098 mL, 0.560 mmol), HATU (85 mg, 0.224 mmol) and DMAP (2.74 mg, 0.022 mmol) and the resulting mixture was stirred at room temp for 16 h. At this point LCMS indicated completion of reaction. Water was then added and the mixture was extracted with ethyl acetate (25 mL), washed with brine (15 mL), dried (Na$_2$SO$_4$), filtered and concentrated. Crude was then treated with 1N NaOH (0.336 mL, 0.336 mmol) in MeOH (2.000 mL) at 60° C. for 5 h. Mixture was then cooled and purified by prep-HPLC to afford (S)-2-(tert-butoxy)-2-(2-((3,3-dimethylbutyl)carbamoyl)-7-(4,4-dimethylpiperidin-1-yl)-5-methylpyrazolo[1,5-a]pyrimidin-6-yl)acetic acid (41.6 mg, 0.079 mmol, 70.4% yield). $^1$H NMR (500 MHz, DMSO-d$_6$) δ 8.13 (t, J=5.6 Hz, 1H), 6.77 (s, 1H), 5.46 (s, 1H), 3.37-3.28 (m, 6H), 1.92 (s, 3H), 1.67-1.55 (m, 2H), 1.54-1.40 (m, 4H), 1.14 (s, 9H), 1.08 (br. s., 6H), 0.96 (s, 9H). LCMS (M+H)=502.5.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

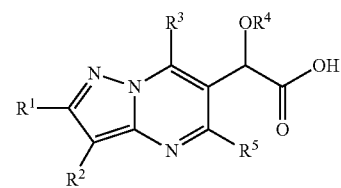

where:

R$^1$ is CONR$^6$R$^7$;

R$^2$ is hydrogen, halo, or alkyl;

R$^3$ is alkyl; alkenyl; cycloalkyl or cycloalkenyl substituted with 0-2 alkyl substituents; azetidinyl, pyrrolidinyl, piperidinyl, piperazinyl, morpholinyl, homopiperidinyl, homopiperazinyl, or homomorpholinyl substituted with 0-3 substituents selected from halo, alkyl, haloalkyl, hydroxy, alkoxy, haloalkoxy, carboxy, and carboxamido; or Ar$^2$;

R$^4$ is alkyl or haloalkyl;

R$^5$ is alkyl;

R$^6$ is alkyl, (R$^5$)alkyl, Ar$^1$, (Ar$^1$)alkyl, (Ar$^1$)alkenyl, (Ar$^1$)alkynyl, (Ar$^1$)cycloalkyl, alkylSO$_2$, (Ar$^1$)SO$_2$, or (Ar$^1$)alkylSO$_2$;

R$^7$ is hydrogen, alkyl, or alkoxy;

or where NR$^6$R$^7$ together form piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, (Ar$^3$)alkyl, and Ar$^3$;

R$^8$ is adamantyl, hydroxyadamantyl, hydroxycycloalkyl, tetrahydrofuranyl, tetrahydropyranyl, pyrrolidinonyl, alkoxy, alkylthio, phenoxy, or (phenyl)NH;

or R$^8$ is piperidinyl, piperazinyl, morpholinyl, or tetrahydronapthalinyl, and is substituted with 0-1 substituents selected from alkyl, alkylCO, alkylCO$_2$, cycloalkylCO, cycloalkylCO$_2$, (Ar$^3$)alkyl, Ar$^3$, benzodioxolyl, piperidinyl morpholinyl, and (morpholinyl)ethyl;

R$^9$ is piperidinyl, piperazinyl, or morpholinyl;

R$^{10}$ is hydrogen or alkyl;

R$^{11}$ is hydrogen or alkyl;

or NR$^{10}$R$^{11}$ is piperidinyl, piperazinyl, or morpholinyl;

Ar$^1$ is phenyl, pyridinyl, pyrrolyl, furanyl, thienyl, pyrazolyl, isoxazolyl, isothiazolyl, imidazolyl, oxazolyl, thiazolyl, benzodioxolyl, or benzthiazolyl, and is substituted with 0-5 substituents selected from halo, hydroxy, alkoxy, cyano, alkyl, cycloalkyl, haloalkyl, haloalkoxy, phenoxy, NR$^{10}$R$^{11}$, CONR$^{10}$R$^{11}$, alkylSO$_2$, SO$_2$NR$^{10}$R$^{11}$, Ar$^3$SO$_2$, (Ar$^3$)alkylSO$_2$, R$^9$, and Ar$^4$;

Ar$^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;

or Ar$^2$ is

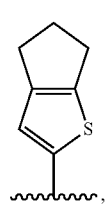, 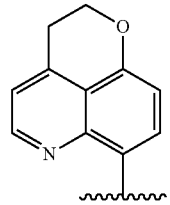, 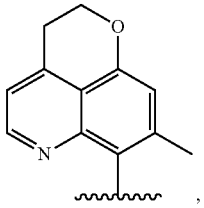,

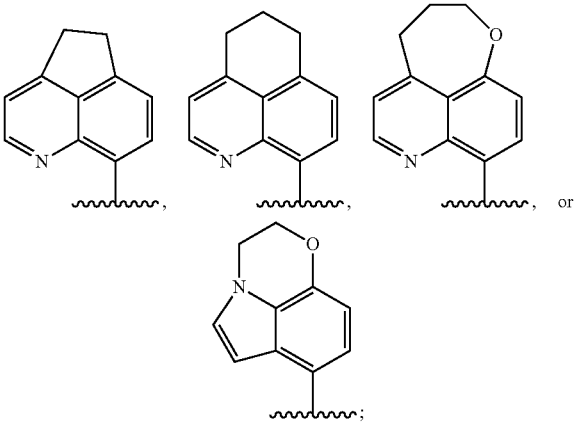

Ar$^3$ is phenyl substituted with 0-3 substituents selected from halo, alkyl, and alkoxy; and Ar$^4$ is phenyl, pyridinyl, pyrimidinyl, pyrrolyl, pyrazolyl, imidazolyl, or triazolyl, and is substituted with 0-1 alkyl substituents;

or a pharmaceutically acceptable salt thereof.

2. A compound of claim 1
where:

R$^1$ is CONR$^6$R$^7$;

R$^2$ is hydrogen, halo, or alkyl;

R$^3$ is alkyl, cycloalkyl, or Ar$^2$;

R$^4$ is alkyl or haloalkyl;

R$^5$ is alkyl;

R$^6$ is (R$^8$)alkyl, Ar$^1$, (Ar$^1$)alkyl, (Ar$^1$)alkenyl, (Ar$^1$)alkynyl, (Ar$^1$)cycloalkyl, alkylSO$_2$, (Ar$^1$)SO$_2$, or (Ar$^1$)alkylSO$_2$;

R$^7$ is hydrogen, alkyl, or alkoxy;

or where NR$^6$R$^7$ together form piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, (Ar$^3$)alkyl, and Ar$^3$;

R$^8$ is adamantyl, hydroxyadamantyl, hydroxycycloalkyl, tetrahydrofuranyl, tetrahydropyranyl, pyrrolidinonyl, alkoxy, alkylthio, phenoxy, or (phenyl)NH;

or R$^8$ is piperidinyl, piperazinyl, morpholinyl, or tetrahydronapthalinyl, and is substituted with 0-1 substituents selected from alkyl, alkylCO, alkylCO$_2$, cycloalkylCO, cycloalkylCO$_2$, (Ar$^3$)alkyl, Ar$^3$, benzodioxolyl, piperidinyl morpholinyl, and (morpholinyl)ethyl;

R$^9$ is piperidinyl, piperazinyl, or morpholinyl;

R$^{10}$ is hydrogen or alkyl;

R$^{11}$ is hydrogen or alkyl;

or NR$^{10}$R$^{11}$ is piperidinyl, piperazinyl, or morpholinyl;

Ar$^1$ is phenyl, pyridinyl, pyrrolyl, furanyl, thienyl, pyrazolyl, isoxazolyl, isothiazolyl, imidazolyl, oxazolyl, thiazolyl, benzodioxolyl, or benzthiazolyl, and is substituted with 0-5 substituents selected from halo, hydroxy, alkoxy, cyano, alkyl, cycloalkyl, haloalkyl, haloalkoxy, phenoxy, NR$^{10}$R$^{11}$, CONR$^{10}$R$^{11}$, alkylSO$_2$, SO$_2$NR$^{10}$R$^{11}$, Ar$^3$SO$_2$, (Ar$^3$)alkylSO$_2$, R$^9$, and Ar$^4$;

Ar$^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;

or $Ar^2$ is

[structures]

$Ar^3$ is phenyl substituted with 0-3 substituents selected from halo, alkyl, and alkoxy; and $Ar^4$ is phenyl, pyridinyl, pyrimidinyl, pyrrolyl, pyrazolyl, imidazolyl, or triazolyl, and is substituted with 0-1 alkyl substituents;

or a pharmaceutically acceptable salt thereof.

3. A compound of claim 1 where:
$R^1$ is $CONR^6R^7$;
$R^2$ is hydrogen;
$R^3$ is $Ar^2$;
$R^4$ is alkyl;
$R^5$ is alkyl;
$R^6$ is hydrogen, alkyl, alkenyl, alkynyl, (cycloalkyl)alkyl, cycloalkyl, cycloalkenyl, alkenylcycloalkyl, alkynylcycloalkyl, haloalkyl, haloalkenyl, haloalkynyl, $(R^8)$alkyl, $Ar^1$, $(Ar^1)$alkyl, $(Ar^1)$alkenyl, $(Ar^1)$alkynyl, $(Ar^1)$cycloalkyl, alkylSO$_2$, $(Ar^1)SO_2$, or $(Ar^1)$alkylSO$_2$;
$R^7$ is hydrogen, alkyl, or alkoxy;
$NR^6R^7$ together form azetidinyl, pyrrolidinyl, piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, $(Ar^3)$alkyl, and, $Ar^3$;
$R^8$ is adamantyl, hydroxyadamantyl, hydroxycycloalkyl, tetrahydrofuranyl, tetrahydropyranyl, pyrrolidinonyl alkoxy, alkylthio, phenoxy, or (phenyl)NH;
or $R^8$ is azetidinyl, pyrrolidinyl, piperidinyl, piperazinyl, morpholinyl, or tetrahydronapthalinyl, and is substituted with 0-1 substituents selected from alkyl, alkylCO, alkylCO$_2$, cycloalkylCO, cycloalkylCO$_2$, $(Ar^3)$alkyl, $Ar^3$, benzodioxolyl, piperidinyl morpholinyl, and (morpholinyl)ethyl;
$R^9$ is azetidinyl, pyrrolidinyl, piperidinyl, piperazinyl, or morpholinyl;
$R^{10}$ is hydrogen or alkyl;
$R^{11}$ is hydrogen or alkyl;
or $NR^{10}R^{11}$ is azetidinyl, pyrrolidinyl, piperidinyl, piperazinyl, or morpholinyl;
$Ar^1$ is phenyl, pyridinyl, furanyl, imidazolyl, thiazolyl, benzodioxolyl, or benzthiazolyl, and is substituted with 0-5 substituents selected from halo, hydroxy, alkoxy, cyano, alkyl, cycloalkyl, haloalkyl, haloalkoxy, phenoxy, $NR^{10}R^{11}$, $CONR^{10}R^{11}$, alkylSO$_2$, SO$_2NR^{10}R^{11}$, $Ar^3SO_2$, $(Ar^3)$alkylSO$_2$, $R^9$, and $Ar^4$;
$Ar^2$ is chromanyl substituted with 0-3 substituents selected from halo and alkyl;
$Ar^3$ is phenyl substituted with 0-3 substituents selected from halo, alkyl, and alkoxy; and
$Ar^4$ is phenyl, pyrimidinyl, pyrrolyl, or triazolyl, and is substituted with 0-1 alkyl substituents;

or a pharmaceutically acceptable salt thereof.

4. A compound of claim 1 where $R^6$ is $(Ar^1)$alkyl, or a pharmaceutically acceptable salt thereof.

5. A compound of claim 3 where $R^6$ is $(Ar^1)CH_2$, or a pharmaceutically acceptable salt thereof.

6. A compound of claim 4 where $Ar^1$ is phenyl or pyridinyl, and is substituted with 0-5 substituents selected from halo, hydroxy, alkoxy, cyano, alkyl, cycloalkyl, haloalkyl, haloalkoxy, phenoxy, $NR^{10}R^{11}$, $CONR^{10}R^{11}$, alkylSO$_2$, SO$_2NR^{10}R^{11}$, $Ar^3SO_2$, $(Ar^3)$alkylSO$_2$, $R^9$, and $Ar^4$, or a pharmaceutically acceptable salt thereof.

7. A compound of claim 1 where $(R^8)$alkyl, or a pharmaceutically acceptable salt thereof.

8. A compound of claim 1 where $NR^6R^7$ together form piperidinyl, piperazinyl, morpholinyl, or tetrahydronapthalinyl, and is substituted with 0-1 substituents selected from alkyl, hydroxyalkyl, alkoxyalkyl, (benzodioxolyl)alkyl, piperidinyl, (morpholinyl)alkyl, $(Ar^3)$alkyl, and AP, or a pharmaceutically acceptable salt thereof.

9. A compound of claim 1 where $Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;

or $Ar^2$ is

[structures]

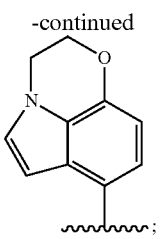

or a pharmaceutically acceptable salt thereof.

10. A compound of claim 1 where Ar² is chromanyl and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido, or a pharmaceutically acceptable salt thereof.

11. A compound of claim 9 where Ar² is chromanyl and is substituted with 0-3 substituents selected from halo and alkyl, or a pharmaceutically acceptable salt thereof.

12. A compound of claim 1 selected from the group consisting of (2S)-2-tert-butoxy-2-(7-(8-fluoro-5-methylchroman-6-yl)-2-(4-fluorobenzylcarbamoyl)-5-methylpyrazolo[1,5-a]pyrimidin-6-yl)acetic acid;

(2S)-2-(tert-Butoxy)-2-(7-(8-fluoro-5-methylchroman-6-yl)-2-(((1-isobutyrylpiperidin-4-yl)methyl)carbamoyl)-5-methylpyrazolo[1,5-a]pyrimidin-6-yl)acetic acid;

(2S)-2-(tert-Butoxy)-2-(2-((4-fluoro-3-methylbenzyl)carbamoyl)-7-(8-fluoro-5-methylchroman-6-yl)-5-methylpyrazolo[1,5-a]pyrimidin-6-yl)acetic acid;

(2S)-2-(2-(Benzylcarbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-5-methyl-2-((4-methylbenzyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((3-methylbenzyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((2-methylbenzyl)carbamoyl)pyrazolo[1,5-a]pyrimidin-6-yl)acetic acid;

(2S)-2-(tert-butoxy)-2-(7-(8-fluoro-5-methylchroman-6-yl)-2-((4-fluorobenzyl)(methyl)carbamoyl)-5-methylpyrazolo[1,5-a]pyrimidin-6-yl)acetic acid;

(2S)-2-(tert-butoxy)-2-(2-((4-fluoro-2-(5-methyl-1H-1,2,4-triazol-1-yl)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-2-(5-methyl-1H-1,2,3-triazol-1-yl)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-2-(1H-1,2,4-triazol-1-yl)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-2-(2-oxopyrrolidin-1-yl)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((phenylsulfonyl)carbamoyl)pyrazolo[1,5-a]pyrimidin-6-yl)acetic acid;

(2S)-2-(2-((benzylsulfonyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-5-methyl-2-(p-tolylcarbamoyl)pyrazolo[1,5-a]pyrimidin-6-yl)acetic acid;

(2S)-2-(tert-butoxy)-2-(2-((cyclohexylmethyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-2-((4-fluorobenzyl)(methoxy)carbamoyl)-5-methylpyrazolo[1,5-a]pyrimidin-6-yl)acetic acid;

(2S)-2-(tert-butoxy)-2-(2-((4-fluoro-2-(1-methyl-1H-1,2,4-triazol-5-yl)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-(methyl(2-methylbenzyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(methyl(3-methylbenzyl)carbamoyl)pyrazolo[1,5-a]pyrimidin-6-yl)acetic acid;

(2S)-2-(tert-butoxy)-2-(2-((4-ethylbenzyl)(methyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-2-((2-fluorobenzyl)(methyl)carbamoyl)-5-methylpyrazolo[1,5-a]pyrimidin-6-yl)acetic acid;

(2S)-2-(tert-butoxy)-2-(7-(8-fluoro-5-methylchroman-6-yl)-2-((3-fluorobenzyl)(methyl)carbamoyl)-5-methylpyrazolo[1,5-a]pyrimidin-6-yl)acetic acid;

(2S)-2-(tert-butoxy)-2-(2-((3-ethyl-4-fluorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-3-propylbenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((3-cyclopropyl-4-fluorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2((3-(difluoromethyl)-4-fluorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-2-(methylsulfonyl)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-2-methoxybenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-2-(methylcarbamoyl)benzyl)carbamoyl)-7-(8-fluoro-5-methylchroman-6-yl)-5-methylpyrazolo[1,5-a]pyrimidin-6-yl)acetic acid (2S)-2-(tert-butoxy)-2-(2-((4-butylbenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-(methyl(4-methylbenzyl)carbamoyl)pyrazolo[1,5-a]pyrimidin-6-yl)acetic acid;

(2S)-2-(2-(benzyl(methyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(2-((benzo[d][1,3]dioxol-5-ylmethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(2-((4-fluoro-3-methoxybenzyl) carbamoyl)-7-(8-fluoro-5-methylchroman-6-yl)-5-methylpyrazolo[1,5-a]pyrimidin-6-yl)acetic acid (2S)-2-(tert-butoxy)-2-(2(((3,5-difluoropyridin-2-yl)methyl)carbamoyl)-7-(8-fluoro-5-methylchroman-6-yl)-5-methylpyrazolo[1,5-a]pyrimidin-6-yl)acetic acid;

(2S)-2-(2-((3-(1H-imidazol-1-yl)propyl)(methyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-2-((furan-2-ylmethyl)carbamoyl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((1-phenylethyl)carbamoyl)pyrazolo[1,5-a]pyrimidin-6-yl)acetic acid;

(2S)-2-(tert-butoxy)-2-(2-((2-chlorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((3,4-dimethoxybenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-2-((2-methoxybenzyl)carbamoyl)-5-methylpyrazolo[1,5-a]pyrimidin-6-yl)acetic acid;

(2S)-2-(tert-butoxy)-2-(2-((cyclopropylmethyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((4-(trifluoromethoxy)benzyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(((2-phenylthiazol-4-yl)methyl)carbamoyl)pyrazolo[1,5-a]pyrimidin-6-yl)acetic acid;

(2S)-2-(tert-butoxy)-2-(2-((4-chlorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((2-(phenylamino)ethyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(phenethylcarbamoyl)pyrazolo[1,5-a]pyrimidin-6-yl)acetic acid;

(2S)-2-(tert-butoxy)-2-(7-(8-fluoro-5-methylchroman-6-yl)-2-(isopentylcarbamoyl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((3-phenylpropyl)carbamoyl)pyrazolo[1,5-a]pyrimidin-6-yl)acetic acid;

(2S)-2-(2-((3-(1H-imidazol-1-yl)propyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(2-((4-(dimethylamino)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((4-sulfamoylbenzyl)carbamoyl)pyrazolo[1,5-a]pyrimidin-6-yl)acetic acid;

(2S)-2-(tert-butoxy)-2-(2-((3-chlorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((2-phenoxyethyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(((1S,2R)-2-phenylcyclopropyl)carbamoyl)pyrazolo[1,5-a]pyrimidin-6-yl)acetic acid;

(2S)-2-(tert-butoxy)-2-(7-(8-fluoro-5-methylchroman-6-yl)-2-((4-fluorophenethyl)carbamoyl)-5-methylpyrazolo[1,5-a]pyrimidin-6-yl)acetic acid;

(2S)-2-(tert-butoxy)-2-(7-(8-fluoro-5-methylchroman-6-yl)-2-(((1-isobutyrylpiperidin-4-yl)methyl)carbamoyl)-5-methylpyrazolo[1,5-a]pyrimidin-6-yl)acetic acid;

(2S)-2-(tert-butoxy)-2-(2-(((1-(cyclopropanecarbonyl)piperidin-4-yl)methyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((1-(tert-butoxycarbonyl)piperidin-4-yl)methyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((3-fluoro-4-methylbenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((pyridin-3-ylmethyl)carbamoyl)pyrazolo[1,5-a]pyrimidin-6-yl)acetic acid;

(2S)-2-(tert-butoxy)-2-(2-((3,3-dimethylbutyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-fluoro-2-hydroxybenzyl)carbamoyl)-7-(8-fluoro-5-methylchroman-6-yl)-5-methylpyrazolo[1,4-a]pyrimidin-6yl)acetic acid;

(2S)-2-(tert-butoxy)-2-(7-(8-fluoro-5-methylchroman-6-yl)-5-methyl-2-((3-(trifluoromethyl)benzyl)carbamoyl)pyrazolo[1,5-a]pyrimidin-6-yl)acetic acid;

(2S)-2-(tert-butoxy)-2-(7-(8-fluoro-5-methylchroman-6-yl)-2-((4-methoxyphenethyl)carbamoyl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((4-(trifluoromethyl)benzyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((3-(trifluoromethoxy)benzyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((4-phenoxybenzyl)carbamoyl)pyrazolo[1,5-a]pyrimidin-6-yl)acetic acid;

(2S)-2-(2-((([1,1'-biphenyl]-3-ylmethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(2-((([1,1'-biphenyl]-4-ylmethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-2-((3-methoxybenzyl)carbamoyl)-5-methylpyrazolo[1,5-a]pyrimidin-6-yl)acetic acid;

(2S)-2-(2-((2-(1-benzylpiperidin-4-yl)ethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(2-((4-cyclohexylphenyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((2-(1-methylpyrrolidin-2-yl)ethyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((2-(pyrrolidin-1-yl)ethyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((3-(2-oxopyrrolidin-1-yl)propyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(((tetrahydrofuran-2-yl)methyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(4-phenylpiperidine-1-carbonyl)pyrazolo[1,5-a]pyrimidin-6-yl)acetic acid;

(2S)-2-(tert-butoxy)-2-(7-(8-fluoro-5-methylchroman-6-yl)-5-methyl-2-(1,2,3,4-tetrahydroisoquinoline-2-carbonyl)pyrazolo[1,5-a]pyrimidin-6-yl)acetic acid;

(2S)-2-(tert-butoxy)-2-(2-(4-(3-chlorophenyl)piperazine-1-carbonyl)-7-(8-fluoro-5-methylchroman-6-yl)-5-methylpyrazolo[1,5-a]pyrimidin-6-yl)acetic acid;

(2S)-2-(tert-butoxy)-2-(2-((3-chlorophenethyl)carbamoyl)-7-(8-fluoro-5-methylchroman-6-yl)-5-methylpyrazolo[1,5-a]pyrimidin-6-yl)acetic acid;

(2S)-2-(2-((1-benzylpyrrolidin-3-yl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(2-(4-ethylpiperazine-1-carbonyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((1-methyl-3-phenyl-1H-pyrazol-5-yl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((3-(2-methylpyrimidin-4-yl)phenyl)carbamoyl)pyrazolo[1,5-a]pyrimidin-6-yl)acetic acid;

(2S)-2-(tert-butoxy)-2-(2-(4-(4-chlorophenyl)piperidine-1-carbonyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-2-(4-(4-fluorophenyl)piperazine-1-carbonyl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((2-morpholinoethyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(methyl(2-(pyridin-2-yl)ethyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(4-phenethylpiperazine-1-carbonyl)pyrazolo[1,5-a]pyrimidin-6-yl)acetic acid;

(2S)-2-(tert-butoxy)-2-(7-(8-fluoro-5-methylchroman-6-yl)-5-methyl-2-(4-(2-morpholinoethyl)piperazine-1-carbonyl)pyrazolo[1,5-a]pyrimidin-6-yl)acetic acid;

(2S)-2-(2-(4-(benzo[d][1,3]dioxol-5-ylmethyl)piperazine-1-carbonyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-5-methyl-2-(4-phenylpiperazine-1-carbonyl)pyrazolo[1,5-a]pyrimidin-6-yl)acetic acid;

(2S)-2-(2-(4-benzylpiperazine-1-carbonyl)-7-(8-fluoro-5-methylchroman-6-yl)-5-methylpyrazolo[1,5-a]pyrimidin-6-yl)-2-(tert-butoxy)acetic acid;

(2S)-2-(2-([1,4'-bipiperidine]-1'-carbonyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-5-methyl-2-(methyl(phenethyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(methyl(pyridin-3-ylmethyl)carbamoyl)pyrazolo[1,5-a]pyrimidin-6-yl)acetic acid;

(2 S)-2-(tert-butoxy)-2-(7-(8-fluoro-5-methylchroman-6-yl)-2-(isopentyl(methyl)carbamoyl)-5-methylpyrazolo[1,5-a]pyrimidin-6-yl)acetic acid;

(2S)-2-(2-((3-(1H-pyrrol-1-yl)benzyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-5-methyl-2-((3-morpholinobenzyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((tetrahydro-2H-pyran-4-yl)methyl)carbamoyl)pyrazolo[1,5-a]pyrimidin-6-yl)acetic acid;

(2S)-2-(tert-butoxy)-2-(7-(8-fluoro-5-methylchroman-6-yl)-2-((2-isopropoxyethyl)carbamoyl)-5-methylpyrazolo[1,5-a]pyrimidin-6-yl)acetic acid;

(2S)-2-(tert-butoxy)-2-(2-((2-(tert-butoxy)ethyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((pyridin-2-ylmethyl)carbamoyl)pyrazolo[1,5-a]pyrimidin-6-yl)acetic acid;

(2S)-2-(2-(4-benzylpiperidine-1-carbonyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-2-(4-(2-hydroxyethyl)piperidine-1-carbonyl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((3-morpholinopropyl)carbamoyl)pyrazolo[1,5-a]pyrimidin-6-yl)acetic acid;

(2S)-2-(tert-butoxy)-2-(2-((2,4-dichlorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((3 dichlorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-2-((4-methoxybenzyl)carbamoyl)-5-methylpyrazolo[1,5-a]pyrimidin-6-yl)acetic acid;

(2S)-2-(tert-butoxy)-2-(2((2-chlorophenethyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((4-chlorophenethyl)carbamoyl)-7-(8-fluoro-5-methylchroman-6-yl)-5-methylpyrazolo[1,5-a]pyrimidin-6-yl)acetic acid;

(2S)-2-(2-(benzyl(isopropyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(2-(butylcarbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((3,4-dichlorobenzyl)(methyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-(4-(4-chlorophenyl)piperazine-1-carbonyl)-7-(8-fluoro-5-methylchroman-6-yl)-5-methylpyrazolo[1,5-a]pyrimidin-6-yl)acetic acid;

(2S)-2-(tert-butoxy)-2-(2-((2,3-dichlorobenzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2-((3,5-dichlorobenzyl)carbamoyl)-7-(8-fluoro-5-methylchroman-6-yl)-5-methylpyrazolo[1,5-a]pyrimidin-6-yl)acetic acid;

(2S)-2-(2-((2-(benzo[d]thiazol-2-yl)ethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(2-((4-chloro-3-(trifluoromethyl)benzyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(2((4-cyanobenzyl)carbamoyl)-7-(8-fluoro-5-methylchroman-6-yl)-5-methylpyrazolo[1,5-a]pyrimidin-6-yl)acetic acid;

(2S)-2-(2-((benzo[d]thiazol-2-ylmethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-5-methyl-2-(phenylcarbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-(propylcarbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((2-(trifluoromethyl)benzyl)carbamoyl)pyrazolo[1,5-a]pyrimidin-6-yl)acetic acid;

(2S)-2-(2-(((3S,5S,7S)-adamantan-1-ylmethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(7-(8-fluoro-5-methylchroman-6-yl)-5-methyl-2-(neopentylcarbamoyl)pyrazolo[1,5-a]pyrimidin-6-yl)acetic acid;

(2S)-2-(tert-butoxy)-2-(2-((2-cyclohexylethyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((2-(tetrahydro-2H-pyran-4-yl)ethyl)carbamoyl)pyrazolo[1,5-a]pyrimidin-6-yl)acetic acid;

(2 S)-2-(2-((2-((3S,5S,7S)-adamantan-1-yl)ethyl)carbamoyl)-7-(8-fluoro-5-methylchroman-6-yl)-5-methylpyrazolo[1,5-a]pyrimidin-6-yl)-2-(tert-butoxy)acetic acid;

(2S)-2-(tert-butoxy)-2-(2-((3-cyclohexylpropyl)carbamoyl)-7-(8-fluoro-5-methylchroman-6-yl)-5-methylpyrazolo[1,5-a]pyrimidin-6-yl)acetic acid;

(2S)-2-(tert-butoxy)-2-(7-(8-fluoro-5-methylchroman-6-yl)-5-methyl-2-((3-(tetrahydrofuran-3-yl)propyl)carbamoyl)pyrazolo[1,5-a]pyrimidin-6-yl)acetic acid;

(2S)-2-(tert-butoxy)-2-(7-(8-fluoro-5-methylchroman-6-yl)-5-methyl-2-((2-propoxyethyl)carbamoyl)pyrazolo[1,5-a]pyrimidin-6-yl)acetic acid;

(2S)-2-(tert-butoxy)-2-(7-(8-fluoro-5-methylchroman-6-yl)-2-((2-(1-hydroxycyclopentyl)ethyl)carbamoyl)-5-methylpyrazolo[1,5-a]pyrimidin-6-yl)acetic acid;

(2S)-2-(tert-butoxy)-2-(7-(8-fluoro-5-methylchroman-6-yl)-2-((((1R,3R,4S,5R,7S)-4-hydroxyadamantan-1-yl)methyl)carbamoyl)-5-methylpyrazolo[1,5-a]pyrimidin-6-yl)acetic acid;

(2S)-2-(tert-butoxy)-2-(2-((2-(tert-butylthio)ethyl)carbamoyl)-7-(8-fluoro-5-methylchroman-6-yl)-5-methylpyrazolo[1,5-a]pyrimidin-6-yl)acetic acid; and (2S)-2-(tert-butoxy)-2-(7-(8-fluoro-5-methylchroman-6-yl)-5-methyl-2-(methylcarbamoyl)pyrazolo[1,5-a]pyrimidin-6-yl)acetic acid;

(S)-2-(tert-Butoxy)-2-((S)-7-(8-fluoro-5-methylchroman-6-yl)-2-(4-(4-fluorophenyl)piperidine-1-carbonyl)-5-methylpyrazolo[1,5-a]pyrimidin-6-yl)acetic acid (2S)-2-(tert-Butoxy)-2-(3-fluoro-2-((4-fluoro-3-methylbenzyl)carbamoyl)-7-(8-fluoro-5-methylchroman-6-yl)-5-methylpyrazolo[1,5-a]pyrimidin-6-yl)acetic acid (2S)-2-(tert-Butoxy)-2-(3-chloro-2-((4-fluoro-3-methylbenzyl)carbamoyl)-7-(8-fluoro-5-methylchroman-6-yl)-5-methylpyrazolo[1,5-a]pyrimidin-6-yl)acetic acid (2S)-2-(test-Butoxy)-2-(7-(5-chloro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid (2S)-2-(tert-Butoxy)-2-(7-(5-chloro-3,4-dihydro-2H-benzo[b][1,4]oxazin-6-yl)-5-methyl-2-((2-pentylbenzyl)carbamoyl)pyrazolo[1,5-a]pyrimidin-6-yl)acetic acid (2S)-2-(tert-Butoxy)-2-(2-((2-butoxy-4-fluorobenzyl)carbamoyl)-7-(5-chloro-3,4-dihydro-2H-benzo[b][1,4]oxazin-6-yl)-5-methylpyrazolo[1,5-a]pyrimidin-6-yl)acetic acid (2S)-2-(tert-Butoxy)-2-(7-(5-chloro-3,4-dihydro-2H-benzo[b][1,4]oxazin-6-yl)-2-((3,3-dimethylbutyl)carbamoyl)-5-methylpyrazolo[1,5-a]pyrimidin-6-yl)acetic acid (2S)-2-(tert-Butoxy)-2-(7-(7-fluoro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid (2S)-2-(tert-Butoxy)-2-(2-((3,3-dimethylbutyl)carbamoyl)-7-(7-fluoro-3,4-dihydro-2H-benzo[b][1,4]oxazin-6-yl)-5-methylpyrazolo[1,5-a]pyrimidin-6-yl)acetic acid (S)-2-(tert-butoxy)-2-(7-(4,4-dimethylcyclohex-1-en-1-yl)-2-((4-fluoro-3-methylbenzyl)carbamoyl)-5-methylpyrazolo[1,5-a]pyrimidin-6-yl)acetic acid (S)-2-(tert-Butoxy)-2-(2((3,3-dimethylbutyl)carbamoyl)-7-(4,4-dimethylcyclohex-1-en-1-yl)-5-methylpyrazolo[1,5-a]pyrimidin-6-yl)acetic acid (S,E)-2-(tert-Butoxy)-2-(2-((4-fluoro-3-methylbenzyl)carbamoyl)-5-methyl-7-(4-methylpent-1-en-1-yl)pyrazolo[1,5-a]pyrimidin-6-yl)acetic acid (S,E)-2-(tert-Butoxy)-2-(2-((3,3-dimethylbutyl)carbamoyl)-5-methyl-7-(4-methylpent-1-en-1-yl)pyrazolo[1,5-a]pyrimidin-6-yl)acetic acid (S)-2-(test-Butoxy)-2-(7-(4,4-dimethylpiperidin-1-yl)-2-((4-fluoro-3-methylbenzyl)carbamoyl)-5-methylpyrazolo[1,5-a]pyrimidin-6-yl)acetic acid (S)-2-(tert-Butoxy)-2-(2((3,3-dimethylbutyl)carbamoyl)-7-(4,4-dimethylpiperidin-1-yl)-5-methylpyrazolo[1,5-a]pyrimidin-6-yl)acetic acid or a pharmaceutically acceptable salt thereof.

13. A compound of claim 1 selected from the group consisting of (S)-2-(tert-Butoxy)-2-((S)-7-(8-fluoro-5-methylchroman-6-yl)-2-(4-(4-fluorophenyl)piperidine-1-carbonyl)-5-methylpyrazolo[1,5-a]pyrimidin-6-yl)acetic acid;

(2S)-2-(tert-Butoxy)-2-(3-fluoro-2-((4-fluoro-3-methylbenzyl)carbamoyl)-7-(8-fluoro-5-methylchroman-6-yl)-5-methylpyrazolo[1,5-a]pyrimidin-6-yl)acetic acid;

(2S)-2-(tert-Butoxy)-2-(3-chloro-2-((4-fluoro-3-methylbenzyl)carbamoyl)-7-(8-fluoro-5-methylchroman-6-yl)-5-methylpyrazolo[1,5-a]pyrimidin-6-yl)acetic acid;

(2S)-2-(tert-Butoxy)-2-(7-(5-chloro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid;

(2S)-2-(tert-Butoxy)-2-(7-(5-chloro-3,4-dihydro-2H-benzo[b][1,4]oxazin-6-yl)-5-methyl-2-((2-pentylbenzyl)carbamoyl)pyrazolo[1,5-a]pyrimidin-6-yl)acetic acid;

(2S)-2-(tert-Butoxy)-2-(2-((2-butoxy-4-fluorobenzyl)carbamoyl)-7-(5-chloro-3,4-dihydro-2H-benzo[b][1,4]oxazin-6-yl)-5-methylpyrazolo[1,5-a]pyrimidin-6-yl)acetic acid;

(2S)-2-(tert-Butoxy)-2-(7-(5-chloro-3,4-dihydro-2H-benzo[b][1,4]oxazin-6-yl)-2-((3,3-dimethylbutyl)carbamoyl)-5-methylpyrazolo[1,5-a]pyrimidin-6-yl)acetic acid;

(2S)-2-(test-Butoxy)-2-(7-(7-fluoro-3,4-dihydro-2H-benzo[b][1,4]oxazin-6-yl)-2-((4-fluoro-3-methylbenzyl)carbamoyl)-5-methylpyrazolo[1,5-a]pyrimidin-6-yl)acetic acid;

(2S)-2-(tert-Butoxy)-2-(2-((3,3-dimethylbutyl)carbamoyl)-7-(7-fluoro-3,4-dihydro-2H-benzo[b][1,4]oxazin-6-yl)-5-methylpyrazolo[1,5-a]pyrimidin-6-yl)acetic acid;

(S)-2-(tert-butoxy)-2-(7-(4,4-dimethylcyclohex-1-en-1-yl)-2-((4-fluoro-3-methylbenzyl)carbamoyl)-5-methylpyrazolo[1,5-a]pyrimidin-6-yl)acetic acid;

(S)-2-(tert-Butoxy)-2-(2((3,3-dimethylbutyl)carbamoyl)-7-(4,4-dimethylcyclohex-1-en-1-yl)-5-methylpyrazolo[1,5-a]pyrimidin-6-yl)acetic acid;

(S,E)-2-(tert-Butoxy)-2-(2-((4-fluoro-3-methylbenzyl)carbamoyl)-5-methyl-7-(4-methylpent-1-en-1-yl)pyrazolo[1,5-a]pyrimidin-6-yl)acetic acid;

(S,E)-2-(tert-Butoxy)-2-(2-((3,3-dimethylbutyl)carbamoyl)-5-methyl-7-(4-methylpent-1-en-1-yl)pyrazolo[1,5-a]pyrimidin-6-yl)acetic acid;

(S)-2-(tert-Butoxy)-2-(7-(4,4-dimethylpiperidin-1-yl)-2-((4-fluoro-3-methylbenzyl)carbamoyl)-5-methylpyrazolo[1,5-a]pyrimidin-6-yl)acetic acid; and (S)-2-(tert-Butoxy)-2-(2-((3,3-dimethylbutyl)carbamoyl)-7-(4,4-dimethylpiperidin-1-yl)-5-methylpyrazolo[1,5-a]pyrimidin-6-yl)acetic acid;

or a pharmaceutically acceptable salt thereof.

14. A composition useful for treating HIV infection comprising a therapeutic amount of a compound of claim 1 and a pharmaceutically acceptable carrier.

15. A method for treating HIV infection comprising administering a therapeutically effective amount of a compound of claim 1, or a pharmaceutically acceptable salt thereof, to a patient in need thereof.

* * * * *